United States Patent
Kent et al.

(10) Patent No.: US 12,161,726 B2
(45) Date of Patent: Dec. 10, 2024

(54) BIOMIMETIC VESICLES AND USES THEREOF

(71) Applicants: Ohio State Innovation Foundation, Columbus, OH (US); Wisconsin Alumni Research Foundation, Madison, WI (US)

(72) Inventors: K. Craig Kent, Columbus, OH (US); Shaoqin Gong, Middleton, WI (US); Lianwang Guo, Columbus, OH (US); Bowen Wang, Columbus, OH (US); Guojun Chen, Madison, WI (US); Go Urabe, Columbus, OH (US)

(73) Assignees: Ohio State Innovation Foundation, Columbus, OH (US); Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 17/932,736

(22) Filed: Sep. 16, 2022

(65) Prior Publication Data
US 2023/0346972 A1 Nov. 2, 2023

Related U.S. Application Data

(63) Continuation of application No. 17/057,415, filed as application No. PCT/US2019/033861 on May 23, 2019, now Pat. No. 11,446,392.

(60) Provisional application No. 62/675,744, filed on May 23, 2018, provisional application No. 62/682,760, filed on Jun. 8, 2018.

(51) Int. Cl.
*A61K 47/69* (2017.01)
*A61K 9/51* (2006.01)
*A61K 45/06* (2006.01)
*B82Y 5/00* (2011.01)

(52) U.S. Cl.
CPC ........ *A61K 47/6937* (2017.08); *A61K 9/5153* (2013.01); *A61K 45/06* (2013.01); *B82Y 5/00* (2013.01)

(58) Field of Classification Search
CPC .. A61K 47/6937; A61K 9/5153; A61K 45/06; B82Y 5/00
See application file for complete search history.

(56) References Cited

U.S. PATENT DOCUMENTS

2018/0042844 A1 2/2018 Craig et al.
2019/0175754 A1 6/2019 Chen

FOREIGN PATENT DOCUMENTS

WO WO-2015008195 A1 * 1/2015 ........... A61K 31/785
WO WO-2015117158 A1 * 8/2015 ........... A61K 31/727

OTHER PUBLICATIONS

Guojun Chen, et al, A Review on Core-Shell Unimolecular Nanoparticles for Biomedical Applications, 130 Adv. Drug Del. Rev. 58 (Year: 2018).*
Guojun Chen, et al, KE108-Conjugated Unimolecular Micelles Loaded with a Novel HDAC Inhibitor Thailandepsin-A for Targeted Neuroendocrine Cancer Therapy, 97 Biomat. 22 (Year: 2016).*
Renata Jaskula-Sztul, et al, AB3-Loaded and Tumor-Targeted Unimolecular Micelles for Medullary Thyroid Cancer Treatment, 7 J Mater. Chem. B Mater; Biol. Med. 151 (Year: 2017).*
Hu, C.M., et al., "Naoparticle biointerfacing by platelet membrane cloaking," Nature, vol. 526, No. 7571 (2015), pp. 118-121.
European Search Report, EP App. 19807539.2, mailed Feb. 7, 2022.
Chen, Guojun, et al., "KE108-Conjugated Unimolecular Micelles Loaded with a Novel HDAC Inhibitor Thailandepsin-A for Targeted Neuroendocrine Cancer Therapy," Biomaterials, vol. 97 (2016), pp. 22-33.
Chen, Guojun, et al., "A Review on Core-Shell Unimolecular Nanoparticles for Biomedical Applications," Drug Delivery Reviews, vol. 130 (2018), pp. 58-72.
International Search Report issued for PCT/US2019/033861, mailed Sep. 12, 2019.
Brinkman, Ashley M., et al., "Aminoflavone-Loaded EGFR-Targeted Unimolecular Micelle Nanoparticles Exhibit Anti-Cancer Effects in Triple Negative Breast Cancer," Biomaterials, vol. 101 (2016), pp. 1-26.
Jaskula-Sztul, Renata, et al., "AB3-Loaded and Tumor-Targeted Unimolecular Micelles for Medullary Thyroid Cancer Treatment," Journal of Materials Chemistry, vol. 5, No. 1 (2017), pp. 151-159.
Chen, Guojun, et al., "Tumor-Targeted pH/Redox Dual-Sensitive Unimolecular Nanoparticles for Efficient siRNA Delivery," Journal of Controlled Release, vol. 259 (2017), pp. 105-114.

* cited by examiner

*Primary Examiner* — Sean M Basquill
(74) *Attorney, Agent, or Firm* — Thomas|Horstemeyer, LLP

(57) ABSTRACT

The present disclosure relates to unimolecular core-shell nanoparticle, nanoclusters thereof, and platelet biomimetic nanoclusters thereof. The disclosed compositions are useful for treating a subject with a disease or condition, such as a cardiovascular disease. In a further aspect, the cardiovascular disease can be a vascular stenosis or restenosis. Also described herein are methods of making and using the unimolecular core-shell nanoparticle, nanoclusters thereof, and platelet biomimetic nanoclusters thereof. This abstract is intended as a scanning tool for purposes of searching in the particular art and is not intended to be limiting of the present disclosure.

19 Claims, 33 Drawing Sheets
Specification includes a Sequence Listing.

BIOMIMETIC VESICLES AND USES THEREOF

CROSS-REFERENCE TO RELATED APPLICATIONS

This Application is a Continuation of U.S. application Ser. No. 17/057,415, filed Nov. 20, 2020, which is a National Stage of International Application No. PCT/US2019/033861, filed May 23, 2019, which claims the benefit of U.S. Provisional Application No. 62/675,744, filed on May 23, 2018, and U.S. Provisional Application No. 62/682,760, filed on Jun. 8, 2018, each of which is incorporated herein by reference in its entirety.

STATEMENT REGARDING FEDERALLY SPONSORED RESEARCH

This invention was made with government support under Grant Nos. R01 HL068673, R01 HL 133665, R01 HL129785, and R01 HL143469 awarded by the National Institutes of Health. The U.S. government has certain rights in the invention.

SEQUENCE LISTING

This application contains a sequence listing filed in ST.26 format entitled "222117-1051 Sequence Listing" created on Mar. 13, 2023. The content of the sequence listing is incorporated herein in its entirety.

BACKGROUND

Cardiovascular diseases are the leading cause of mortality and morbidity in developed countries. Endovascular interventions have been widely practiced to recanalize the stenosed vessels. However, there are two major complications associated with these procedures: (1) restenosis and (2) thrombosis. Restenosis is the re-narrowing of the reconstructed vessels due to smooth muscle cell (SMC) overgrowth. Although effective in inhibiting restenosis, currently applied endovascular interventions (e.g. rapamycin-coated stents) are associated with safety concerns. Specifically, an increased risk of thrombosis and related co-morbidities/mortalities have been reported following placement of these drug-eluting devices. This is largely due to the exacerbated damage on endothelial cells (EC) caused by the indiscriminative toxicity of the coated compounds as well as inflammatory reactions from the device itself. To solve the issue of thrombogenic risk, a new strategy is urgently needed for control of restenosis yet cause minimal damage to or even be beneficial to the endothelium.

As such, there exists a need for improved treatments for cardiovascular diseases. These needs and other needs are satisfied by the present disclosure.

SUMMARY

In accordance with the purpose(s) of the present disclosure, as embodied and broadly described herein, the disclosure, in one aspect, relates to compositions comprising a unimolecular core-shell nanoparticle and a therapeutic agent. In some aspects, the composition is a nanocluster comprising the unimolecular core-shell nanoparticle and the therapeutic agent. In further aspects, the composition is a biomimetic nanocluster. The disclosed compositions are useful for treating a subject with a disease or condition, such as a cardiovascular disease. In a further aspect, the cardiovascular disease can be a vascular stenosis or restenosis.

In various aspects, the present disclosure relates to a unimolecular core-shell nanoparticle comprising a functionalized polymer, wherein the functionalized polymer comprises a core-forming segment and a shell-forming segment.

In a further aspect, the present disclosure relates to nanoclusters comprising a plurality of disclosed unimolecular core-shell nanoparticles.

In a further aspect, the present disclosure relates to biomimetic nanoclusters comprising a membrane structure comprising a first membrane component; and a core structure comprising a disclosed nanocluster.

In a further aspect, the present disclosure relates to disclosed methods of making the disclosed unimolecular core-shell nanoparticles, nanoclusters, and biomimetic nanoclusters.

In a further aspect, the present disclosure relates to methods for treating a subject, the method comprising administering a disclosed unimolecular core-shell nanoparticle, a disclosed nanocluster, or a disclosed biomimetic nanocluster to the subject.

In a further aspect, the present disclosure relates to kits comprising the disclosed unimolecular core-shell nanoparticles, nanoclusters, and biomimetic nanoclusters and instructions to treat a subject using same.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described aspects are usable in all aspects of the disclosure taught herein. Furthermore, the individual features of the dependent claims, as well as all optional and preferred features and modifications of the described aspects are combinable and interchangeable with one another.

BRIEF DESCRIPTION OF THE DRAWINGS

Further aspects of the present disclosure will be readily appreciated upon review of the detailed description of its various aspects, described below, when taken in conjunction with the accompanying drawings.

FIG. 2A shows optical images of balloon-injured arteries and uninjured contralateral arteries were collected 5 days later for ex vivo imaging with an IVIS spectrum luminescence system (Ex/Em: 650/720 nm). Note Cy5 fluorescence was detected from injured, but not uninjured arteries. More images from other 5 rats are presented in FIG. 6. FIG. 2B shows a graph demonstrating the fluorescence quantification: Mean±SEM, n=6 rats;*p<0.05. Basal level fluorescence from uninjured control was used for normalization.

FIG. 3A shows representative images of Evans Blue-stained carotid arteries showing re-endothelialization. FIG. 3B shows the images in FIG. 3A quantified and plotted. Red side bars indicate the lengths of unstained arteries. Quantification: Mean±SEM, n=3 rats; *p<0.05 compared to either of the other two conditions. FIG. 3C shows Analysis of endothelial cell markers. Evans Blue-stained arteries were transiently fixed with RNAlater solution and subjected to RNA extraction and qPCR analysis. Quantification: Mean±SEM, n=3 rats; *p<0.05 compared to vehicle control.

FIG. 12A shows the relative mRNA levels for RANTES in spleen in response to the indicated treatments. FIG. 12B shows the relative mRNA levels for IL1β in spleen in response to the indicated treatments. FIG. 12C shows the relative mRNA levels for MCP1 in spleen in response to the indicated treatments.

FIG. 12D shows the relative mRNA levels for TNFα in spleen in response to the indicated treatments. FIG. 12E shows the relative mRNA levels for IL6 in spleen in response to the indicated treatments. FIG. 12F shows the relative mRNA levels for BAX in spleen in response to the indicated treatments. FIG. 12G shows the relative mRNA levels for RANTES in liver in response to the indicated treatments. FIG. 12H shows the relative mRNA levels for IL1β in liver in response to the indicated treatments. FIG. 12I shows the relative mRNA levels for MCP1 in liver in response to the indicated treatments. FIG. 12J shows the relative mRNA levels for TNFα in liver in response to the indicated treatments. FIG. 12K shows the relative mRNA levels for IL6 in liver in response to the indicated treatments. FIG. 12L shows the relative mRNA levels for BAX in liver in response to the indicated treatments.

FIG. 13A shows data obtained with RSMC cells and the indicated concentration of nanocluster or control treatment. FIG. 13B shows data obtained with HASMC cells and the indicated concentration of nanocluster or control treatment. FIG. 13C shows data obtained with REC cells and the indicated concentration of nanocluster or control treatment. FIG. 13D shows data obtained with HUVEC cells and the indicated concentration of nanocluster or control treatment. The data indicate that non-coated nanoclusters at the highest dose (200 µg/ml) reduced cell viability by ~50% in four lines of smooth muscle or endothelial cells compared to PBS control, whereas biomimetic (platelet membrane coated) nanoclusters and platelet membrane vesicles did not impair cell viability in either of these cells.

FIG. 14A shows data obtained with RSMC cells and the indicated concentration of nanocluster or control treatment. FIG. 14B shows data obtained with HASMC cells and the indicated concentration of nanocluster or control treatment. FIG. 14C shows data obtained with REC cells and the indicated concentration of nanocluster or control treatment. FIG. 14D shows data obtained with HUVEC cells and the indicated concentration of nanocluster or control treatment. The data indicate that non-coated nanoclusters at the highest dose (200 µg/ml) increased cell apoptosis in three lines of smooth muscle or endothelial cells compared to PBS control, whereas biomimetic (platelet membrane coated) nanoclusters and platelet membrane vesicles did not enhance apoptosis in either of the four lines of cells.

FIG. 15A: Cy5-tagged nanoclusters were coated with either platelet membranes or macrophage membranes as described in Examples, and were administered via retro-orbital injection (2.5 mg/kg animal weight) of mice at day 7 following aneurysm induction procedure (calcium phosphate perivascular application). Aneurysmal arteries and uninjured contralateral arteries were collected, as indicated, for imaging with an IVIS spectrum luminescence system (Ex/Em: 650/720 nm). It should be noted that Cy5 fluorescence was detected from aneurysmal, but not healthy arteries. FIG. 15B: Cy5-tagged nanoclusters were prepared and administered as described for FIG. 15A. Mice were euthanized at indicated time points and organs as indicated, including balloon-injured arteries and uninjured contralateral arteries, were collected for imaging with an IVIS spectrum luminescence system (Ex/Em: 650/720 nm). Fluorescence intensity per mg tissue was quantified and the data are shown in FIG. 15C. The epi-fluorescence is fluorescence emission radiance per incident excitation intensity: $p/sec/cm^2/sr/\mu W/cm^2$ (sr=steradian).

Figure 1A:
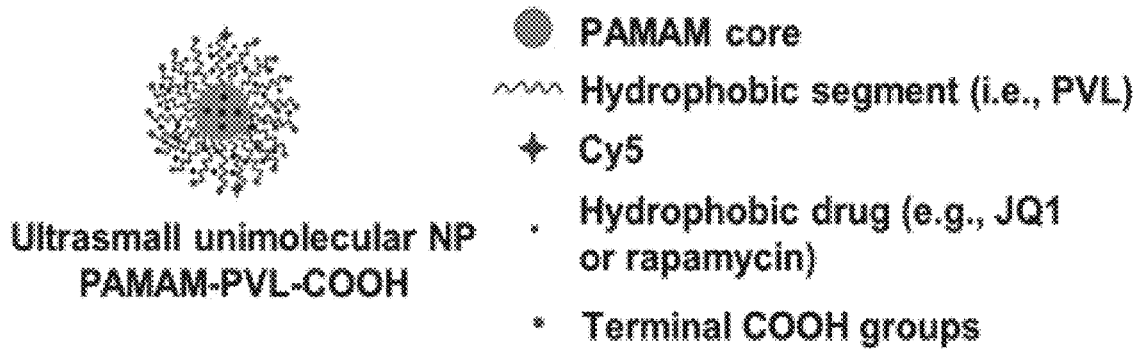
FIGS. 1A-1C show: a schematic illustration of a drug-loaded PAMAM-PVL ultrasmall unimolecular NP (FIG. 1A); an illustration for the preparation of a biomimetic nanocluster coated with membrane derived from platelet, peripheral blood mononuclear cell, mesenchymal stem cell, exosome, or macrophage (FIG. 1B); and a transmission electron microscopy (TEM) image of platelet membrane-coated nanoclusters (FIG. 1C). The inset of FIG. 1C shows an enlarged image of a single biomimetic platelet membrane-coated nanocluster.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Many modifications and other aspects disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific aspects disclosed and that modifications and other aspects are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual aspects described and illustrated herein has discrete components and features which may be readily separated from or combined with the features of any of the other several aspects without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Aspects of the present disclosure will employ, unless otherwise indicated, techniques of molecular biology, microbiology, organic chemistry, biochemistry, physiology, cell biology, blood vessel biology, and the like, which are within the skill of the art. Such techniques are explained fully in the literature.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Additionally, the term "comprising" is intended to include examples and aspects encompassed by the terms "consisting essentially of" and "consisting of." Similarly, the term "consisting essentially of" is intended to include examples encompassed by the term "consisting of".

As used in the specification and the appended claims, the singular forms "a," "an" and "the" include plural referents unless the context clearly dictates otherwise. Thus, for example, reference to "a unimolecular nanoparticle," "a nanocluster," or "a biomimetic vesicle," including, but not limited to, two or more such unimolecular nanoparticles, nanoclusters, or biomimetic vesicles, including combinations of unimolecular nanoparticles, nanoclusters, or biomimetic vesicles, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the terms "optional" or "optionally" means that the subsequently described event or circumstance can or cannot occur, and that the description includes instances where said event or circumstance occurs and instances where it does not.

As used herein, a "cardiovascular disease" is a disease, condition, or disorder that impacts the heart, circulatory system, or both the heart and the circulatory system. The circulatory system includes the cardiovascular system, and the lymphatic system. The lymphatic system distributes lymph. The cardiovascular system is a system of blood vessels, primarily arteries and veins, which transport blood to and from the heart, brain and peripheral organs such as, without limitation, the arms, legs, kidneys and liver. The coronary artery system supplies blood to the heart. The carotid artery system supplies blood to the brain. The peripheral vascular system carries blood to (via arteries) and from (via veins) the peripheral organs such as, without limitation, the hands, legs, kidneys and liver. The coronary artery system, carotid artery system, and the peripheral vascular system which includes the peripheral artery system are sub-systems of the cardiovascular system.

As used herein, a "vascular disease" generally refers to a disease, condition, or disorder that impacts the circulatory system. In particular "vascular disease" includes a disease, disorder, or condition of the coronary system, the carotid system and the peripheral vascular system.

"Vascular diseases" are a subset of "cardiovascular diseases."

Examples of cardiovascular diseases include diseases of the heart which include, but are not limited to, heart valve disease, arrhythmia, heart failure, and congenital heart disease, and vascular diseases which include, but are not limited to atherosclerosis, thrombosis, restenosis, hemorrhage, vascular dissection or perforation, vulnerable plaque, chronic total occlusion, claudication, anastomotic proliferation for vein and artificial grafts, peripheral artery disease, carotid artery disease, coronary artery disease, anueyrsm, renal (kidney) artery disease, raynaud's syndrome, buerger's disease, peripheral venous disease, varicose veins, blood clots in the veins, blood clotting disorders, and lymphdema.

As used herein, "administering" can refer to an administration that is oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g. by diffusion) a composition the perivascular space and adventitia. For example a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, "therapeutic agent" can refer to any substance, compound, molecule, and the like, which can be biologically active or otherwise can induce a pharmacologic, immunogenic, biologic and/or physiologic effect on a subject to which it is administered to by local and/or systemic action. A therapeutic agent can be a primary active agent, or in other words, the component(s) of a composition to which the whole or part of the effect of the composition is attributed. A therapeutic agent can be a secondary therapeutic agent, or in other words, the component(s) of a composition to which an additional part and/or other effect of the composition is attributed. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14th edition), the Physicians' Desk Reference (64th edition), and The Pharmacological Basis of Therapeutics (12th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, "attached" can refer to a covalent or non-covalent interaction between two or more molecules. Non-covalent interactions can include ionic bonds, electrostatic interactions, van der Walls forces, dipole-dipole interactions, dipole-induced-dipole interactions, London dispersion forces, hydrogen bonding, halogen bonding, electromagnetic interactions, $\pi$-$\pi$ interactions, cation-$\pi$ interactions, anion-$\pi$ interactions, polar $\pi$-interactions, and hydrophobic effects.

As used interchangeably herein, "subject," "individual," or "patient" can refer to a vertebrate organism, such as a mammal (e.g. human). "Subject" can also refer to a cell, a population of cells, a tissue, an organ, or an organism, preferably to human and constituents thereof.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as vascular endothelial injury, stenosis, and/or restenosis. The effect can be therapeutic in terms of a partial or complete cure of a disease, condition, symptom or adverse effect attributed to the disease, disorder, or condition. The term "treatment" as used herein can include any treatment of vascular endothelial injury, stenosis, and/or restenosis in a subject, particularly a human and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

As used herein, "dose," "unit dose," or "dosage" can refer to physically discrete units suitable for use in a subject, each unit containing a predetermined quantity of a disclosed unimolecular nanoparticles, nanoclusters, and/or biomimetic nanoclusters that contain a nanocluster described herein and/or a pharmaceutical formulation thereof calculated to produce the desired response or responses in association with its administration.

As used herein, "therapeutic" can refer to treating, healing, and/or ameliorating a disease, disorder, condition, or side effect, or to decreasing in the rate of advancement of a disease, disorder, condition, or side effect.

As used herein, "effective amount" can refer to the amount of a compound provided herein that is sufficient to effect beneficial or desired biological, emotional, medical, or clinical response of a cell, tissue, system, animal, or human. An effective amount can be administered in one or more administrations, applications, or dosages. The term can also include within its scope amounts effective to enhance or restore to substantially normal physiological function. The "effective amount" can refer to the amount of a unimolecular nanoparticle, nanocluster, or membrane vesicle containing a nanocluster described herein that can deliver a pharmaceutical agent to a subject, deliver a pharmaceutical agent to the vascular endothelium of injured arteries, facilitate re-endothelialization, reduce thrombogenic risk, treat a stenosis, and/or treat a restenosis.

As used herein, the term "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products.

As used herein, the term "prophylactically effective amount" refers to an amount effective for preventing onset or initiation of a disease or condition.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

The term "molecular weight", as used herein, can generally refer to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

The term "contacting" as used herein refers to bringing a disclosed unimolecular nanoparticles, nanoclusters, and/or biomimetic nanoclusters in proximity to a cell, a target protein, or other biological entity together in such a manner that the disclosed unimolecular nanoparticles, nanoclusters, and/or biomimetic nanoclusters can affect the activity of a cell, target protein, or other biological entity, either directly; i.e., by interacting with the cell, target protein, or other biological entity itself, or indirectly; i.e., by interacting with another molecule, co-factor, factor, or protein on which the activity of the cell, target protein, or other biological entity itself is dependent.

It is understood, that unless otherwise specified, temperatures referred to herein are based on atmospheric pressure (i.e. one atmosphere).

Described herein are biomimetic vesicles that can contain a nanocluster that can include unimolecular nanoparticles that can be loaded with one or more compounds, such as pharmaceutical compounds. These biomimetic vesicles can be used to deliver one or more compounds, such as a pharmaceutical agent(s), to a tissue, such as the endothelium of a blood vessel. In some aspects, the biomimetic vesicles can be configured to target particular tissue type, such as the endothelium of a blood vessel. Also described herein are methods of synthesizing the biomimetic vesicles nanoparticles. Also described herein are methods of administering the biomimetic vesicles that can include one or more compounds, such as a pharmaceutical compound, to a subject in need thereof. In some aspects, the subject can have a stenosis. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Unimolecular Nanoparticles.

Figure 1B:
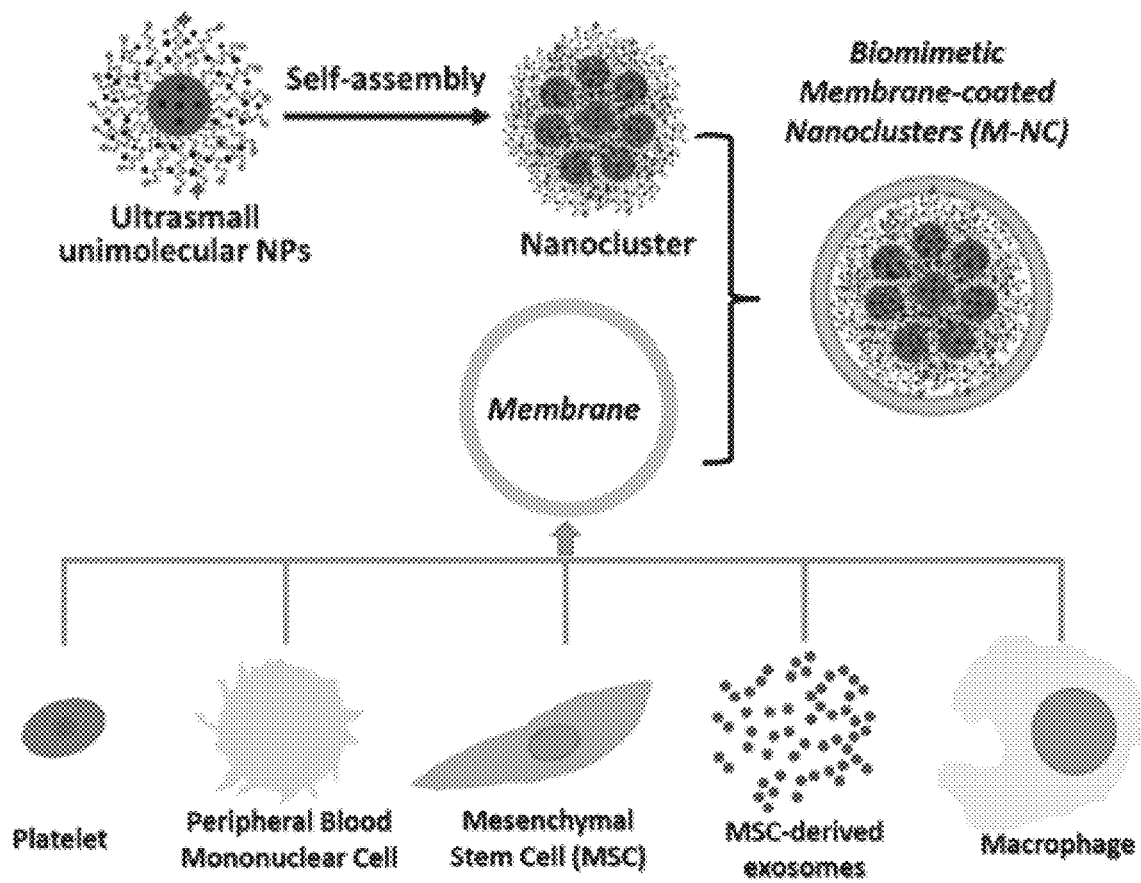

Described herein are unimolecular nanoparticles that can be loaded with a pharmaceutical agent and can self-assemble into a core-shell nanoparticle. These unimolecular nanoparticles can be used to form nanoclusters, which in turn can be encapsulated by platelet membrane vesicles. The unimolecular core-shell nanoparticles can contain a functionalized polymer, wherein the functionalized polymer can include a core-forming segment and a shell-forming segment. FIGS. 1A-1B shows various aspects of a unimolecular nanoparticle having a core shell configuration and incorporation into nanoclusters and platelet membrane vesicles. The functionalized polymer can be configured to form unimolecular core-shell nanoparticles.

The core-forming segment can be a dendrimer or a hyperbranched polymer. The core-forming segment can be a dendrimer selected from the group of a bis-MPA dendrimer; a dendron, a PMAMAM dendrimer, a PEG-core dendrimer, a phosphorous dendrimer, and a polypropylenimine dendrimer. Non-limiting examples of bis-MPA dendrimers can include acetylene functionalized bis-MPA dendrimers (e.g. any generation bis-MPA-Acetylene dendrimer trimethylol propane core), azide functionalized bis-MPA dendrimers (e.g. any generation bis-MPA-Azide dendrimer trimethylol popane core), carboxylic acid functionalized bis-MPA dendrimers (e.g. any generation bis-MPA-COOH dendrimer trimethylol propane core), and hydroxyl functionalized bis- MPA dendrimers (e.g. any generation bis-MPA-OH dendrimer trimethylol propane core). The core-forming segment can be a generation 1, 2, 3, 4, 5, 6, 7, 8, 9, or 10 generation dendrimer or hyperbranched polymer.

Non-limiting examples of dendrons can include polyester bis-MPA dendron, 16 carboxyl, 1 amine generation 4, polyester bis-MPA dendron, 16 hydroxyl, 1 allyl generation 4, polyester bis-MPA dendron, 16 hydroxyl 1 amine generation 4, polyester bis-MPA dendron 16, hydroxyl, 1 azide generation 4, polyester bis-MPA dendron 16 hydroxyl, 1 thiol generation 4, polyester bis-MPA dendron, 2 hydroxyl, 1 acetylene generation 1, polyester bis-MPA dendron, 2 hydroxyl, 1 azide generation 1, polyester bis-MPA dendron, 32 carboxyl, 1 amine generation 5, polyester bis-MPA dendron, 32 hydroxyl, 1 allyl generation 5, polyester bis-MPA dendron, 32 hydroxyl, 1 amine generation 5, polyester bis-MPA dendron, 32 hydroxyl, 1 azide generation 5, polyester bis-MPA dendron, 32 hydroxyl, 1 thiol generation 5, polyester bis-MPA dendron, 4 hydroxyl, 1 acetylene generation 2, polyester bis-MPA dendron, 4 hydroxyl, 1 azide generation 2, polyester bis-MPA dendron, 8 carboxyl, 1 amine generation 3, polyester bis-MPA dendron, 8 hydroxyl, 1 allyl generation 3, polyester bis-MPA dendron, 8 hydroxyl amine generation 3, polyester bis-MPA dendron, 8 hydroxyl, 1 azide generation 3, polyester bis-MPA dendron, 8 hydroxyl, 1 thiol generation 3, polyester-16-hydroxyl-1-carboxyl-acetylene bis-MPA dendron, generation 4, polyester-16-hydroxyl-1-carboxyl bis-MPA dendron generation 4, polyester-32-hydroxyl-1-carboxyl bis-MPA dendron generation 5, polyester-32-hydroxyl-1-acetylene bis-MPA dendron, generation 5, polyester-8-hydroxyl-1-acetylene bis-MPA dendron generation 3, and polyester-8-hydroxyl-1-carboxyl bis-MPA dendron generation 3.

Non-limiting examples of hyperbranched polymers can include generations 2, 3, 4, 5, and 6 hyperbranched PEG10k-OH, generations 2, 3, 4, 5, and 6 hyperbranched G2-PEG20k-OH, and generations 4, 5, and 6 hyperbranched PEG6k-OH.

Suitable PAMAM dendrimers can include, without limitation, those with a ethylenediamine core, a 1,4-diaminobutane core, a 1,6-diaminohexane cores, a 1,12-diaminododecane core, and a cystamine core. Suitable PAMAM dendrimers can include, without limitation, those with amidoethanol surface groups, amidoethylethanolamine surface groups, amino surface groups, hexylamide surface groups, bi-functional surface groups, sodium carboxylate surface groups, succinamic acid surface groups, trimethoxysilyl surface groups, tris(hydroxymethyl)amidomethane surface groups, and 3-carbomethoxypyrrolidinone surface groups. The PAMAM dendrimers can be generation 1, 2, 3, 4, 5, 6, 7, 8, 9, or 10 PAMAM dendrimers. The number of terminal functional groups on the PAMAM dendrimer can range from 2 to 512 or more.

Non-limiting examples of PEG-core dendrimers can include poly(ethylene glycol), 4 hydroxyl dendron generation 1 average $M_n$ 20,300, poly(ethylene glycol), 4 hydroxyl dendron generation 1 average $M_n$ 6,300, poly(ethylene glycol), 16 hydroxyl dendron generation 3 average $M_n$ 21,600, poly(ethylene glycol), 16 hydroxyl dendron generation 3 average $M_n$ 8,000, poly(ethylene glycol), 16 acetylene dendron generation 3 average $M_n$ 21,600, poly(ethylene glycol), 16 hydroxyl dendron generation 3 average $M_n$ 8,000, poly (ethylene glycol), 16 acetylene dendron generation 3 average $M_n$ 22,000, poly(ethylene glycol), 16 acetylene dendron generation 3 average $M_n$ 8,000, poly(ethylene glycol), 32 hydroxyl dendron generation 4 average $M_n$ 24,000, 32 hydroxyl dendron generation 4 average $M_n$ 9,500, 4 acetylene dendron generation 1 average $M_n$ 6,300, 4 acetylene dendron generation 1 average $M_n$ 20,000, 8 acetylene dendron generation 2 average $M_n$ 21,000, and 8 hydroxyl dendron generation 2 average $M_n$ 21,000.

Non-limiting examples of phosphorous dendrimers can include cyclotriphosphazene-PMMH-6 dendrimer, generation 1, phosphonitirilcic chloride trimer, thiophosphoryl chloride, thiophosphoryl-PMMH-12 dendrimer, generation 2.5, thiophosphoryl-PMMH-24 dendrimer, generation 3.5, and thiophosphoryl-PMMH-48 dendrimer, generation 5.0.

Non-limiting examples of polypropylenimine dendrimer can include DAB-Am-4, polypropylenimine tetramine dendrimer, generation 1.

Non-limiting examples of hyperbranched polymers can include hyperbranched bis-M PA polyesters (e.g. hyperbranched bis-MPA polyester-16-hydroxyl, generation 2, hyperbranched bis-MPA polyester-32-hydroxyl, generation 3, hyperbranched bis-MPA polyester-64-hydroxyl, generation 4), H20, H30, and H40 hyperbranched polymers, and hyperbranched polyglycerol.

In some aspects, the core-forming segment can be a PAMAM dendrimer. In some aspects the core-forming segment can be a generation 4 PAMAM dendrimer.

The shell-forming segment can be a polymer selected from the group of a polyester, a polyamide, polyanhydride, polycarbonate, and permissible co-polymers thereof. The shell-forming segment can be a polyester selected from the group of poly(valerolactone) (PVL), PLA, PLGA, PGA, PCL and co-polymers thereof. In some aspects, shell-forming segment can be polyvalerolactone.

The polymer can be functionalized with terminal negatively charged groups. The polymer polymer can be functionalized with terminal —COOH, —SO$_3$H, or —OPO$_3$H$_2$ groups, or a combination of groups thereof.

In some aspects, the functionalized polymer is PAMAM-PVL-COOH.

The core-forming polymer and the shell-forming polymer can be hydrophobic. In some aspects, the shell-forming polymer can be more hydrophobic relative to the core-forming polymer.

The unimolecular core-shell nanoparticle can further include a pharmaceutical agent. In some aspects the pharmaceutical agent can be a hydrophobic pharmaceutical agent. The pharmaceutical agent can be attached to the core-forming polymer, the shell-forming polymer, or both the core-forming polymer and the shell-forming polymer. In some aspects the pharmaceutical agent can reduce blood vessel injury. In some aspects, pharmaceutical agent can be JQ1, GSK2606414, and/or rapamycin. Other non-limiting examples of pharmaceutical agents include paclitaxel, GSK2656157, RVX-208, ARV-825, I-BET 762, OTX-015, CPI-203, CPI-0610, everolimus, zotarolimus, TEN-010, resveratrol, halofuginone, idarubicin, PIK75, and cyclopentenyl cytosine.

The diameter of a biomimetic nanoparticle can range from about 1-1000 nm, 1-900 nm, 1-800 nm, 1-700 nm, 1-600 nm, 1-500 nm, 1-400 nm, 1-300 nm, 1-200 nm, 1-100 nm, 1-50 nm, 1-40 nm, 1-30 nm, 1-20 nm, 1-10 nm, or 1-5 nm. In a further aspect, the diameter of a biomimetic nanoparticle can range from about 10-1000 nm, 10-900 nm, 10-800 nm, 10-700 nm, 10-600 nm, 10-500 nm, 10-400 nm, 10-300 nm, 10-200 nm, 10-100 nm, 10-50 nm, 10-40 nm, 10-30 nm, or 10-20 nm. In a still further aspect, the diameter of a biomimetic nanoparticle can range from about 50-1000 nm, 50-900 nm, 50-800 nm, 50-700 nm, 50-600 nm, 50-500 nm, 50-400 nm, 50-300 nm, 50-200 nm, or 50-100 nm.

The unimolecular nanoparticles can be formed by first forming the functionalized polymer. The core-forming segment as a macroinitiator for ring-opening polymerization of the shell-forming segment. Once the functionalized polymer is formed it can associate with the core-forming segment to form the core and the shell-forming segments to form the shell. The resulting functionalized polymers can be lyophilized. The pharmaceutical agent can be loaded into the unimolecular nanoparticles by dissolving the functionalized polymer and the pharmaceutical agent(s) in a suitable solvent (e.g. DMSO). Water can be added dropwise into the solution over a suitable period of time (e.g. about 30 min). Un-loaded pharmaceutical agents and DMSO can be removed by dialysis against water for a suitable amount of time (e.g. about 48 h). The loaded nanoparticles can be lyophilized.

In some aspects wherein the core-forming segment was PAMAM (generation 4) having 64 —OH terminals and the shell-forming segment is polyvalerolactone, PAMAM can act as the macroinitiator for ring-opening of the shell-forming segment to form PAMAM-PVL-COOH. In some aspects, the average repeat unit of the PVL segment is 26. About 33 PVL "arms" per PAMAM-PVL-COOH can be present. In some aspects, a unimolecular nanoparticle containing PAMAM-PVL-COOH can have a diameter of about 18 nm. The relative proportion of protons in PVL and protons in PAMAM can be about 6.2:1. The weight ratio between PVL arms and PAMAM core can be about 6.0:1. The molecular weight of PAMAM-PVL-COOH can be about 102,037 g/mol ($M_n$, PDI=1.44).

The disclosed unimolecular nanoparticles can further comprise a therapeutic agent. In a further aspect, the therapeutic agent comprises a first therapeutic agent or a first therapeutic agent and a second therapeutic agent. The first pharmaceutical agent can be a hydrophobic pharmaceutical agent. In some cases, the second pharmaceutical agent can be a hydrophobic pharmaceutical agent.

In a further aspect, the first pharmaceutical agent inhibits smooth muscle cell proliferation. Exemplary, but not limiting, smooth muscle cell proliferation inhibitors are bromo and extraterminal (BET) protein inhibitors, protein kinase RNA-like endoplasmic reticulum kinase (PERK) inhibitors, PI3K/p110α inhibitors, CTPS1 inhibitors, EZH2 inhibitors, Smad3 inhibitors, PDGFR inhibitors, TGFBR inhibitors, derivatives thereof, pharmaceutically acceptable salts thereof, or any combination thereof. Further exemplary, but non-limiting, smooth muscle cell proliferation inhibitors include rapamycin, sirolimus, paclitaxel, halofuginone, idarubicin, derivatives thereof, pharmaceutically acceptable salts thereof, or any combination thereof.

In a further aspect, the bromo and extraterminal (BET) protein inhibitor is JQ1, RVX208, RO6870810, FT-1101, CPI-0610, ZEN-3694, GSK525762, MK-8628, BMS-986158, INCB054329, RVX297, a derivative thereof, a pharmaceutically acceptable salt thereof, or any combination thereof.

In a further aspect, the protein kinase RNA-like endoplasmic reticulum kinase (PERK) inhibitor is GSK2606414, GSK2656157, AMG PERK 44, a derivative thereof, a pharmaceutically acceptable salt thereof, or any combination thereof.

In a further aspect, the PI3K/p110α inhibitor, CTPS1 inhibitor, EZH2 inhibitor, Smad3 inhibitor, PDGFR inhibitor, and a TGFBR inhibitor is UNC1999, tubastatin-A, SIS3, imatinib, SB431542, cyclopentyl cytosine, a derivative thereof, a pharmaceutically acceptable salt thereof, or any combination thereof.

In various aspects, the second pharmaceutical agent can be an anti-inflammatory agent, an anti-thrombogenic agent, a lipid lowering agent with endothelium protection function, an anti-hypertensive agent, other epigenetic inhibitors, or any combination thereof. Exemplary, but not limiting, anti-inflammatory agents are diflusinal, ibuprofen, naproxen, ketoprofen, fenoprofen, flurbiprofen, fenbufen, benoxaprofen, tiaprofenic acid, indoprofen, suprofen, etodolac, zomepirac, indomethacin, alclofenac, sulindac, fenclofenac, diclofenac, tolmetin, mefanamic acid, phenylbutazone, oxyphenbuta, azapropazone, feprazone, piroxicam, derivatives thereof, pharmaceutically acceptable salts thereof, or any combination thereof. Anti-thrombogenic agents are heparin, warfarin, clopidogrel, derivatives thereof, pharmaceutically acceptable salts thereof, or any combination thereof. Lipid lowering agents are atorvastatin, lovastatin, REGN727, AMG 145, derivatives thereof, pharmaceutically acceptable salts thereof, or any combination thereof. Anti-hypertensive agents include lorsartan, ramipril, benazipril, verapamil, nifedipine, propranolol, bucindolol, aliskiren, bosentan, derivatives thereof, pharmaceutically acceptable salts thereof, or any combination thereof. Other epigenetic inhibitors include SAHA, belinostat, vorinostat, 5 azacytidine, trichostatin A, EPZ-5676, UNC-1999, 5 azacytidine.

Nanoclusters.

Also described herein are nanoclusters that can contain a plurality of unimolecular core-shell nanoparticles as described herein. FIG. 1B shows aspects of a nanocluster that can contain a plurality of unimolecular core-shell nanoparticles. The plurality of nanoparticles can be homogeneous (i.e. contains all the same unimolecular core-shell nanoparticles). The plurality of nanoparticles can be heterogeneous (i.e. the plurality of unimolecular core-shell nanoparticles contains at least two different unimolecular core-shell nanoparticles). In various aspects, the average diameter of the biomimetic nanoclusters can range from about 50 nm to about 400 nm, including any value or sub-range of values therein. In a further aspect, the average diameter of the biomimetic nanoclusters can range from about 50 nm to about 200 nm, including any value or sub-range of values therein. In a still further aspect, the average diameter of the biomimetic nanoclusters can range from about 100 nm to about 200 nm, including any value or sub-range of values therein. In some aspects the average diameter of the nanoclusters is about 100 nm, about 101 nm, about 102 nm, about 103 nm, about 104 nm, about 105 nm, about 106 nm, about 107 nm, about 108 nm, about 109 nm, about 110 nm, about 111 nm, about 112 nm, about 113 nm, about 114 nm, about 115 nm, about 116 nm, about 117 nm, about 118 nm, about 119 nm, about 120 nm, about 121 nm, about 122 nm, about 123 nm, about 124 nm, about 125 nm, about 126 nm, about 127 nm, about 128 nm, about 129 nm, about 130 nm, about 131 nm, about 132 nm, about 133 nm, about 134 nm, about 135 nm, about 136 nm, about 137 nm, about 138 nm, about 139 nm, about 140 nm, about 141 nm, about 142 nm, about 143 nm, about 144 nm, about 145 nm, about 146 nm, about 147 nm, about 148 nm, about 149 nm, about 150 nm, about 151 nm, about 152 nm, about 153 nm, about 154 nm, about 155 nm, about 156 nm, about 157 nm, about 158 nm, about 159 nm, about 160 nm, about 161 nm, about 162 nm, about 163 nm, about 164 nm, about 165 nm, about 166 nm, about 167 nm, about 168 nm, about 169 nm, about 170 nm, about 171 nm, about 172 nm, about 173 nm, about 174 nm, about 175 nm, about 176 nm, about 177 nm, about 178 nm, about 179 nm, about 180 nm, about 181 nm, about 182 nm, about 183 nm, about 184 nm, about 185 nm, about 186 nm, about 187 nm, about 188 nm, about 189 nm, about 190 nm, about 191 nm, about 192 nm, about 193 nm, about 194 nm, about 195 nm, about 196 nm, about 197 nm, about 198 nm, about 199 nm, about 200 nm, or any range encompassed by any two of the foregoing values, or any group or set of the foregoing values. It will be appreciated that the diameter of the nanocluster will be a function of the diameter and number of the unimolecular nanoparticles contained therein.

In various aspects, the number of unimolecular core-shell nanoparticles in the plurality of unimolecular core-shell nanoparticles can range from about 20 to about 10,000, or any value or range of values therein. In a further aspect, the number of unimolecular core-shell nanoparticles in the plurality of unimolecular core-shell nanoparticles can range from about 20 to about 1,500, or any value or range of values therein. In a still further aspect, the number of unimolecular core-shell nanoparticles in the plurality of unimolecular core-shell nanoparticles can range from about 150 to about 1,500, or any value or range of values therein.

In various aspects, the disclosed nanoclusters can have a negative zeta potential. In a further aspect, the disclosed nanoclusters have a zeta potential of about −10 mV to about −50 mV. In a still further aspect, the disclosed nanoclusters have a zeta potential of about −15 mV to about −45 mV. In a yet further aspect, the disclosed nanoclusters have a zeta potential of about −20 mV to about −40 mV. In an even further aspect, the disclosed nanoclusters have a zeta potential of about −25 mV to about −35 mV. In a still further aspect, the disclosed nanoclusters have a zeta potential of about −10 mV, about −11 mV, about −12 mV, about −13 mV, about −14 mV, about −15 mV, about −16 mV, about −17 mV, about −18 mV, about −19 mV, about −20 mV, about −21 mV, about −22 mV, about −23 mV, about −24 mV, about −25 mV, about −26 mV, about −27 mV, about −28 mV, about −29 mV, about −30 mV, about −31 mV, about −32 mV, about −33 mV, about −34 mV, about −35 mV, about −36 mV, about −37 mV, about −38 mV, about −39 mV, about −40 mV, about −41 mV, about −42 mV, about −43 mV, about −44 mV, about −45 mV, about −46 mV, about −47 mV, about −48 mV, about −49 mV, about −50 mV, or any range encompassed by the foregoing values, or a set or group of the foregoing values.

In various aspects, the disclosed nanoclusters have a drug loading level (on a weight basis) of about 5% to about 50%. In a further aspect, the disclosed nanoclusters have a drug loading level (on a weight basis) of about 10% to about 40%. In a yet further aspect, the disclosed nanoclusters have a drug loading level (on a weight basis) of about 20% to about 30%. In some aspects, up to a 21% drug loading level in the nanoclusters can be achieved. In some aspects the drug loading efficiency in the nanoclusters can be up to 84% or more.

The nanoclusters can be formed via self-assembly of a plurality of unimolecular nanoparticles in an aqueous solution described herein. The unimolecular nanoparticles can be dispersed in an aqueous solution and form nanoclusters after sonication with a suitable period of time (e.g. about 2 min).

Biomimetic Nanoclusters.

Also described herein are biomimetic nanoclusters comprising a membrane structure comprising a first membrane component and a core structure comprising a disclosed nanocluster, herein referred to as coated nanoclusters. The first membrane component can encapsulate the one or more nanoclusters. In various aspects, the average diameter of the coated biomimetic nanoclusters can range from about 50 nm to about 400 nm, including any value or sub-range of values therein. In a further aspect, the average diameter of the biomimetic nanoclusters can range from about 50 nm to about 200 nm, including any value or sub-range of values therein. In a still further aspect, the average diameter of the biomimetic nanoclusters can range from about 100 nm to about 200 nm, including any value or sub-range of values therein.

The disclosed coated biomimetic nanoclusters can target the vascular endothelium. In some aspects the vesicle specifically target injured or aneurysmal vascular endothelium. The targeting can be accomplished via the inclusion of a cell-derived membrane vesicle prepared from an appropriate cell, e.g., platelets, peripheral blood mononuclear cells, mesenchymal stem cells, and macrophages, which is capable of "homing" to the vascular endothelium, particularly injured or aneurysmal vascular endothelium. Further, the cell-derived membrane vesicle can make the nanoparticles and/or nanoclusters dispersible in an aqueous solution. The disclosed biomimetic nanoclusters can be prepared by sonicating a disclosed nanocluster with a cell-derived membrane vesicle or a mesenchymal stem cell-derived exosome. The disclosed biomimetic nanoclusters can also be prepared by extrusion of the mixture of a disclosed nanocluster with a cell-derived membrane vesicle or a mesenchymal stem cell-derived exosome membrane, using a mini extruder with a membrane with a suitable pore size (e.g. 50, 100, and 200 nm).

The first membrane component can be derived from a cell-derived membrane vesicle prepared from an appropriate cell, e.g., platelets, peripheral blood mononuclear cells, mesenchymal stem cells, and macrophages. The cell-derived membrane vesicle can be prepared using conventional methods. In various aspects, the cell-derived membrane vesicle can be prepared by conventional methods from a mesenchymal stem cell, a peripheral blood mononuclear cell, a platelet, a macrophage, or any combination thereof. In some aspects, the mesenchymal stem cell can be obtained from a human donor source, a MHC-matched iPSC-derived MSC, or a combination thereof. The peripheral blood mononuclear cell used to prepare the cell-derived membrane vesicle can be obtained from a human donor source, a MHC-matched iPSC-derived peripheral blood mononuclear cell, or a combination thereof. The platelet used to prepare the cell-derived membrane vesicle can be obtained from a human donor source, a MHC-matched iPSC-derived peripheral platelet, or a combination thereof. The macrophage used to prepare the cell-derived membrane vesicle can be obtained from a human donor source, a MHC-matched iPSC-derived macrophage, or a combination thereof. Alternatively, a mesenchymal stem cell-derived exosome can be used in the preparation of the disclosed biomimetic nanoclusters. Mesenchymal stem cell-derived exosomes can be prepared from a human donor source, a MHC-matched iPSC-derived MSC, or a combination thereof by conventional methods.

In various aspects, the coated nanoclusters comprise a weight ratio of nanoparticle weight to a disclosed cell-derived membrane vesicle or exosome weight. In some aspects, the weight of a disclosed cell-derived membrane vesicle or exosome is based on the protein content in the disclosed cell-derived membrane vesicle or exosome. In a further aspect, the coated nanoclusters comprise a weight ratio of nanoparticle weight to a disclosed cell-derived membrane vesicle or exosome weight based on the amount of protein wherein the weight ratio is about 1:0.2 to about 1:10, or a weight ratio within the foregoing weight ratio range, or a value or set of values within the foregoing weight ratio range. In a still further aspect, the coated nanoclusters comprise a weight ratio of nanoparticle weight to a disclosed cell-derived membrane vesicle or exosome weight based on the amount of protein wherein the weight ratio is about 1:0.5 to about 1:4, or a weight ratio within the foregoing weight ratio range, or a value or set of values within the foregoing weight ratio range. In a yet further aspect, the coated nanoclusters comprise a weight ratio of nanoparticle weight to a disclosed cell-derived membrane vesicle or exosome weight based on the amount of protein wherein the weight ratio is about 1:1 to about 1:2, or a weight ratio within the foregoing weight ratio range, or a value or set of values within the foregoing weight ratio range.

Pharmaceutical Formulations Containing the Biomimetic Vesicles.

Also provided herein are pharmaceutical formulations that can include an amount of unimolecular nanoparticles, nanoclusters, and/or biomimetic vesicles described herein can be formulated and a pharmaceutical carrier appropriate for administration to a subject. The subject can be a subject in need thereof. The individual in need thereof can have or can be suspected of having a stenosis, restenosis, a vascular endothelial injury, or a symptom thereof. The pharmaceutical formulations can include an amount of unimolecular nanoparticles, nanoclusters, and/or biomimetic vesicles described herein described herein that can be effective to treat stenosis, restenosis, a vascular endothelial injury, or a symptom thereof. The unimolecular nanoparticles, nanoclusters, and/or biomimetic vesicles described herein, in some aspects, can be included in the manufacture of a medicament for treatment of a stenosis, restenosis, vascular endothelial injury or a symptom thereof. Formulations can be administered via any suitable administration route. For example, the formulations (and/or compositions) can be administered to the subject in need thereof orally, intravenously, intramuscularly, intravaginally, intraperitoneally, rectally, parenterally, topically, intranasally, perivascularly, or subcutaneously. Other suitable routes are described elsewhere herein.

Parenteral Pharmaceutical Formulations Containing the Biomimetic Vesicles.

The unimolecular nanoparticles, nanoclusters, and/or biomimetic vesicles described herein can be formulated for parenteral delivery, such as injection or infusion, in the form of a solution or suspension. The formulation can be administered via any route, such as, the blood stream or directly to the organ or tissue to be treated.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of unimolecular nanoparticles, nanoclusters, and/or biomimetic vesicles described herein can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants can be anionic, cationic, amphoteric or nonionic surface active agents. Suitable anionic surfactants include, but are not limited to, those containing carboxylate, sulfonate and sulfate ions. Suitable anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Suitable cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Suitable nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-8-alanine, sodium N-lauryl-8-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation can also contain an antioxidant to prevent degradation of unimolecular nanoparticles, nanoclusters, and/or biomimetic vesicles described herein.

The formulation can be buffered to a pH of 3-8 for parenteral administration upon reconstitution. Suitable buffers include, but are not limited to, phosphate buffers, acetate buffers, and citrate buffers.

Water-soluble polymers can be used in the formulations for parenteral administration. Suitable water-soluble polymers include, but are not limited to, polyvinylpyrrolidone, dextran, carboxymethylcellulose, and polyethylene glycol. Sterile injectable solutions can be prepared by incorporating unimolecular nanoparticles, nanoclusters, and/or biomimetic vesicles described herein in the required amount in the appropriate solvent or dispersion medium with one or more of the excipients listed above, as required, followed by filtered sterilization. Dispersions can be prepared by incorporating the various sterilized unimolecular nanoparticles, nanoclusters, and/or biomimetic vesicles described herein into a sterile vehicle which contains the basic dispersion medium and the required other ingredients from those listed above. Sterile powders for the preparation of sterile injectable solutions can be prepared by vacuum-drying and freeze-drying techniques, which yields a powder of unimolecular nanoparticles, nanoclusters, and/or biomimetic vesicles described herein plus any additional desired ingredient from a previously sterile-filtered solution thereof. The powders can be prepared in such a manner that the particles are porous in nature, which can increase dissolution of the particles. Methods for making porous particles are well known in the art.

Pharmaceutical formulations for parenteral administration can be in the form of a sterile aqueous solution or suspension of particles formed from unimolecular nanoparticles, nanoclusters, and/or biomimetic vesicles described herein. Acceptable solvents include, for example, water, Ringer's solution, phosphate buffered saline (PBS), and isotonic sodium chloride solution. The formulation can also be a sterile solution, suspension, or emulsion in a nontoxic, parenterally acceptable diluent or solvent such as 1,3-butanediol.

In some instances, the formulation can be distributed or packaged in a liquid form. In other aspects, formulations for parenteral administration can be packed as a solid, obtained, for example by lyophilization of a suitable liquid formulation. The solid can be reconstituted with an appropriate carrier or diluent prior to administration.

Solutions, suspensions, or emulsions for parenteral administration can be buffered with an effective amount of buffer necessary to maintain a pH suitable for ocular administration. Suitable buffers include, but are not limited to, acetate, borate, carbonate, citrate, and phosphate buffers.

Solutions, suspensions, or emulsions for parenteral administration can also contain one or more tonicity agents to adjust the isotonic range of the formulation. Suitable tonicity agents include, but are not limited to, glycerin, mannitol, sorbitol, sodium chloride, and other electrolytes.

Solutions, suspensions, or emulsions for parenteral administration can also contain one or more preservatives to prevent bacterial contamination of the ophthalmic preparations. Suitable preservatives include, but are not limited to, polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions, use of nanotechnology including nanoformulations for parenteral administration can also contain one or more excipients, such as dispersing agents, wetting agents, and suspending agents.
Enteral Pharmaceutical Formulations Containing the Biomimetic Vesicles.

The unimolecular nanoparticles, nanoclusters, and/or biomimetic vesicles described herein can be prepared in enteral formulations, such as for oral administration. Suitable oral dosage forms include tablets, capsules, solutions, suspensions, syrups, and lozenges. Tablets can be made using compression or molding techniques well known in the art. Gelatin or non-gelatin capsules can be prepared as hard or soft capsule shells, which can encapsulate liquid, solid, and semi-solid fill materials, using techniques well known in the art.

Formulations containing unimolecular nanoparticles, nanoclusters, and/or biomimetic vesicles described herein can be prepared using pharmaceutically acceptable carriers. As generally used herein "carrier" includes, but is not limited to, diluents, preservatives, binders, lubricants, disintegrators, swelling agents, fillers, stabilizers, and combinations thereof. Polymers used in the dosage form include, but are not limited to, suitable hydrophobic or hydrophilic polymers and suitable pH dependent or independent polymers. Suitable hydrophobic and hydrophilic polymers include, but are not limited to, hydroxypropyl methylcellulose, hydroxypropyl cellulose, hydroxyethyl cellulose, carboxy methylcellulose, polyethylene glycol, ethylcellulose, microcrystalline cellulose, polyvinyl pyrrolidone, polyvinyl alcohol, polyvinyl acetate, and ion exchange resins. "Carrier" also includes all components of the coating composition which can include plasticizers, pigments, colorants, stabilizing agents, and glidants.

Formulations containing unimolecular nanoparticles, nanoclusters, and/or biomimetic vesicles described herein can be prepared using one or more pharmaceutically acceptable excipients, including diluents, preservatives, binders, lubricants, disintegrators, swelling agents, fillers, stabilizers, and combinations thereof.

Delayed release dosage formulations containing unimolecular nanoparticles, nanoclusters, and/or biomimetic vesicles described herein as described herein can be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, M D, 2000, and "Pharmaceutical dosage forms and drug delivery systems", 6th Edition, Ansel et al., (Media, PA: Williams and Wilkins, 1995). These references provide information on excipients, materials, equipment and process for preparing tablets and capsules and delayed release dosage forms of tablets, capsules, and granules. These references provide information on carriers, materials, equipment and process for preparing tablets and capsules and delayed release dosage forms of tablets, capsules, and granules.

The formulations containing unimolecular nanoparticles, nanoclusters, and/or biomimetic vesicles described herein can be coated with a suitable coating material, for example, to delay release once the particles have passed through the acidic environment of the stomach. Suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings can be formed with a different ratio of water soluble polymer, water insoluble polymers and/or pH dependent polymers, with or without water insoluble/water soluble non polymeric excipient, to produce the desired release profile. The coating can be performed on a dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Additionally, the coating material can contain conventional carriers such as plasticizers, pigments, colorants, glidants, stabilization agents, pore formers and surfactants. Optional pharmaceutically acceptable excipients include, but are not limited to, diluents, binders, lubricants, disintegrants, colorants, stabilizers, and surfactants.

Diluents, also referred to as "fillers," can be used to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicon dioxide, titanium oxide, magnesium aluminum silicate and powdered sugar. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful.

Binders can impart cohesive qualities to a solid dosage formulation, and thus can ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders.

Lubricants can be included to facilitate tablet manufacture. Suitable lubricants include, but are not limited to, magnesium stearate, calcium stearate, stearic acid, glyceryl behenate, polyethylene glycol, talc, and mineral oil. A lubricant can be included in a tablet formulation to prevent the tablet and punches from sticking in the die. The lubricant can be chosen from such slippery solids as talc, magnesium and calcium stearate, stearic acid and hydrogenated vegetable oils.

Disintegrants can be used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers can be used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

Topical Pharmaceutical Formulations Containing the Biomimetic Vesicles.

The unimolecular nanoparticles, nanoclusters, and/or biomimetic vesicles described herein can be formulated for topical administration. Suitable dosage forms for topical administration include creams, ointments, salves, sprays, gels, lotions, emulsions, liquids, and transdermal patches. The formulation can be formulated for transmucosal, transepithelial, transendothelial, or transdermal administration. The topical formulations can contain one or more chemical penetration enhancers, membrane permeability agents, membrane transport agents, emollients, surfactants, stabilizers, and combination thereof.

In some aspects, unimolecular nanoparticles, nanoclusters, and/or biomimetic vesicles described herein can be administered as a liquid formulation, such as a solution or suspension, a semi-solid formulation, such as a lotion or ointment, or a solid formulation. The unimolecular nanoparticles, nanoclusters, and/or biomimetic vesicles described herein can be formulated as liquids, including solutions and suspensions, such as eye drops or as a semi-solid formulation, such as ointment or lotion for topical application to the skin, to the mucosa, such as the eye, to the vagina, or to the rectum.

The formulation can contain one or more excipients, such as emollients, surfactants, emulsifiers, penetration enhancers, and the like. Suitable emollients include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In some aspects, the emollients can be ethylhexylstearate and ethylhexyl palmitate.

Suitable surfactants include, but are not limited to, emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In some aspects, the surfactant can be stearyl alcohol.

Suitable emulsifiers include, but are not limited to, acacia, metallic soaps, certain animal and vegetable oils, and various polar compounds, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In some aspects, the emulsifier can be glycerol stearate.

Suitable classes of penetration enhancers include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocylic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols).

Suitable emulsions include, but are not limited to, oil-in-water and water-in-oil emulsions. Either or both phases of the emulsions can include a surfactant, an emulsifying agent, and/or a liquid non-volatile non-aqueous material. In some aspects, the surfactant can be a non-ionic surfactant. In other aspects, the emulsifying agent is an emulsifying wax. In further aspects, the liquid non-volatile non-aqueous material is a glycol. In some aspects, the glycol is propylene glycol. The oil phase can contain other suitable oily pharmaceutically acceptable excipients. Suitable oily pharmaceutically acceptable excipients include, but are not limited to, hydroxylated castor oil or sesame oil can be used in the oil phase as surfactants or emulsifiers.

Lotions containing unimolecular nanoparticles, nanoclusters, and/or biomimetic vesicles described herein are also provided. In some aspects, the lotion can be in the form of an emulsion having a viscosity of between 100 and 1000 centistokes. The fluidity of lotions can permit rapid and uniform application over a wide surface area. Lotions can be formulated to dry on the skin leaving a thin coat of their medicinal components on the skin's surface.

Creams containing unimolecular nanoparticles, nanoclusters, and/or biomimetic vesicles described herein are also provided. The cream can contain emulsifying agents and/or other stabilizing agents. In some aspects, the cream is in the form of a cream having a viscosity of greater than 1000 centistokes, typically in the range of 20,000-50,000 centistokes. Creams, as compared to ointments, can be easier to spread and easier to remove.

One difference between a cream and a lotion is the viscosity, which is dependent on the amount/use of various oils and the percentage of water used to prepare the formulations. Creams can be thicker than lotions, can have various uses, and can have more varied oils/butters, depending upon the desired effect upon the skin. In some aspects of a cream formulation, the water-base percentage can be about 60% to about 75% and the oil-base can be about 20% to about 30% of the total, with the other percentages being the emulsifier agent, preservatives and additives for a total of 100%.

Ointments containing unimolecular nanoparticles, nanoclusters, and/or biomimetic vesicles described herein and a suitable ointment base are also provided. Suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

Also described herein are gels containing unimolecular nanoparticles, nanoclusters, and/or biomimetic vesicles described herein, a gelling agent, and a liquid vehicle. Suitable gelling agents include, but are not limited to, modified celluloses, such as hydroxypropyl cellulose and hydroxyethyl cellulose; carbopol homopolymers and copolymers; thermoreversible gels and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents can be selected for their ability to dissolve the drug. Other additives, which can improve the skin feel and/or emolliency of the formulation, can also be incorporated. Such additives include, but are not limited, isopropyl myristate, ethyl acetate, $C_{12}$-$C_{15}$ alkyl benzoates, mineral oil, squalane, cyclomethicone, capric/caprylic triglycerides, and combinations thereof.

Also described herein are foams that can include unimolecular nanoparticles, nanoclusters, and/or biomimetic vesicles described herein as described herein. Foams can be an emulsion in combination with a gaseous propellant. The gaseous propellant can include hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or can become approved for medical use are suitable. The propellants can be devoid of hydrocarbon propellant gases, which can produce flammable or explosive vapors during spraying. Furthermore, the foams can contain no volatile alcohols, which can produce flammable or explosive vapors during use.

Buffers can be used to control pH of a composition. The buffers can buffer the composition from a pH of about 4 to a pH of about 7.5, from a pH of about 4 to a pH of about 7, or from a pH of about 5 to a pH of about 7. In some aspects, the buffer can be triethanolamine.

Preservatives can be included to prevent the growth of fungi and microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

In certain aspects, the formulations can be provided via continuous delivery of one or more formulations to a patient in need thereof. For topical applications, repeated application can be done or a patch can be used to provide continuous administration of the noscapine analogs over an extended period of time.

Additional Active Agents for Pharmaceutical Formulations Containing the Biomimetic Vesicles.

In some aspects, an amount of one or more additional active agents (e.g. in addition to those loaded in the unimolecular nanoparticles), can be included in the pharmaceutical formulation containing unimolecular nanoparticles, nanoclusters, and/or biomimetic vesicles described herein. Suitable additional active agents include, but are not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, anti-thrombogenics, lipid lowers, anti-hypertensives, epigenetic inhibitors, and chemotherapeutics. The unimolecular nanoparticles, nanoclusters, and/or biomimetic vesicles described herein can be used as a monotherapy or in combination with other active agents for treatment of metabolic disorder (diabetes, high-cholesterol, hyperlipidemia, high-triglycerides).

Methods of Using the Unimolecular Nanoparticles, Nanoclusters, and Biomimetic Vesicles.

The unimolecular nanoparticles, nanoclusters, and/or the biomimetic vesicles containing the nanoclusters described herein can be administered to a subject. In some aspects, the subject can be a subject in need thereof. In some aspects, a method can include the step of administering a unimolecular core-shell nanoparticle as described herein, a nanocluster as described herein, or a vesicle as described herein to a subject. The subject can have a stenosis or restenosis. The subject can have had or have a stent. The blood vessel endothelium in at least one area can be injured.

These unimolecular nanoparticles, nanoclusters, and/or vesicles described herein can be delivered via one or more injections or other suitable delivery routes, with varying dosing. In some aspects administration is intravenous. Administration of unimolecular nanoparticles, nanoclusters, biomimetic vesicles and/or formulations thereof described herein can be systemic or localized. The unimolecular nanoparticles, nanoclusters, biomimetic vesicles and/or formulations thereof described herein can be administered to the subject in need thereof one or more times per hour. The unimolecular nanoparticles, nanoclusters, biomimetic vesicles and/or formulations thereof described herein can be administered 1, 2, 3, 4, 5, 6 or more times per hour. The unimolecular nanoparticles, nanoclusters, biomimetic vesicles and/or formulations thereof described herein can be administered to the subject in need thereof one or more times per day. The unimolecular nanoparticles, nanoclusters, biomimetic vesicles and/or formulations thereof described herein can be administered once daily. The unimolecular nanoparticles, nanoclusters, biomimetic vesicles and/or formulations thereof described herein can be administered 2, 3, 4, 5, 6, 7, 8, 9, 10 or more times daily. When administered, an effective amount of the unimolecular nanoparticles, nanoclusters, biomimetic vesicles and/or formulations thereof described herein can be administered to the subject in need thereof. The compound(s) and/or formulation(s) thereof can be administered 1, 2, 3, 4, 5, 6, 7, 8, 9, 10 or more times per week. In some aspects, the unimolecular nanoparticles, nanoclusters, biomimetic vesicles and/or formulations thereof described herein can be administered 1 day per week. In other aspects, the unimolecular nanoparticles, nanoclusters, biomimetic vesicles and/or formulations thereof described herein can be administered 2 to 7 days per week. In some aspects the compound(s) and/or formulation(s) thereof can be administered 1, 2, 3, 4, 5, 6, 7, 8, 9, 10, 11, 12 or more times per month or per year. The formulations can be administered ad lib per determination of the skilled medical practitioner such as a physician, nurse practitioner, and/or physician assistant.

The unimolecular nanoparticles, nanoclusters, and/or biomimetic vesicles delivered to the subject in each injection can be the same or can be different. Thus, a subject can receive different types of pharmaceutical agents by delivery of a membrane vesicle containing nanoclusters that can contain more than one type of pharmaceutical agent or by being administered at least two injections of membrane vesicles, wherein the pharmaceutical agent contained in each nanocluster encapsulated in the membrane vesicle is different.

In some aspects the amount of the biomimetic vesicles containing a nanocluster described herein administered to the subject can be an effective amount. The effective amount can be administered over one or more injections or other suitable delivery methods. In some aspects, the amount administered is effective to reduce or eliminate injury to blood vessel endothelium, such as that resulting from restenosis treatments. The effective amount of unimolecular nanoparticles, nanoclusters, and/or biomimetic vesicles or formulations thereof described herein can range from about 0.1 mg/kg to about 500 mg/kg. In some aspects, the effective amount ranges from about 0.1 mg/kg to 10 mg/kg. In additional aspects, the effective amount ranges from about 100 mg/kg. If further aspects, the effective amount ranges from about 0.1 mg to about 1000 mg. In some aspects, the effective amount can be about 500 mg to about 1000 mg.

In various aspects, the method of treatment comprises administering disclosed unimolecular nanoparticles, nanoclusters, and/or biomimetic vesicles or formulations thereof to treat a subject diagnosed with a cardiovascular disease and/or a cardiovascular injury. In some cases, the cardiovascular disease is a vascular disease. In various aspects, the vascular disease is stenosis or restenosis. In other instances, the cardiovascular injury is a vascular injury. In some aspects, the vascular injury is an aortic aneurysm or a thrombosis. For example, an aortic aneurysm can be an abdominal aortic aneurysm. In a further non-limiting example, the vascular injury can be a thrombosis associated with placement of a vascular stent. In various aspects, the method of treatment is a prophylactic or preventive treatment to prevent or delay onset of a disclosed cardiovascular disease or injury.

From the foregoing, it will be seen that aspects herein are well adapted to attain all the ends and objects hereinabove set forth together with other advantages which are obvious and which are inherent to the structure.

While specific elements and steps are discussed in connection to one another, it is understood that any element and/or steps provided herein is contemplated as being combinable with any other elements and/or steps regardless of explicit provision of the same while still being within the scope provided herein.

It will be understood that certain features and subcombinations are of utility and may be employed without reference to other features and subcombinations. This is contemplated by and is within the scope of the claims.

Since many possible aspects may be made without departing from the scope thereof, it is to be understood that all matter herein set forth or shown in the accompanying drawings and detailed description is to be interpreted as illustrative and not in a limiting sense.

It is also to be understood that the terminology used herein is for the purpose of describing particular aspects only, and is not intended to be limiting. The skilled artisan will recognize many variants and adaptations of the aspects described herein. These variants and adaptations are intended to be included in the teachings of this disclosure and to be encompassed by the claims herein.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Introduction. Drug-eluting stents (DES) represent a major medical advance in reducing restenosis, the re-blockage of angioplastied atherosclerotic arteries. However, stent thrombosis has become a major concern (1). The problem is two-fold. First, implanting a stent, a foreign object, is pro-inflammatory and thrombogenic, and also triggers neointimal hyperplasia (IH), the chief etiology of restenosis. Second, the anti-proliferative drugs coated on stents to curb IH including paclitaxel and rapamycin also block endothelial cell (EC) re-growth (termed re-endothelialization), thereby exacerbating stent thrombogenicity (2). The most feared consequence of stent thrombosis is high rates (up to 50%) of sudden death (1). Anti-coagulant therapies cannot completely prevent stent thrombosis, and they are associated with high costs and bleeding problems. Aside from all of these complications, compromised DES cannot be replaced, and hence a secondary, invasive revascularization such as bypass surgery is often required (1). Therefore, there is a clear clinical need for the development of an endothelium-protective and stent-free anti-restenotic therapy via innovations in both drug and its delivery method.

The recent discovery of small molecule inhibitors (JQ1 as the first in class) (3) that selectively block the bromo and extraterminal (BET) domain family of epigenetic reader proteins has opened the door to effectively treating previously recalcitrant condition (4). These inhibitors have shown excellent efficacy in treating proliferative and inflammatory diseases, such as cancer and heart failure, in preclinical tests or clinical trials (4). Of particular interest, our study using a rat model showed that JQ1 is an effective inhibitor of restenosis (5). More significantly, JQ1 also exhibited a prominent EC-protective effect in vitro and in viva (5, 6), which is a rare feature among the numerous anti-restenotic agents (7). Moreover, rapidly growing evidence supports a mechanism whereby JQ1 disrupts molecular complexes formed by BET proteins, transcription factors, super enhancers and/or other regulators that cooperatively define BET protein functional specificity (4). As such, JQ1 and its analogs appear to be promising EC-protective candidate drugs suitable for next-generation anti-restenotic therapy.

Targeted intravenous delivery to the injured arterial can be used to administer JQ1 in a non-invasive stent-free fashion, both nanoparticle (NP)-based and cell-based approaches have been extensively explored for targeted delivery (8). While systemically delivered "alien" NPs can elicit inflammatory responses, effects of cell therapy also are complicated by immune reactions. To reconcile the benefits and drawbacks of these two approaches, biomembrane-coated PLGA NPs have emerged as a novel biomimetic platform for delivery of therapeutics (9). They have shown excellent horning to injured tissues and minimal immunogenicity in that proof-of-concept study.

In this Example, this biomimicry/nanotechnology hybrid concept was applied in a rat model of balloon angioplasty for targeted intravenous delivery of JQ1, an endothelium-protective BET inhibitor (5, 6), in comparison to rapamycin, a status quo drug known to be EC-toxic (2, 7). JQ1 or rapamycin was loaded into nanoclusters formed by multiple PAMAM-polyvalerolactone (PAMAM-PVL) ultrasmall unimolecular NPs. These nanoclusters were then coated with platelet membranes that were deprived of immunogenicity (9) yet retaining the ability to target injured tissues, hereby termed biomimetic nanoclusters. A robust homing to balloon-injured areas in arteries was observed. Remarkably, whereas rapamycin nanoclusters inhibited IH as well as re-endothelialization, JQ1 nanoclusters preserved the ability of the endothelium to recover while mitigating IH.

Materials and Methods: Reagents and Materials, Human platelets and platelet membranes were purchased from ZenBio Inc (Research Triangle Park, NC). RNAlater solution, TRIzol, SuperScript IV VILA Master Mix, and SYBR Green PCR Mastermix was purchased from Thermo Fisher Scientific (Waltham, MA). Poly(amidoamine) (PAMAM; 4th generation dendrimer), Evans Blue, dimethyl sulfoxide (DMSO), valerolactone (VL), and stannous (H) octoate $(Sn(Oct)_2)$ were purchased from Sigma-Aldrich (St. Louis, MO). Rapamycin was purchased from LC Laboratories (Woburn, MA). JQ1 was purchased from ApexBio (Houston, TX). Cy5 dye was obtained from Lumiprobe Co. (Hallandale Beach, FL). Reagents not otherwise specified were purchased from Thermo Fisher Scientific (Fitchburg, WI)

Materials and Methods: Synthesis of Drug-Loaded Biomimetic Nanoclusters.

(a). Synthesis of Cy5-tagged ultrasmall unimolecular NPs (PAMAM-PVL-COOH/Cy5). PAMAM-PVL-OH was first prepared by ring-opening polymerization as reported previously (13). Thereafter, PAMAM-PVL-OH (50 mg) was reacted with succinic anhydride (8.2 mg) in the presence of 4-dimethylaminopyridine (12.5 mg) to yield PAMAM-PVL-COOH. The PAMAM-PVL-COOH/Cy5 was prepared by the reaction between PAMAM-PVL-COOH and $Cy5-NH_2$. Briefly, PAMAM-PVL-COOH (20 mg), N-hydroxysuccinimide (0.9 mg), and dicyclohexylcarbodiimide (2.1 mg) were added into dimethylformamide (5 mL). The solution was stirred for 30 min at 0° C. Thereafter, Cy5 (3.1 mg) was added into the solution. The reaction was carried out in the dark overnight. The impurities were then removed by dialysis against DI water for 48 h. The final product was dried under lyophilization.

(b). Synthesis of drug-loaded PAMAM-PVL ultrasmall unimolecular NPs. PAMAM-PVL-COOH (50 mg) and JQ1 (20 mg) were dissolved in DMSO (5 mL). DI water (15 mL) was added dropwise into the above solution over 30 min. Thereafter, the un-loaded drugs and DMSO were removed by dialysis against DI water for 48 h. The JQ1-loaded NPs were obtained after lyophilization. The rapamycin-loaded ultrasmall unimolecular NPs were prepared following a similar method.

(c). Synthesis of drug-loaded biomimetic nanoclusters. The platelet membrane was derived as previously reported (9). Biomimetic nanoclusters were prepared by dispersing and fusing platelet biomimetic nanoclusters with PAMAM-PVL-COOK or PAMMA-PVL-COOH/Cy5 under sonication for 2 min (1 mg of PAMAM-PVL-COOH to 67 µl of platelet vesicle solution). The drug-loaded nanoclusters were prepared following a similar protocol by fusing drug-loaded (e.g., rapamycin and JQ1) ultrasmall unimolecular NPs with platelet membranes.

(d). Characterizations. 1H NMR spectra of all polymer products were recorded on a Varian Mercury Plus 300 spectrometer in $DMSO-d_6$ or $CDCl_3$ at 25° C. Molecular weights (Mn and Mw) and polydispersity indices (PDI) of the polymers were determined by a gel permeation chrornatographer (GPC) equipped with a refractive index detector, a viscometer detector, and a light scattering detector (Viscotek, USA), DMF with 0.01 M of LiBr was used as the mobile phase with. Fourier transform infrared (FT-IR) spectra were recorded on a Bruker Tensor 27 FT-IR spectrometer. The sizes and morphologies of the NPs were studied by dynamic light scattering (DLS, ZetaSizer Nano ZS90, Malvern Instruments, USA) and transmission electron microscopy (TEM, FEI Tecnai G2 F30 TWIN 300 KV, E.A, Fischione Instruments, Inc. USA). The zeta potentials were measured by ZetaSizer Nano ZS90 (Malvern Instruments, USA). The rapamycin loading level was measured by high-performance liquid chromatography (HPLC) using ultraviolet (UV) detection at 278 nm. The JQ1 loading level was measured by UV-Vis spectrometer at 323 nm.

Materials and Methods: In Vitro Drug Release,

The in vitro drug release profiles from both rapamycin-loaded and JQ1-loaded biomimetic nanoclusters were studied in PBS (pH=7.4) (19). Briefly, drug-loaded biomimetic nanoclusters in the PBS (1 mg/mL, 5 mL) were enclosed in a cellulose membrane dialysis bag (molecular weight cutoff, 8 kDa). The dialysis bags were immersed in 100 mL of PBS, which was then kept in a horizontal laboratory shaker (100 rpm) at 37° C. At predetermined time intervals, 5 mL samples were collected and replaced with the same volume of PBS. The amounts of rapamycin and JQ1 in the collected samples were measured by HPLC and UV-Vis spectrometer, respectively, as indicated above.

Materials and Methods: Rat carotid artery balloon angioplasty. Carotid artery balloon angioplasty was performed in male Sprague-Dawley rats (Charles River; about 400 g) as previously described (5, 20). Briefly, rats were anesthetized with isoflurane (5% for inducing and 2.5% for maintaining anesthesia). A longitudinal incision was made in the neck and carotid arteries were exposed. A 2-F balloon catheter (Edwards Lifesciences, Irvine, CA) was inserted through an arteriotomy on the left external carotid artery. To produce arterial injury, the balloon was inflated at a pressure of 2 atm and withdrawn to the carotid bifurcation and this action was repeated three times. The external carotid artery was then permanently ligated, and blood flow was resumed. Drug-loaded biomimetic nanoclusters or compound solutions were injected via rat tail vein. Animals were euthanized in a $CO_2$ chamber at day 5 (for artery ex vivo imaging) or day 14 (for morphometric analysis) after balloon injury.

Figure 10:
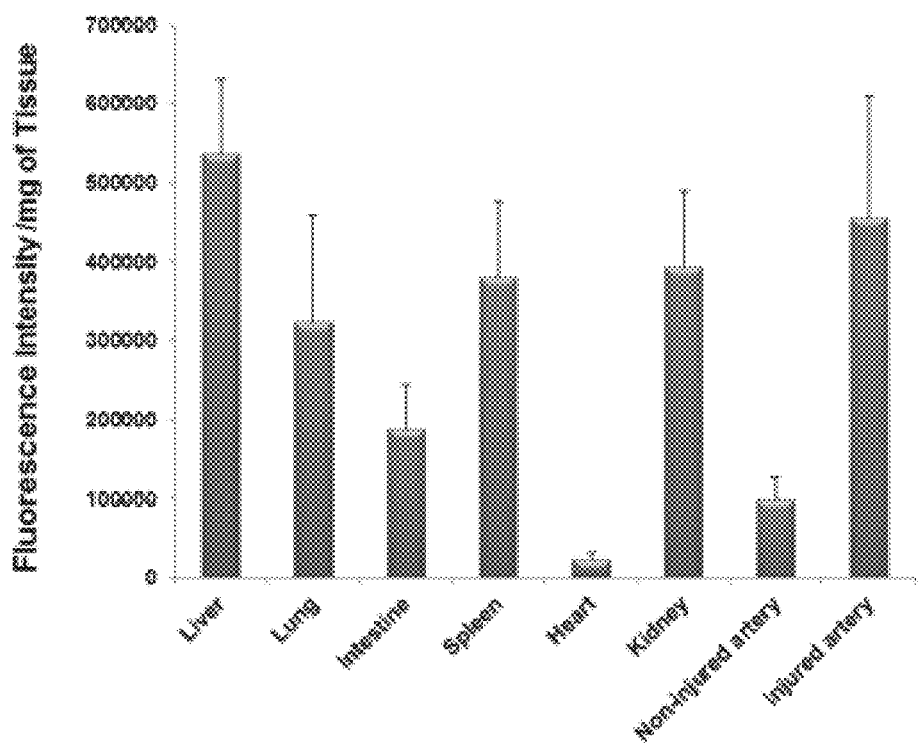
FIG. 10 shows a graph that can demonstrate the biodistribution of biomimetic nanoclusters. Cy5-tagged nanoclusters were coated with platelet membranes, and tail-vein injected (2.5 mg/kg animal weight) immediately after balloon angioplasty of the rat carotid artery. Animals were euthanized 5 days later. Various organs including balloon-Injured arteries and uninjured contralateral arteries were collected for imaging with an IVIS spectrum luminescence system (Ex/Em: 650/720 nm). Fluorescence intensity per mg of tissue was quantified.
Figure 11:
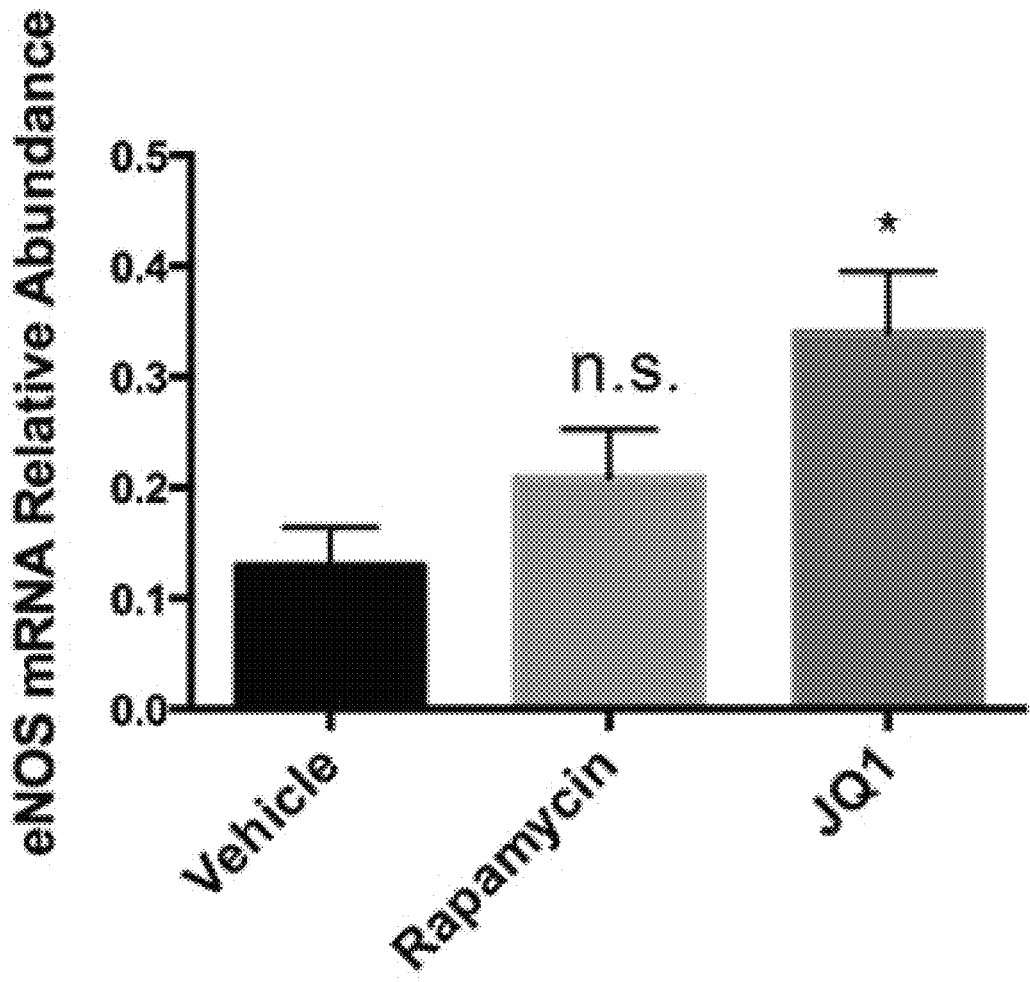
FIG. 11 shows representative data for mRNA levels of eNOS. Briefly, the study was carried out as described for FIGS. 3A-3C, in that Evans Blue-stained arteries were transiently fixed with RNAlater solution and subjected to RNA extraction and qPCR analysis. Quantification: Mean±SEM, n=3 rats; *p<0.05, n.s., not significant, compared to vehicle control.
Figure 12A:
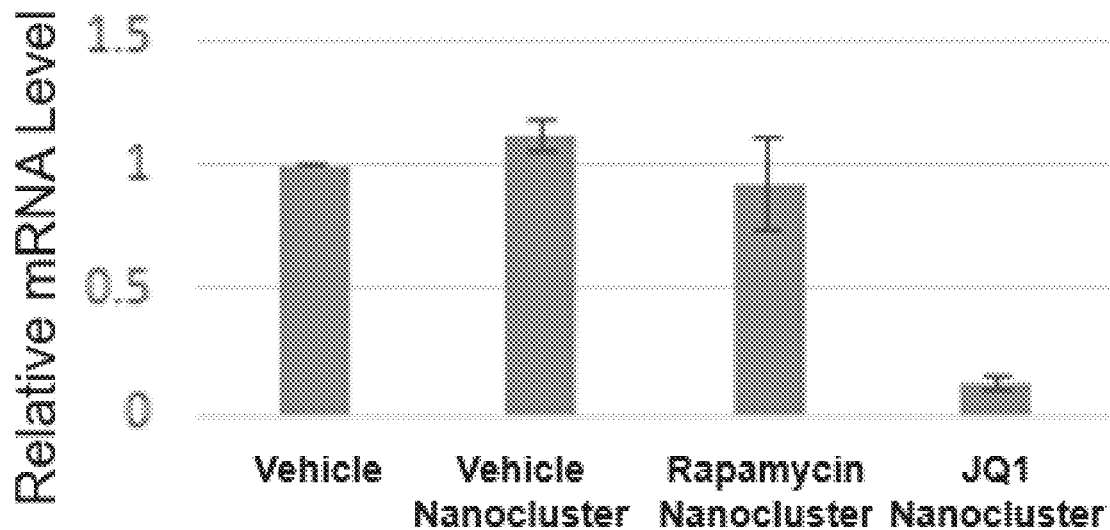
FIGS. 12A-12L show representative data for relative mRNA levels for tissue inflammatory cytokines (RANTES, MCP1, IL1β, TNFα, and IL6) or apoptosis (BAX, a key factor in the apoptosis pathway) in spleen or liver following treatment with various disclosed nanoclusters. Briefly, the study was carried as described for FIGS. 4A-4C, in that Non-fixed tissues were used for quantitative real time PCR. The data show that whereas the rapamycin/nanoclusters increased MCP-1 and TNFα in the spleen, the JQ1/nanoclusters generally reduced inflammatory cytokines in the spleen and liver.
Figure 12B:
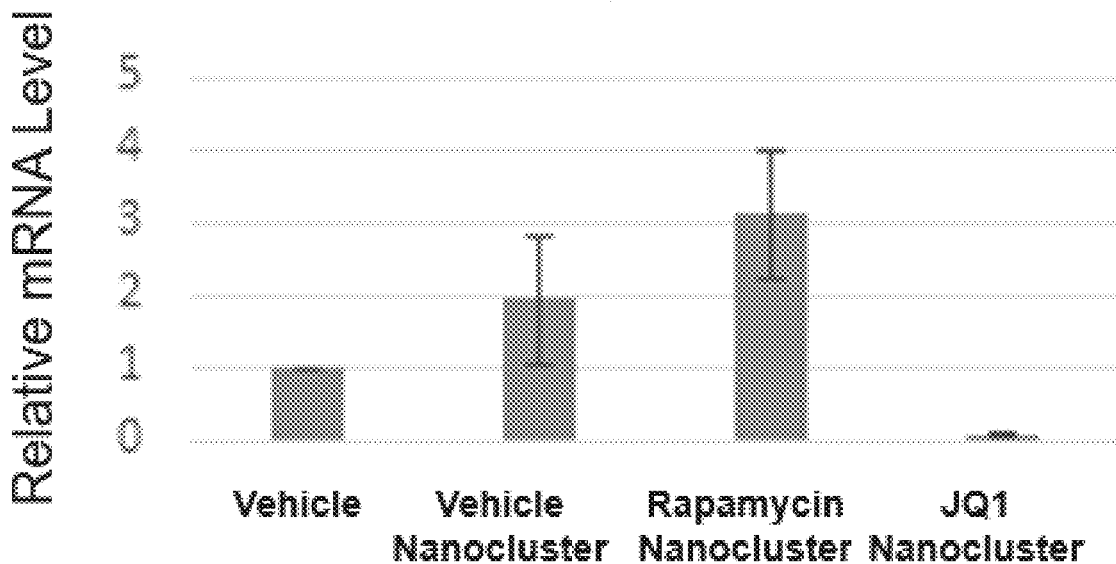
Figure 12C:
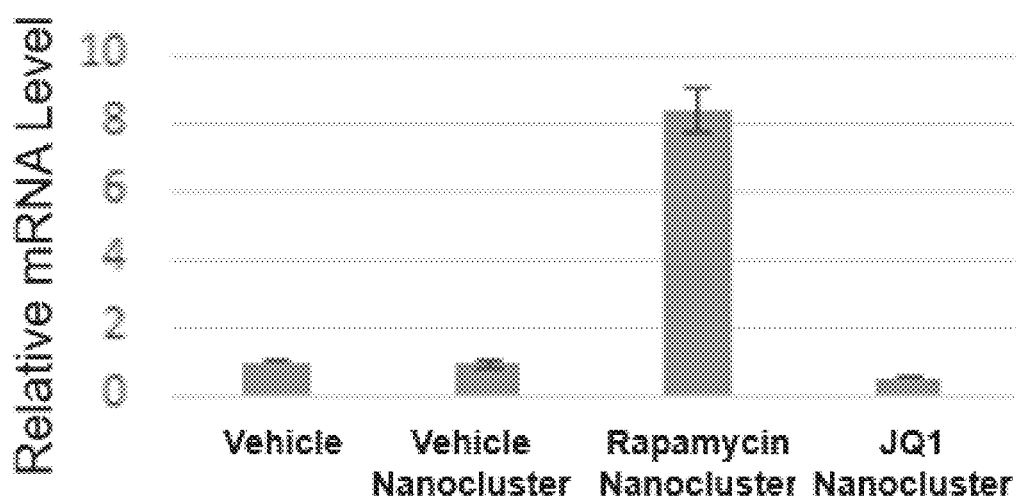
Figure 12D:
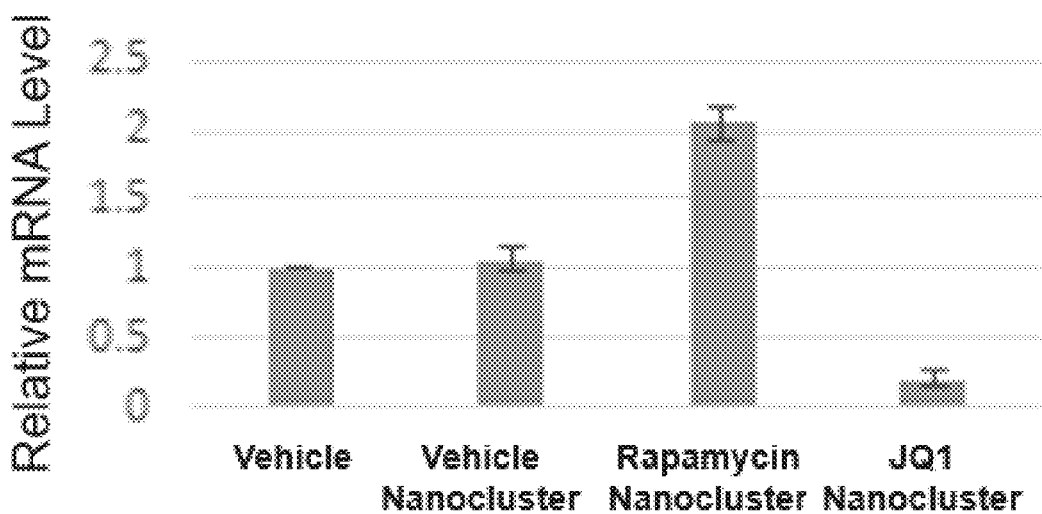
Figure 12E:
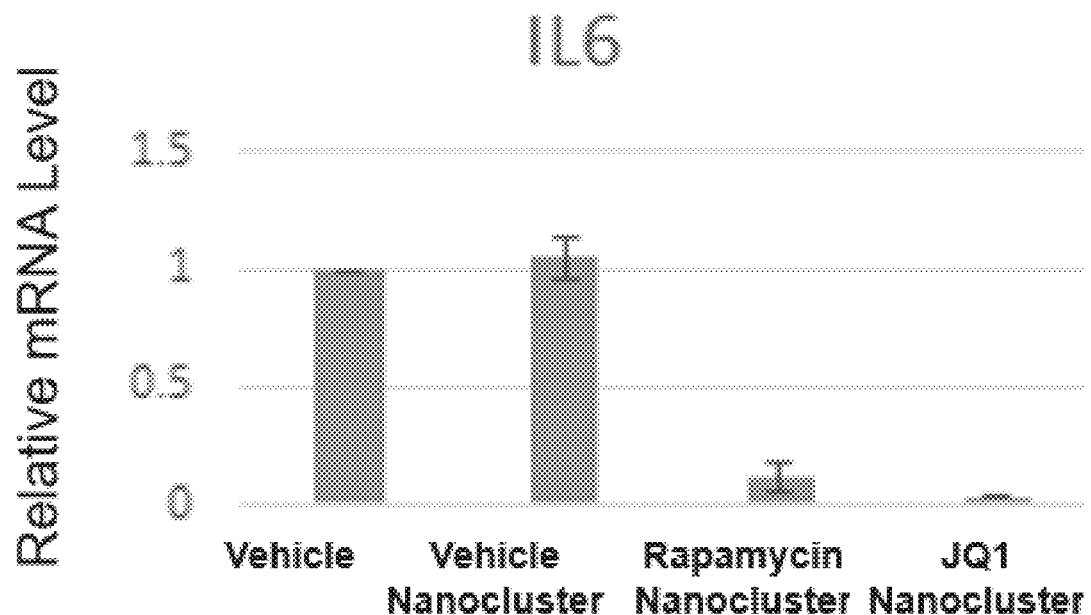
Figure 12F:
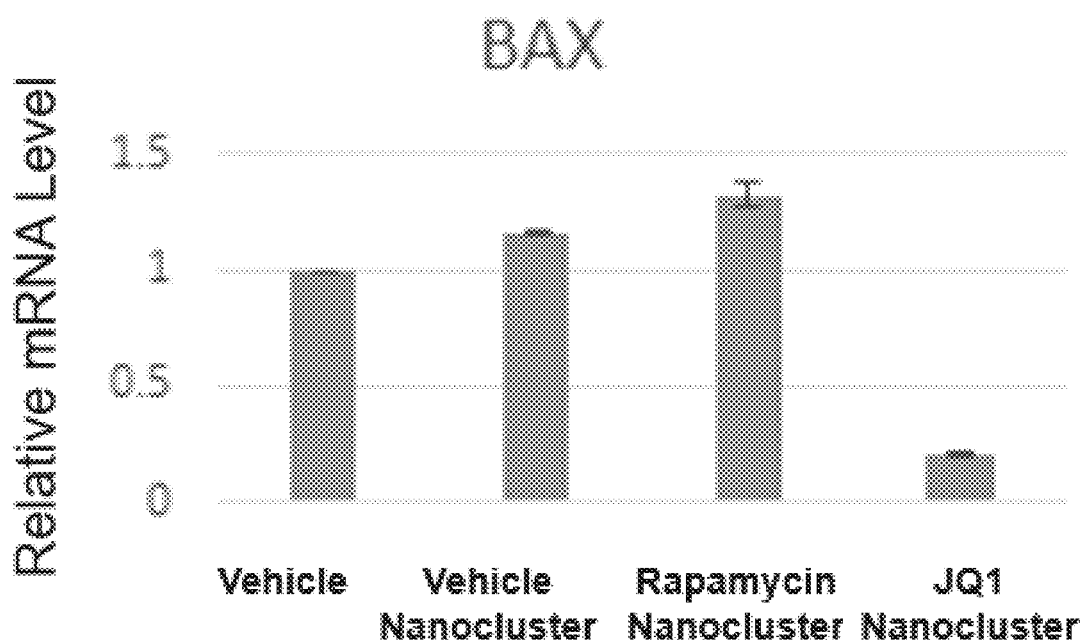
Figure 12G:
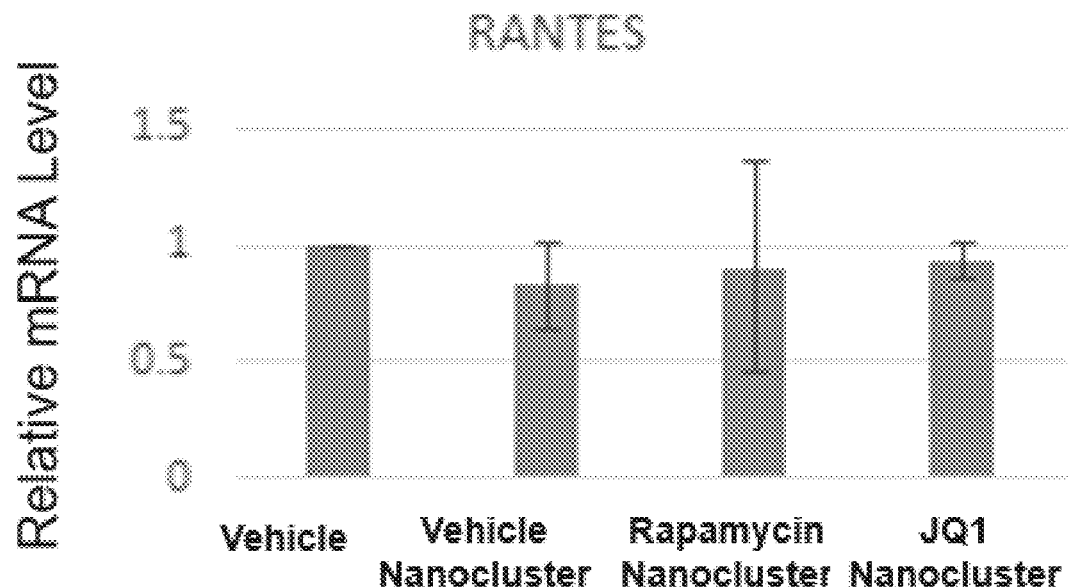
Figure 12H:
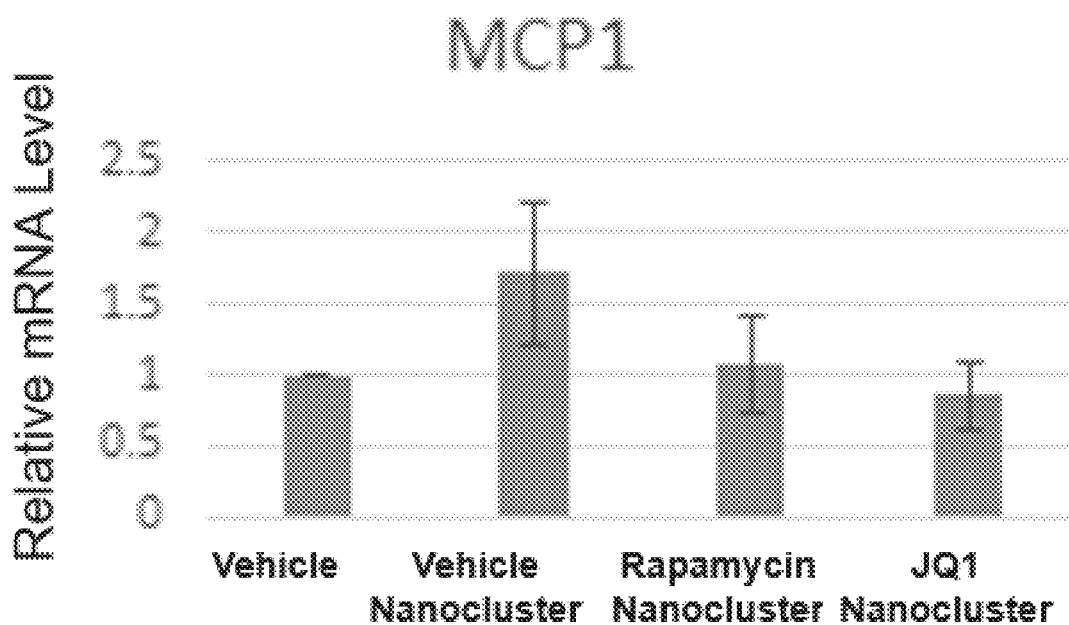
Figure 12I:
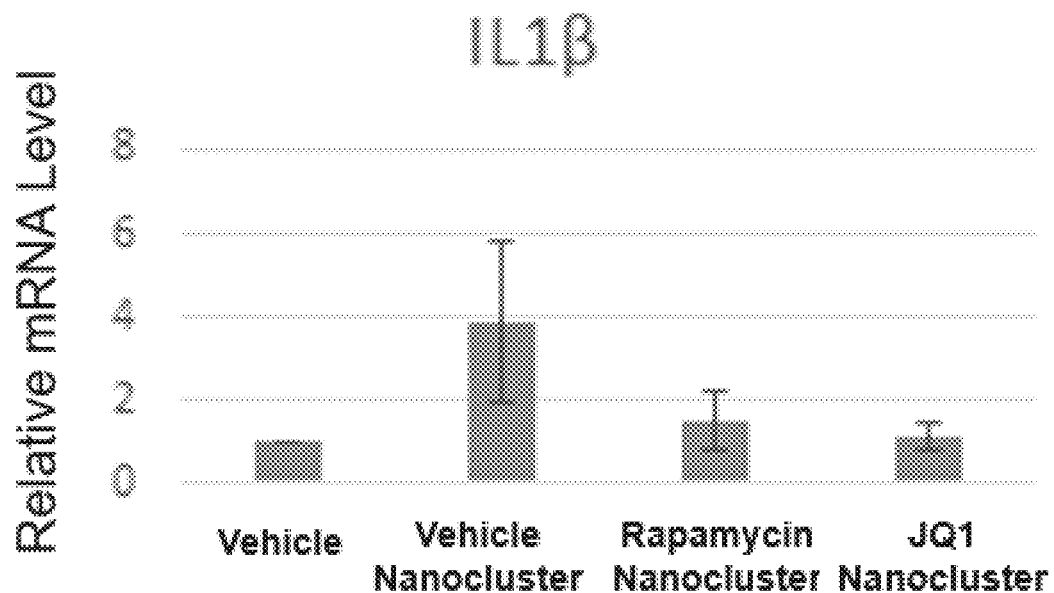
Figure 12J:
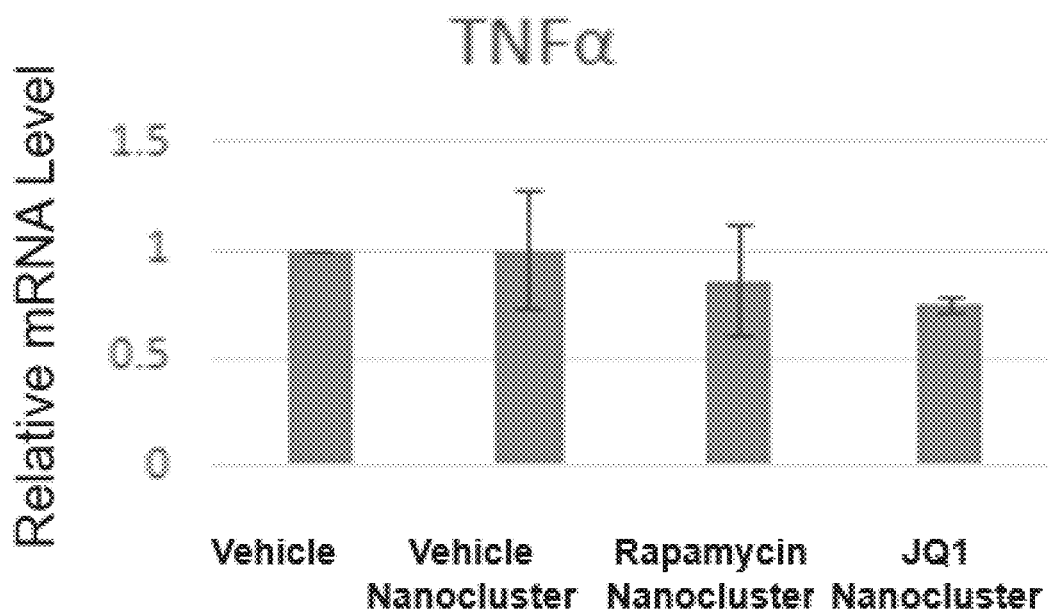
Figure 12K:
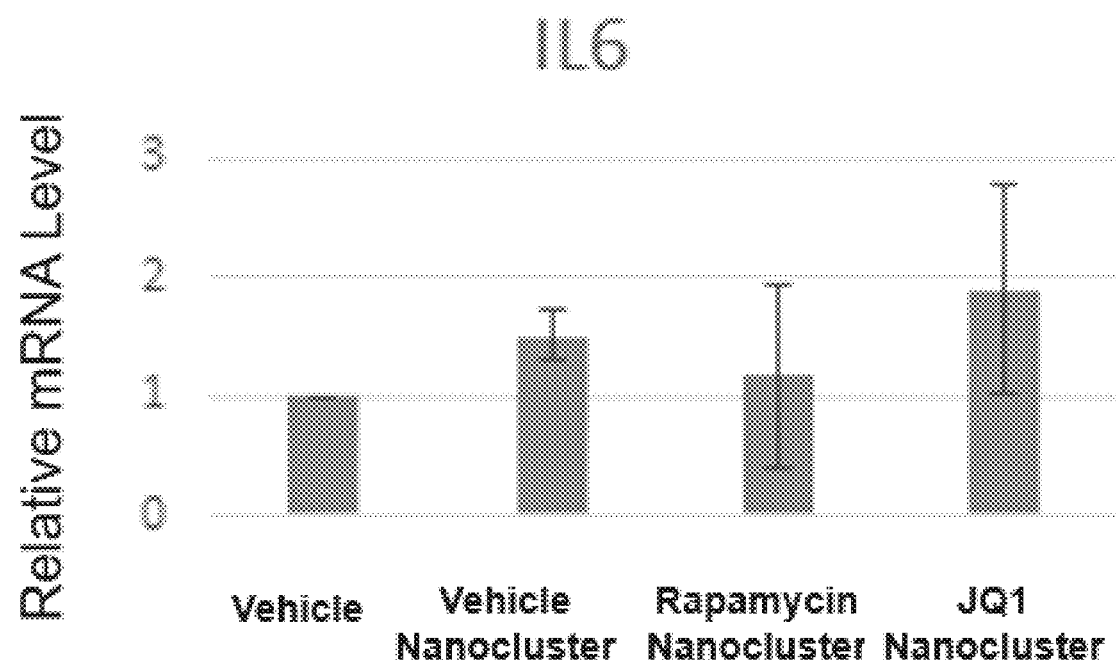
Figure 12L:
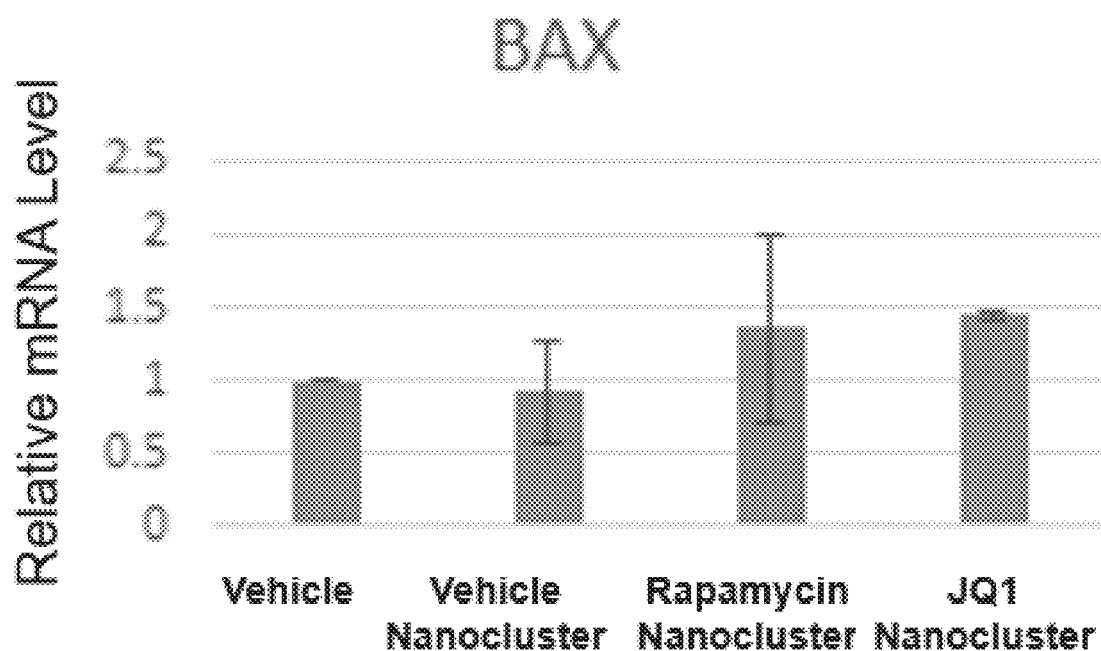
Figure 13A:
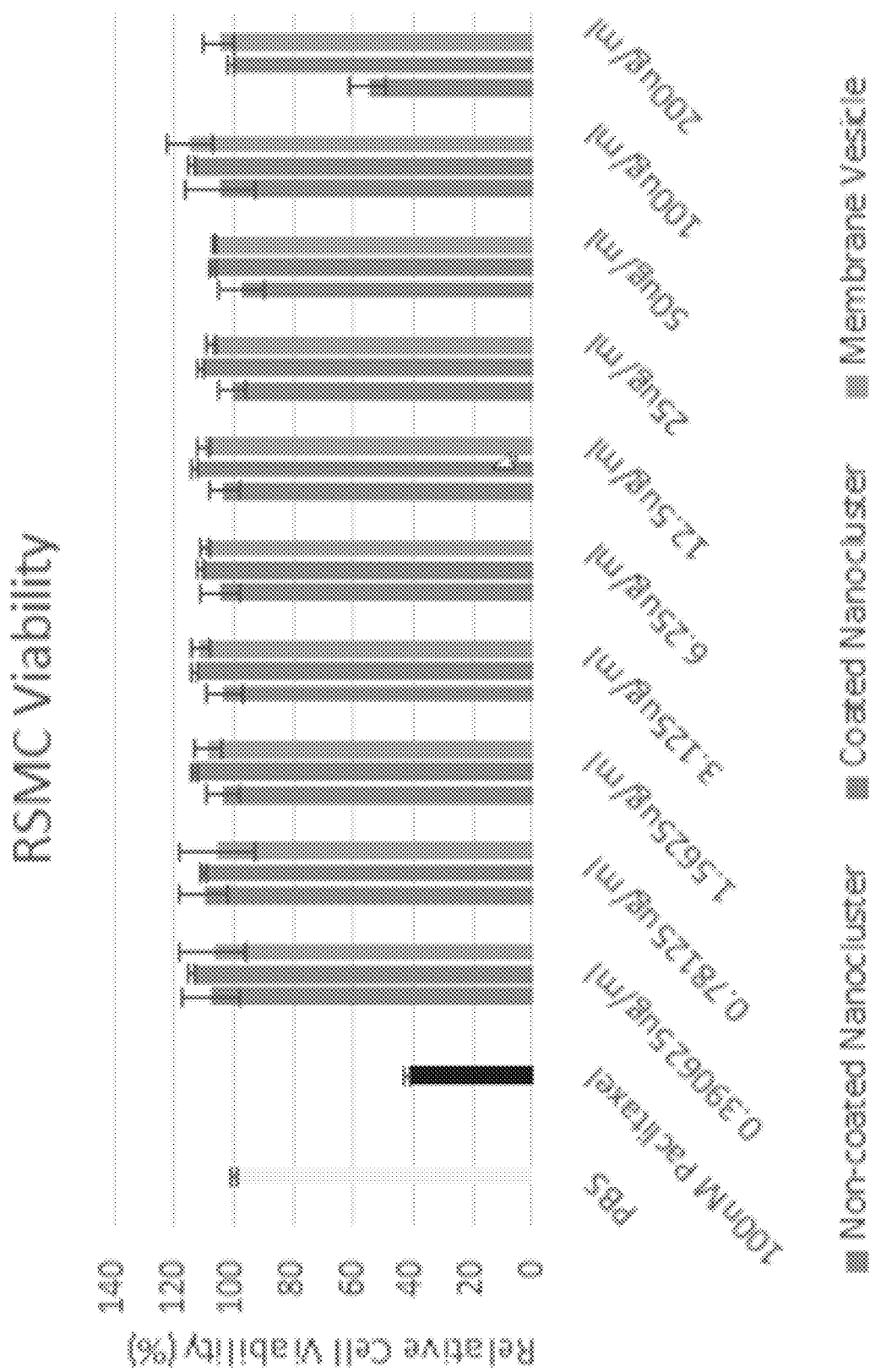
FIGS. 13A-13D show representative data pertaining to cell toxicity following exposure of cell-lines to representative disclosed nanoclusters. Briefly, cells were cultured (cell type as indicated), and incubated with increasing concentrations (as indicated) of non-coated nanoclusters, coated nanoclusters, or platelet membrane vesicles. Cell viability was measured using the CellTiterGlo assay. Paclitaxel was used as a positive control for the assay. RSMC: rat aortic smooth muscle cells; HASMC: rat aortic smooth muscle cells; REC: rat aortic endothelial cells; HUVEC: human umbilical endothelial cells.
Figure 13B:
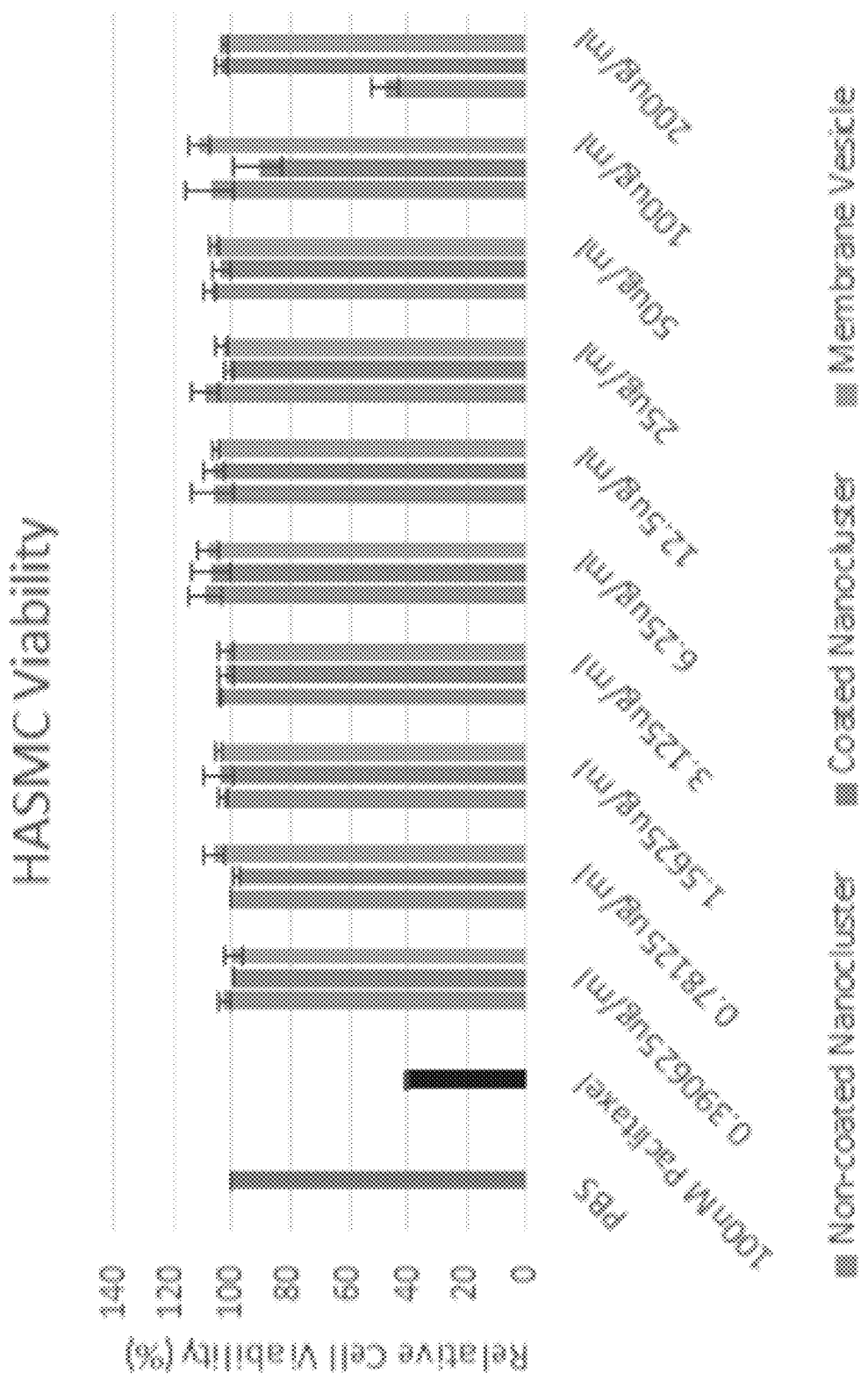
Figure 13C:
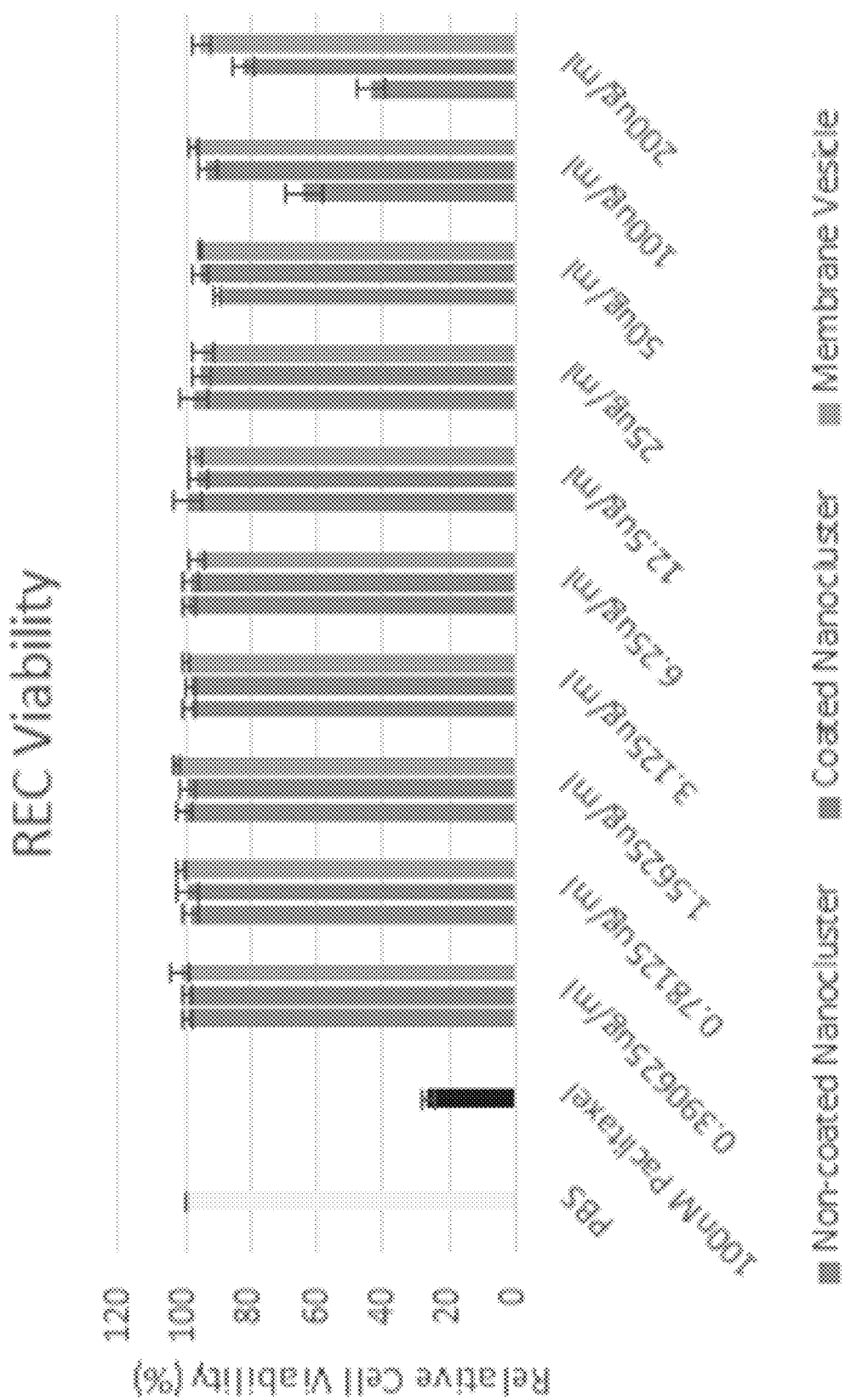
Figure 13D:
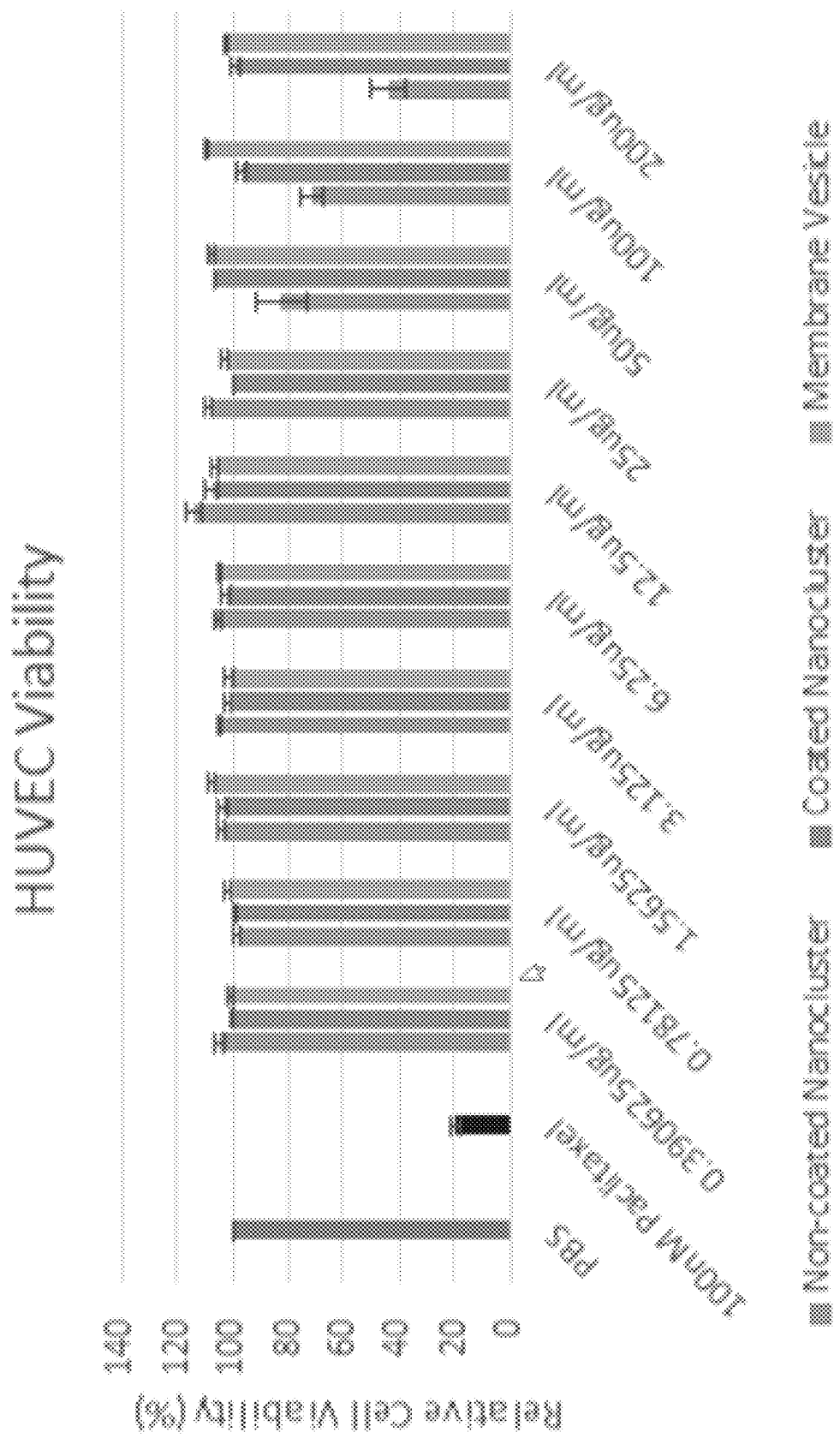
Figure 14A:
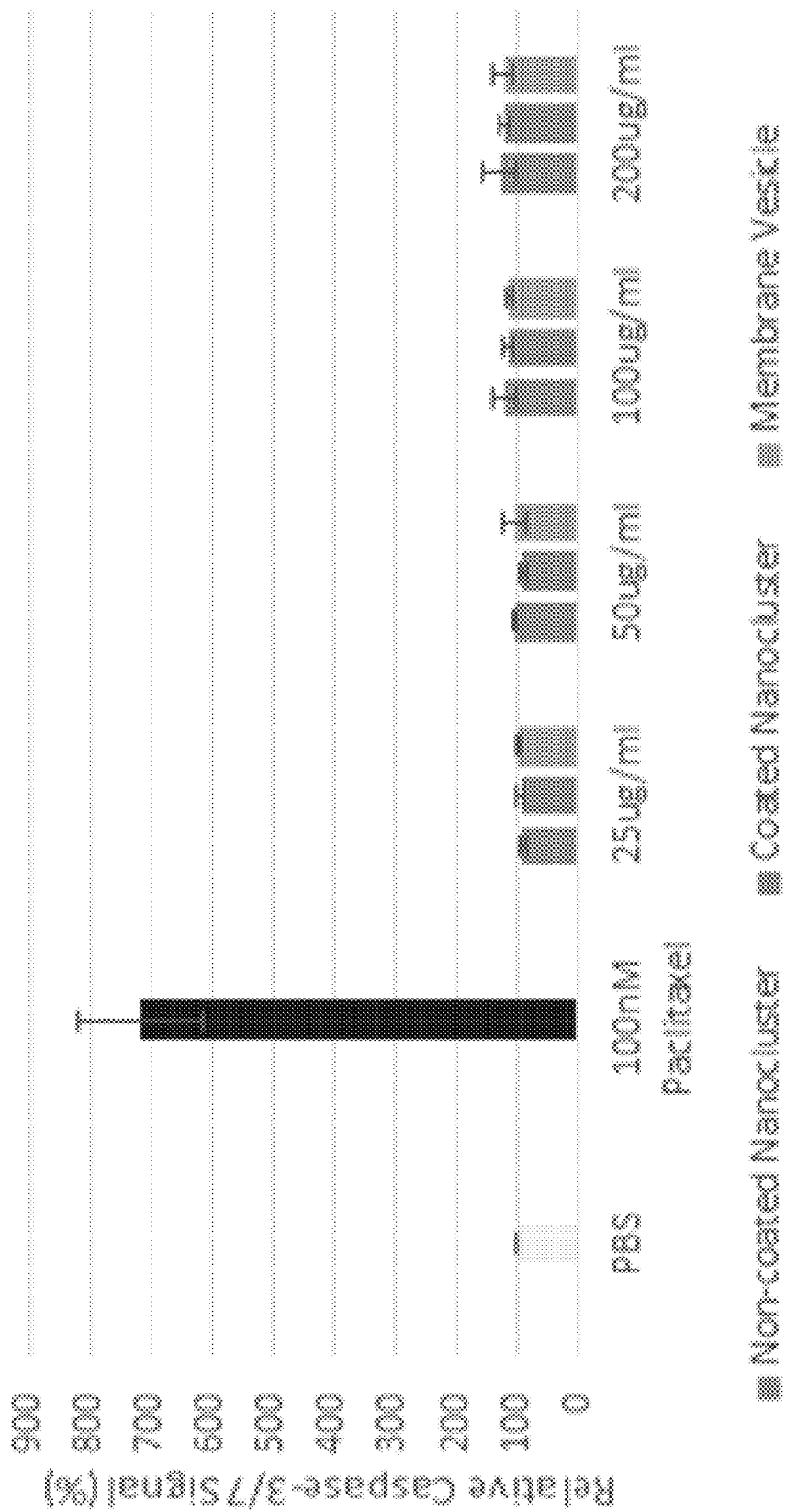
FIGS. 14A-14D show representative data pertaining to induction of apoptosis following exposure of cell-lines to representative disclosed nanoclusters. Briefly, cells were cultured, and incubated with increasing concentrations (as indicated) of non-coated nanoclusters, coated nanoclusters, or platelet membrane vesicles, as described in Figure S6. Caspase3/7 activity was then determined. Paclitaxel was used as a positive control for the assay. RSMC: rat aortic smooth muscle cells; HASMC: rat aortic smooth muscle cells; REC: rat aortic endothelial cells; HUVEC: human umbilical endothelial cells.
Figure 14B:
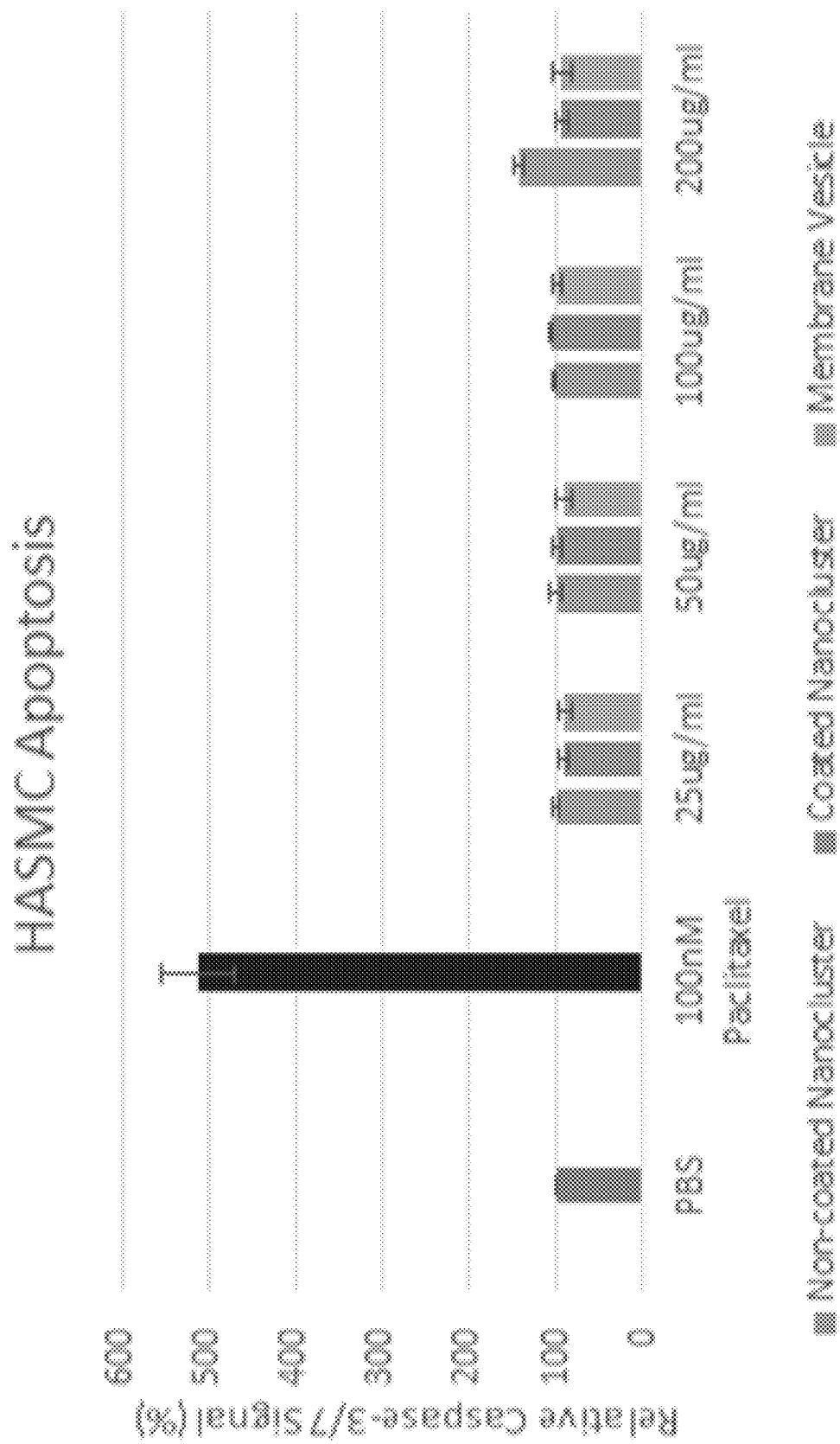
Figure 14C:
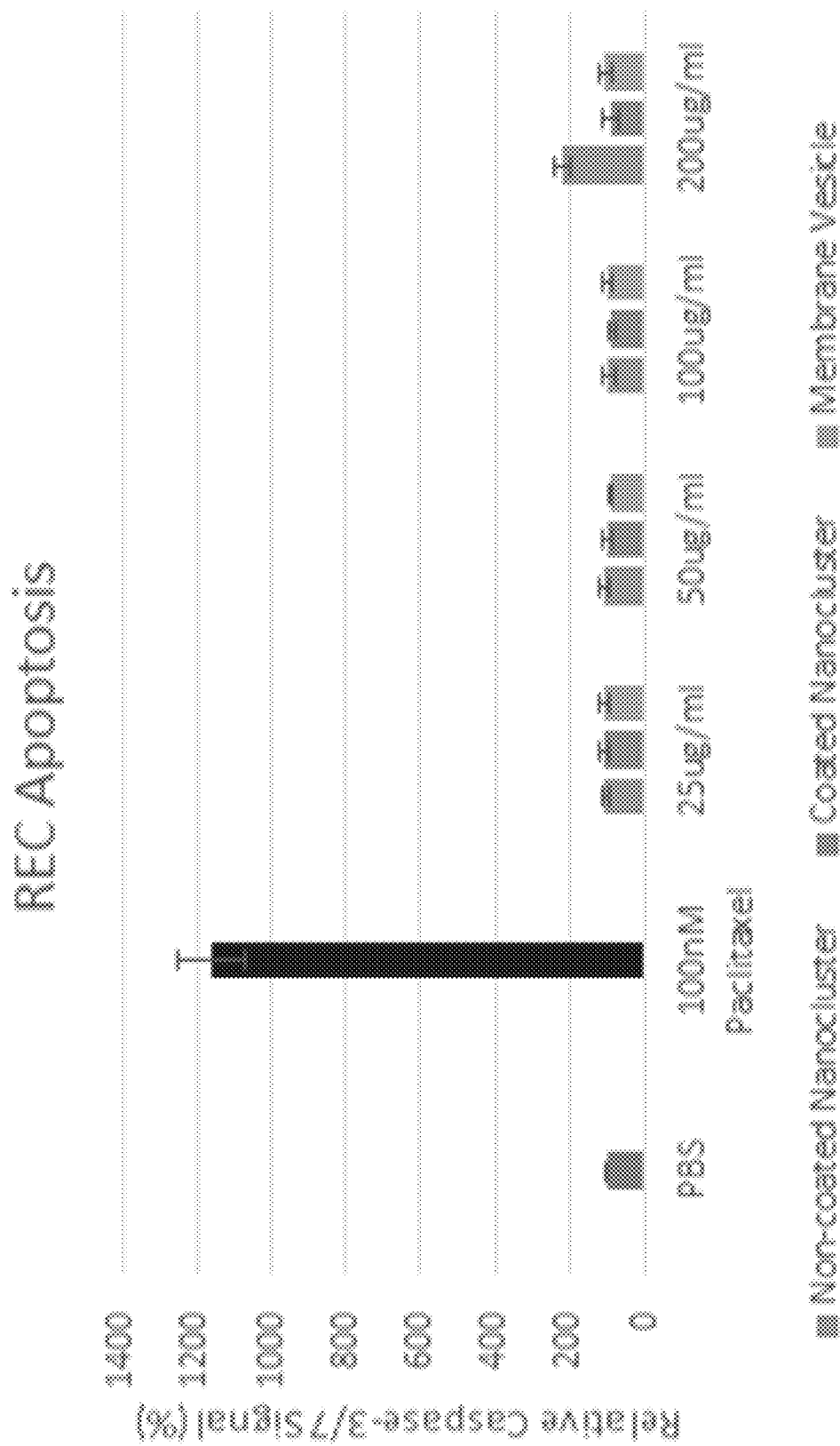
Figure 14D:
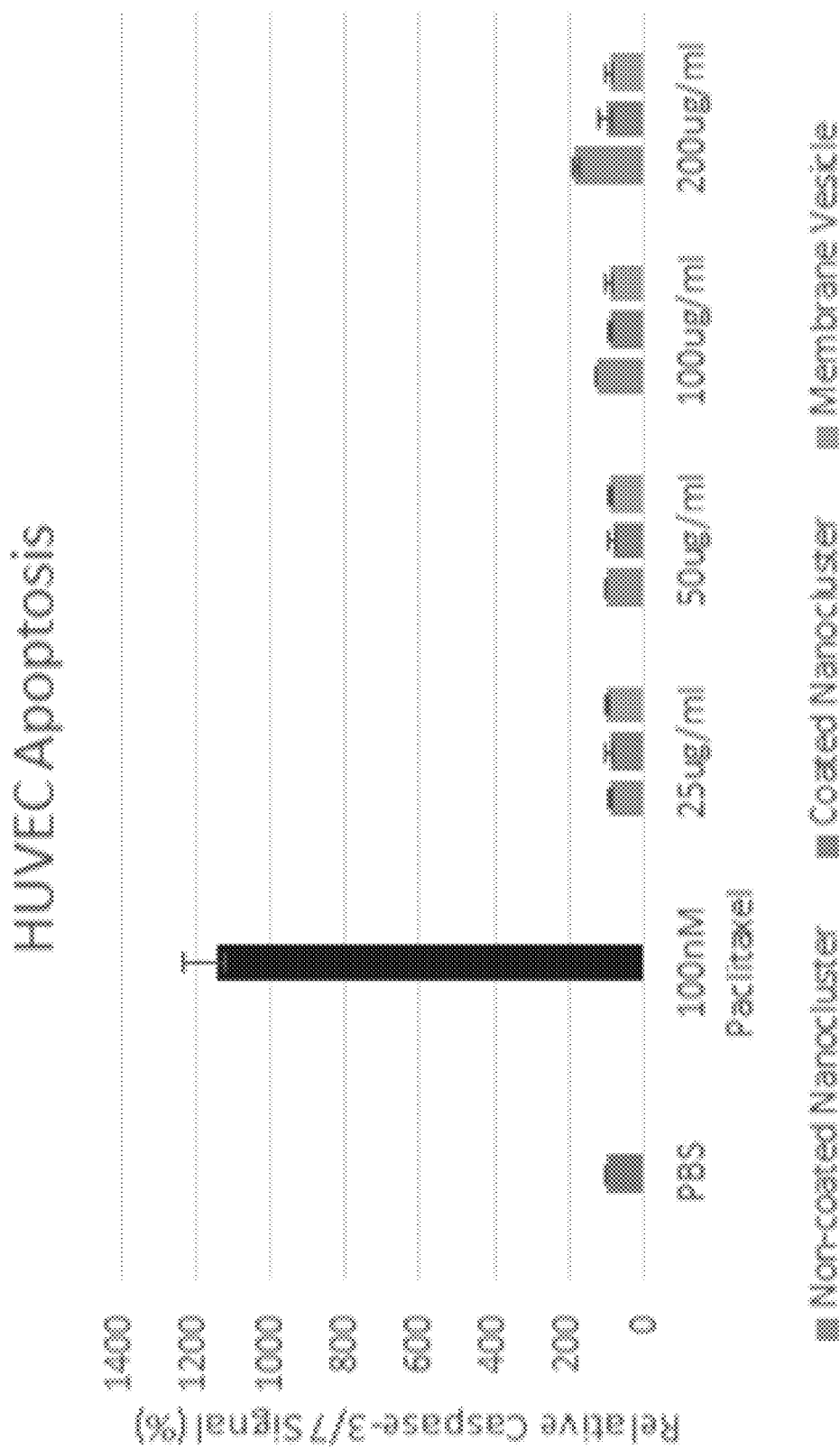

Materials and Methods: IVIS imaging for homing of biomimetic nanoclusters. Cy5-tagged nanoclusters were coated with platelet membranes, as described above, and tail-vein injected (2.5 mg/kg animal weight) immediately after balloon angioplasty of the rat carotid artery. Animal were euthanized 5 days later. Various organs (see FIG. 10) including balloon-injured arteries and uninjured contralateral arteries were collected. Ex vivo fluorescence imaging was performed to track Cy5-tagged nanoclusters using an IVIS spectrum luminescence system (Ex/Em: 650/720 nm).

Materials and Methods: Morphometric analysis of neointima. Two weeks after balloon angioplasty, common carotid arteries were collected from anesthetized animals (under 2.5% isoflurane) following perfusion fixation at a physiological pressure of 100 mm Hg. The animals were then euthanized. Paraffin sections (5 µm thick) were excised from carotid arteries at equally spaced intervals and then Van Gieson stained for morphometric analysis, as described in our previous reports (5, 20). Planimetric parameters as follows were measured on the sections and calculated using Image J: area inside external elastic lamina (EEL area), area inside internal elastic lamina (IEL area), lumen area, intima area (=IEL area−lumen area), and media area (=EEL area−IEL area). Intimal hyperplasia was quantified as a ratio of intima area versus media area. Measurements were performed by a researcher blinded to the experimental conditions using 3-6 sections from each of animal. The data from all sections were pooled to generate the mean for each animal. The means from all the animals in each treatment group were then averaged, and the standard error of the mean (SEM) was calculated.

Materials and Methods: Re-endothelialization study with Evans Blue dye. Re-endothelialization in balloon-injured arteries was evaluated on day 5 after angioplasty using Evans Blue assay according to the previously published method with minor modifications (20). Briefly, 1 ml of 0.5% Evans Blue dye was injected into tail vein under anesthesia by 2,5% isoflurane. After 30 min, rats were perfused with 10 ml of PBS buffer, followed by 10 ml perfusion with RNAlater to transiently preserve RNA in endothelium. The common carotid arteries were dissected and peri-adventitial connective tissues were trimmed to avoid contamination in downstream RNA extraction. Common carotid arteries were collected starting from the proximal end to the aortic arch, and were then longitudinally opened and photographed on a white background. Denuded areas were stained blue; unstained areas indicate re-endothelialization and were quantified using Image J. Re-endothelialization index was calculated by normalizing the unstained artery length of post-angioplasty day 5 to that right after angioplasty (day 0). Immediately after images were taken, the carotid segments were rinsed in PBS multiple times, dried on Kimwipes, and snap-frozen in liquid nitrogen, until later processed for tissue RNA extraction.

Materials and Methods: Real-time Quantitative PCR (qRT-PCR). mRNA was isolated from collected carotid segments using TRIzol following the manufacturer's instructions. Purified mRNA (1 µg) was used for the first-strand cDNA synthesis and quantitative RT-PCR was performed using the 7500 Fast Real-Time PCR System (Applied Biosystems, Carlsbad, CA). Each cDNA template was amplified in triplicates using SYBR Green PCR Master Mix, with the following primer sets: Rat VCAM1 forward primer CTCCTCTCGGGAAATGCCAC (SEQ ID NO:1), reverse primer AACAACGGAATCCCCAACCT (SEQ ID NO:2); Rat MCP1 forward primer CTTC-CAAGTGGCTAAGGGCA (SEQ ID NO:3), reverse primer TCAAAGGGAGTCGGGGATCT (SEQ ID NO:4); Rat Flk1 forward primer CTTCCAAGTGGCTAAGGGCA (SEQ ID NO:5), reverse primer TCAAAGGGAGTCGGG-GATCT (SEQ ID NO:6); Rat GAPDH forward primer GACATGCCGCCTGGAGAAAC (SEQ ID NO:7), reverse primer AGCCCAGGATGCCCTTTAGT (SEQ ID NO:8).

Materials and Methods: Statistical Analysis.

Data are presented as a mean±standard error of the mean (SEM). Statistical analysis was conducted using one-way ANOVA followed by Bonferroni post-hoc tests. Data are considered statistically significant when a P value is at least <0.05.

Results: Synthesis and Characterization of Drug-Loaded Nanoclusters.

Figure 1C:
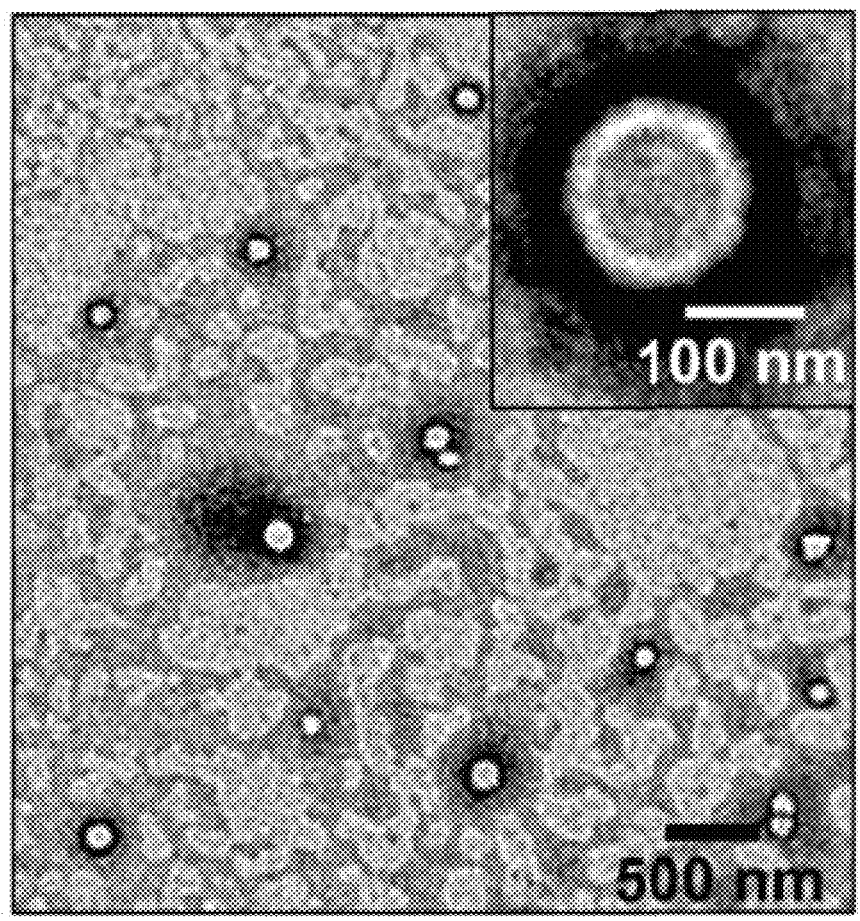
Figure 5:
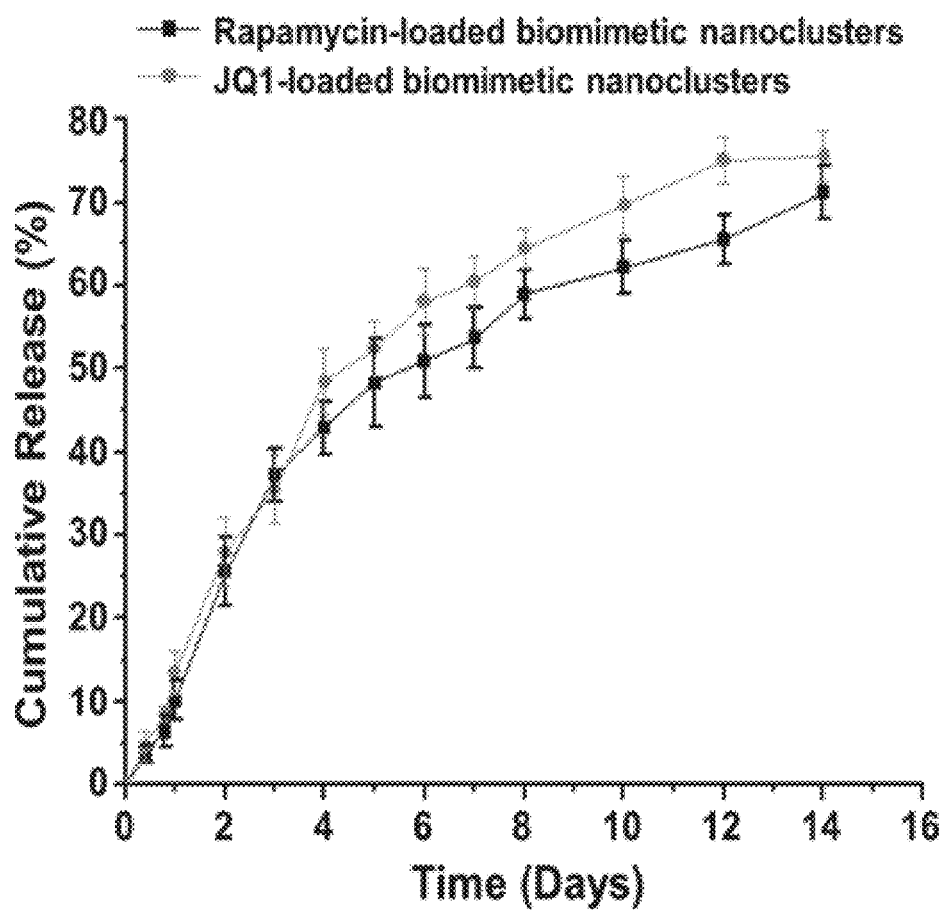
FIG. 5 shows a graph that can demonstrate the in vitro release of rapamycin and JQ1 from biomimetic nanoclusters.

The biomimetic nanoclusters were prepared by fusing human platelet membrane with nanoclusters formed by hundreds of PAMAM-PVL ultrasmall unimolecular NPs (FIGS. 1A-1C). The platelet biomimetic nanoclusters were first derived from human platelets. The zeta potential of the platelet biomimetic nanoclusters was −29.8±6.6 mV. The bare polymeric nanocluster was formed by hundreds of PAMAM-PVL-COOH (or PAMAM-PVL-COOH/Cy5 for tracking study) unimolecular NPs in an aqueous solution. It was estimated that each nanocluster was made of approximately 500 of PAMAM-PVL-COOH unimolecular NPs based on the volumes of the nanocluster and individual ultrasmall unimolecular NP about 18 nm by DLS in DMF). The bare nanoclusters possessed negative zeta potentials (Table 1), due to the COOH terminal groups present on the surface of the PAMAM-PVL-COOH ultrasmall NP, which could facilitate the membrane coating process according to the previous reports (21). The average hydrodynamic diameter and zeta potential of the bare nanoclusters were 138 nm, and −37.1 mV, respectively. The final biomimetic nanoclusters were approximately 24 nm larger than the bare nanoclusters and processed similar surface charge as the platelet-biomimetic nanoclusters (Table 1). The hydrophobic drugs, rapamycin and JQ1, were loaded into nanoclusters through hydrophobic interactions as well as hydrogen binding. The drug loading level was 21.5% for JQ1, and 20.8% for rapamycin. FIG. 5 shows the in vitro drug release profiles of drug-loaded biomimetic nanoclusters. Both rapamycin and JQ1 was released in a sustainable manner without a burst release.

TABLE 1

| Sample | Size (nm) | Zeta potential (mV) |
| --- | --- | --- |
| Platelet membrane vesicles | 345.1 ± 61.6 | −29.8 ± 6.6 |
| Bare nanoclusters | 137.7 ± 26.2 | −37.1 ± 4.7 |
| Platelet membrane-coated nanoclusters | 162.1 ± 24.1 | −30.6 ± 5.4 |

Figure 2A:
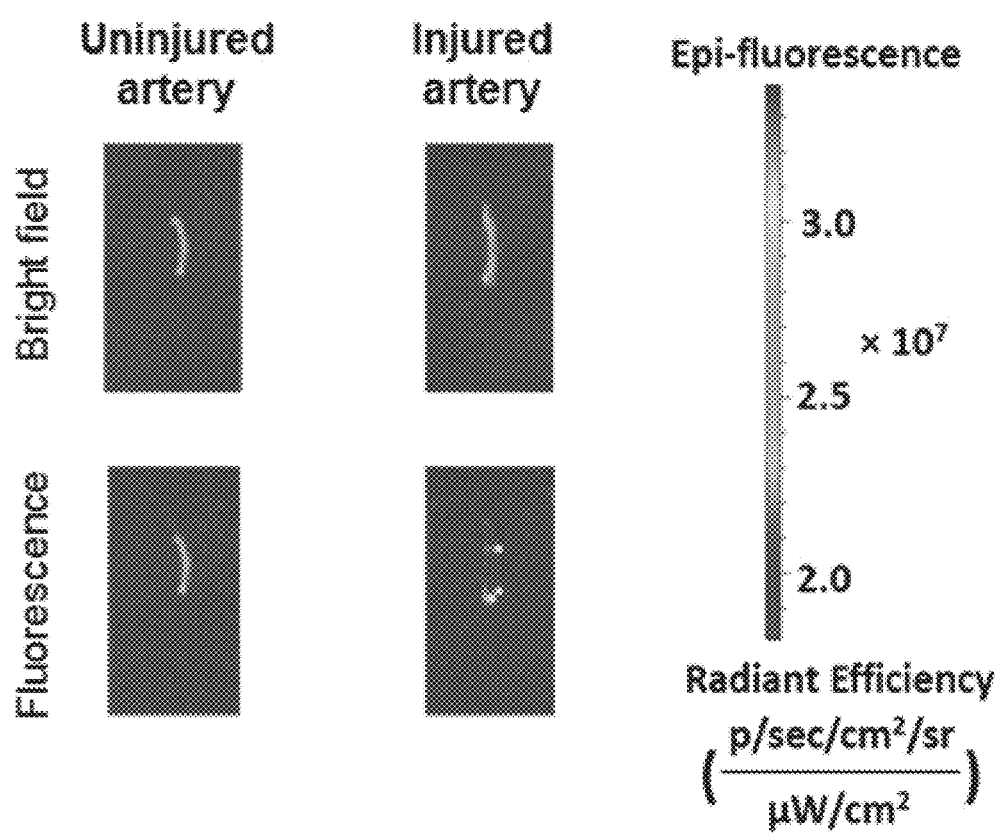
FIGS. 2A-2B can demonstrate the homing of biomimetic nanoclusters to injured carotid arteries. Cy5-tagged nanoclusters were coated with platelet membranes, as described in FIGS. 1A-1C, and tail-vein injected (2.5 mg/kg animal weight) immediately after balloon angioplasty of the rat carotid artery.
Figure 2B:
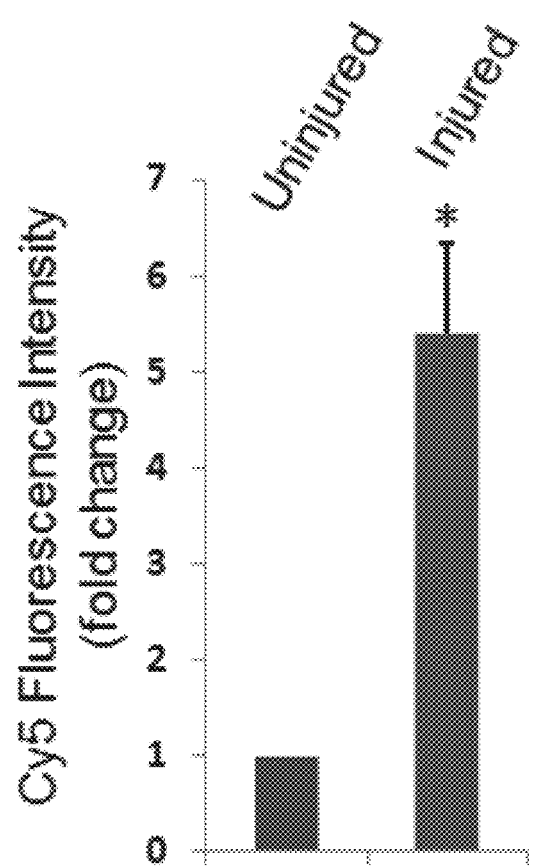
Figure 6:
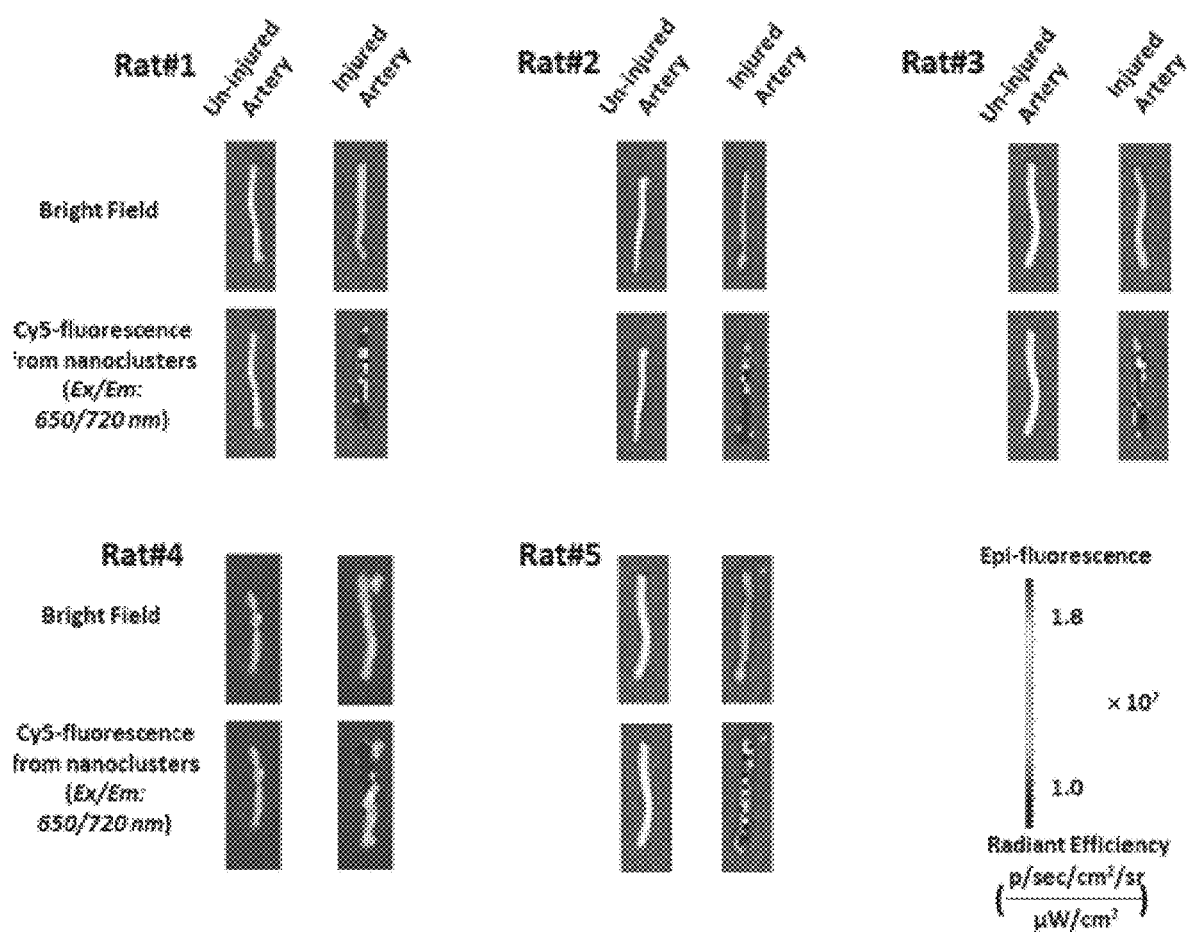
FIG. 6 shows images that can demonstrate the homing of biomimetic nanoclusters to injured carotid arteries. These are in addition to that presented above in FIG. 2A. Cy5-tagged nanoclusters were coated with platelet membranes, and tail-vein injected (2.5 mg/kg animal weight) immediately after balloon angioplasty of the rat carotid artery. Balloon-Injured arteries and uninjured contralateral arteries were collected 5 days later for ex vivo imaging with an IVIS spectrum luminescence system (Ex/Em: 650/720 nm). Note Cy5 fluorescence was detected from injured, but not uninjured arteries.

Results: Biomimetic nanoclusters can effectively home to a balloon-injured carotid artery wall Biomimetic (platelet membrane-coated) nanoclusters were prepared as indicated in FIGS. 1A-1C. Detailed characterization of the biomimetic nanoclusters (e.g., size, zeta potential, and drug release profiles) can be found in the supplemental file (Table 1 and FIG. 5). Their post-injection homing was visualized via the Cy5 fluorophores that were conjugated to the unimolecular NPs forming the nanoclusters. Immediately after balloon angioplasty in the rat carotid artery, biomimetic nanoclusters (2.5 mg/kg) which were readily dispersible, were injected into the tail vein. Five days later, arteries were collected for ex vivo Cy5 imaging using an in vivo imaging system (IVIS). We observed strong Cy5 fluorescent signals in injured artery segments, but could not detect Cy5 signals in the uninjured contralateral artery (FIGS. 2A-2B and FIG. 6). The imaging data suggest that systemically delivered platelet-membrane-coated nanoclusters can effectively target, and then accumulate on the injured arterial wall.

Figure 3A:
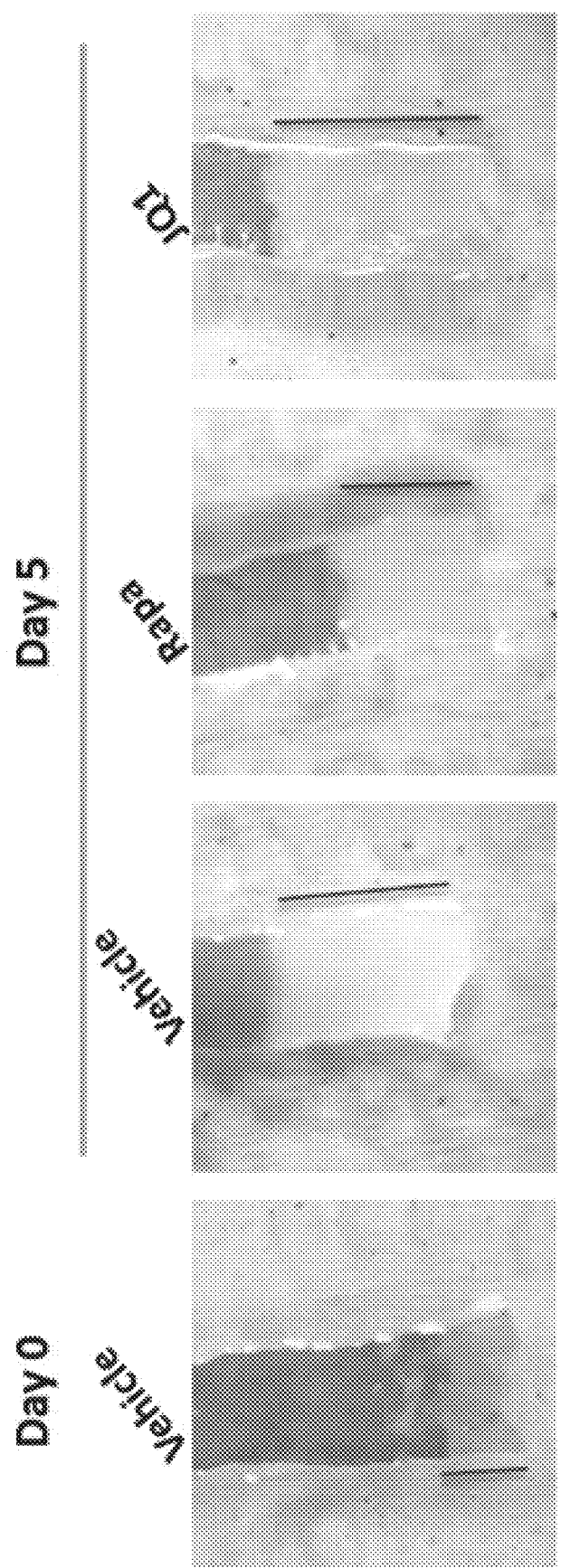
FIGS. 3A-3C can show the effects of drug-loaded biomimetic nanoclusters on re-endothelialization in balloon-injured arteries. Injections of biomimetic nanoclusters were performed as described in the Methods section. Animals were euthanized at 5 days post-angioplasty. Carotid arteries were collected and stained with Evans Blue. Denuded areas were stained blue; unstained (white) artery length indicate re-endothelialization (proximal end), which was quantified by normalizing to that of post-angioplasty Day 0.
Figure 3B:
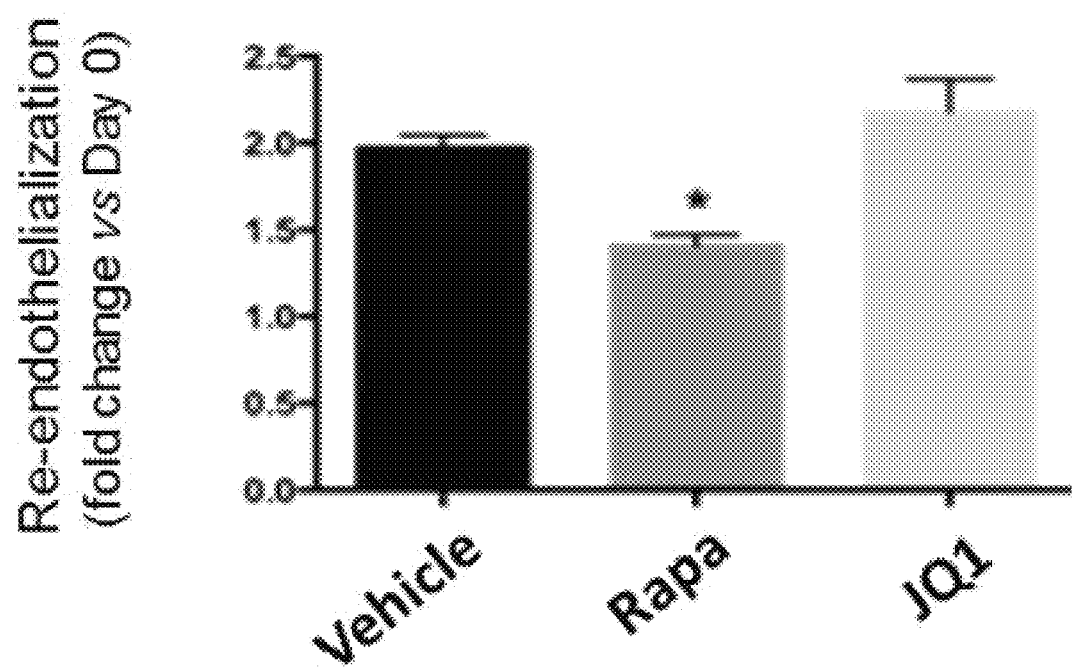
Figure 3C:
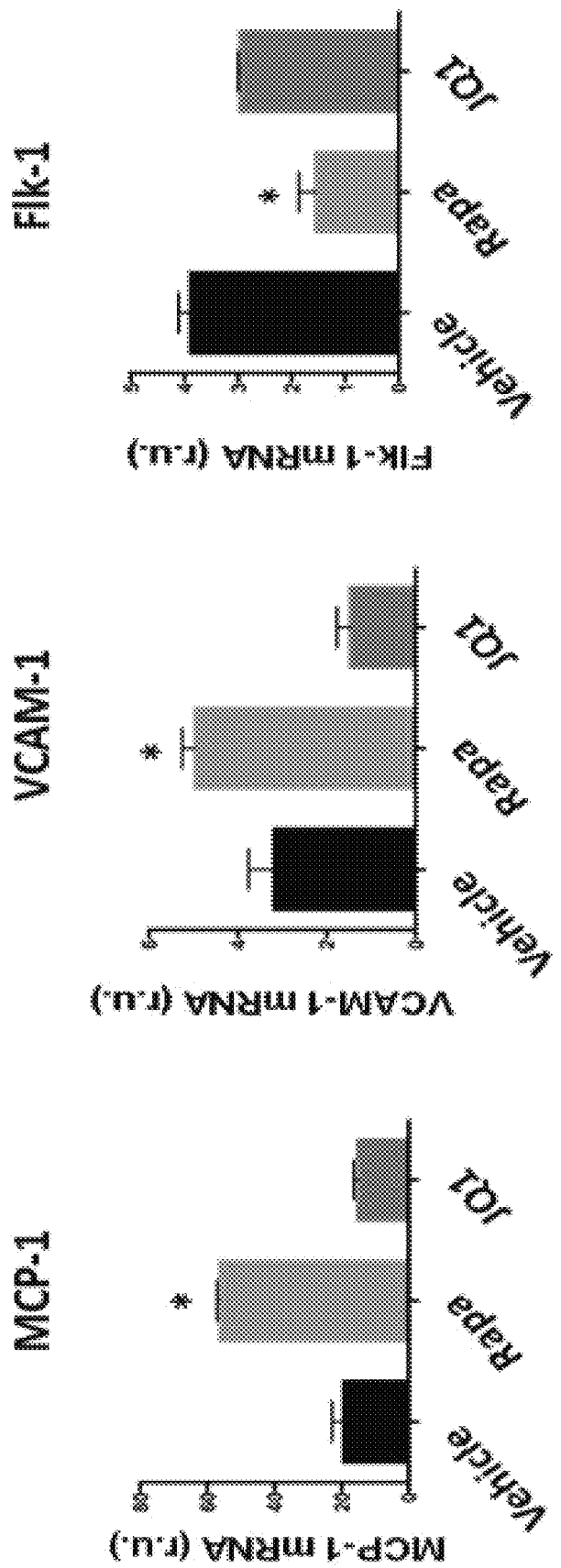

Results: JQ1-loaded but not rapamycin-loaded biomimetic nanoclusters preserve re-endothelialization of injured arteries. The major objective of this study was to create an endothelium-protective anti-restenotic system employing drug-containing biomimetic nanoclusters. We therefore compared the impacts of the rapamycin- and JQ1-containing nanocluster formulations on re-endothelialization 5 days after angioplasty (FIGS. 3A-3B). Since the nanoclusters without platelet membrane coating were prone to form aggregates, which prevented injection, we did not include this condition in the experiments. As revealed in FIG. 3A, right after angioplasty, the inner surface of balloon-injured artery was almost fully stained by Evans Blue, indicating denudation of endothelium. After 5 days without treatment, the proximal end of the injured artery could no longer be stained, indicative of re-coverage of this area by newly grown ECs. Consistent with a known EC-toxic effect (2), rapamycin delivered in biomimetic nanoclusters substantially impaired re-endothelialization. Remarkably, we found that this detrimental effect did not occur in the arteries treated with JQ1-loaded biomimetic nanoclusters. Rather, the treated arteries had even a greater endothelial coverage than empty nanoclusters (no drug), although the increase did not reach statistical significance in this experimental setting (FIG. 3A). Re-endothelialization progressed mainly from the proximal side of the denuded artery likely because at the distal end it was too slow to observe, which is common with the balloon angioplasty model (10). To further confirm this endothelium-preserving effect of the JQ1/nanocluster formulation, we determined its influence on EC phenotypic markers. Indeed, compared to control (no drug), whereas the rapamycin/nanocluster formulation markedly increased expression of VCAM-1 and MCP-1 mRNA, both indicating inflammatory deterioration of ECs (2), the JQ1/nanocluster formulation did not increase the expression of these two markers (FIG. 3B). Consistently, JQ1/nanoclusters did not, but rapamycin/nanoclusters did reduce expression of Flk-1, a surrogate of EC number (2).

Figure 4A:
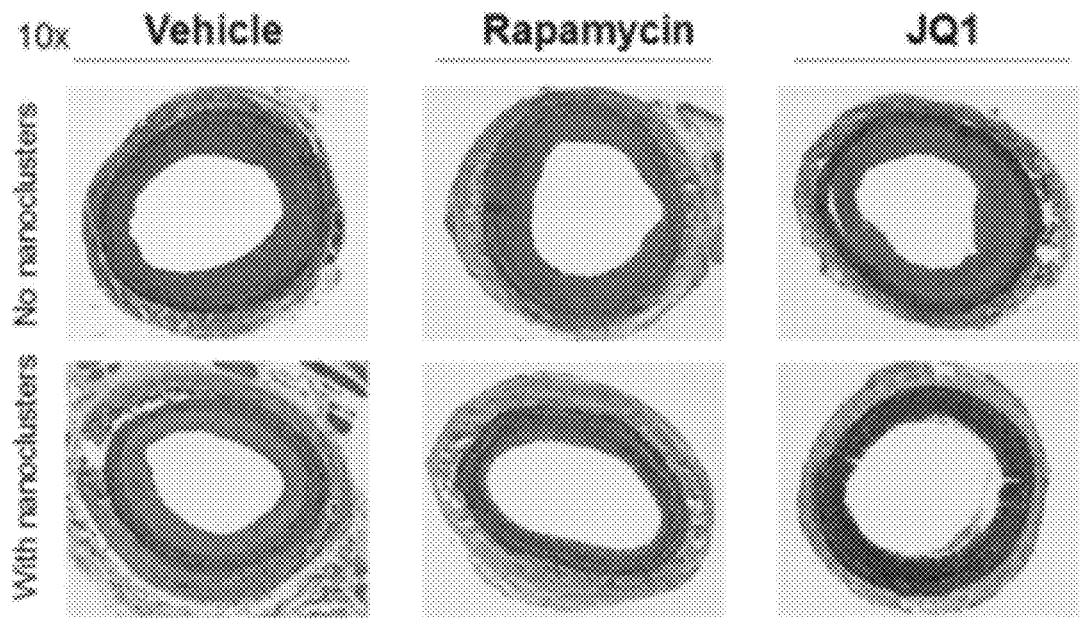
FIGS. 4A-4C can show the anti-restenotic effects of drug-loaded biomimetic nanoclusters in balloon-injured arteries. Rapamycin- or JQ1-loaded biomimetic nanoclusters, or their respective drug-only controls (no nanoclusters) were injected into the rat tail vein right after the carotid artery angioplasty. The injection was repeated 4 days later. Injected additional controls included PBS (no drug, no nanoclusters) and empty biomimetic nanoclusters (no drug). Animals were euthanized at 14 days post-angioplasty. Arteries were collected, and their cross-sections were prepared and Verhoeff-van Gieson (VvG)-stained for morphometric analysis. Neointimal hyperplasia (IH) was measured by the intimal/medial area ratio (I/M ratio); anti-restenotic effect was reflected by an increase (versus vehicle) of the lumen area. A. Representative images (10×) of VvG-stained artery sections. B. 40× images. C. Quantification of I/M ratios and lumen areas. One-way ANOVA followed by Bonferroni post-hoc analysis was performed. Mean±SEM, n=6-8 rats. **P<0.01 compared to any other condition except between Rapa and JQ1; *P<0.05 compared to the vehicle control (no nanoclusters); otherwise no significance was detected.
Figure 4B:
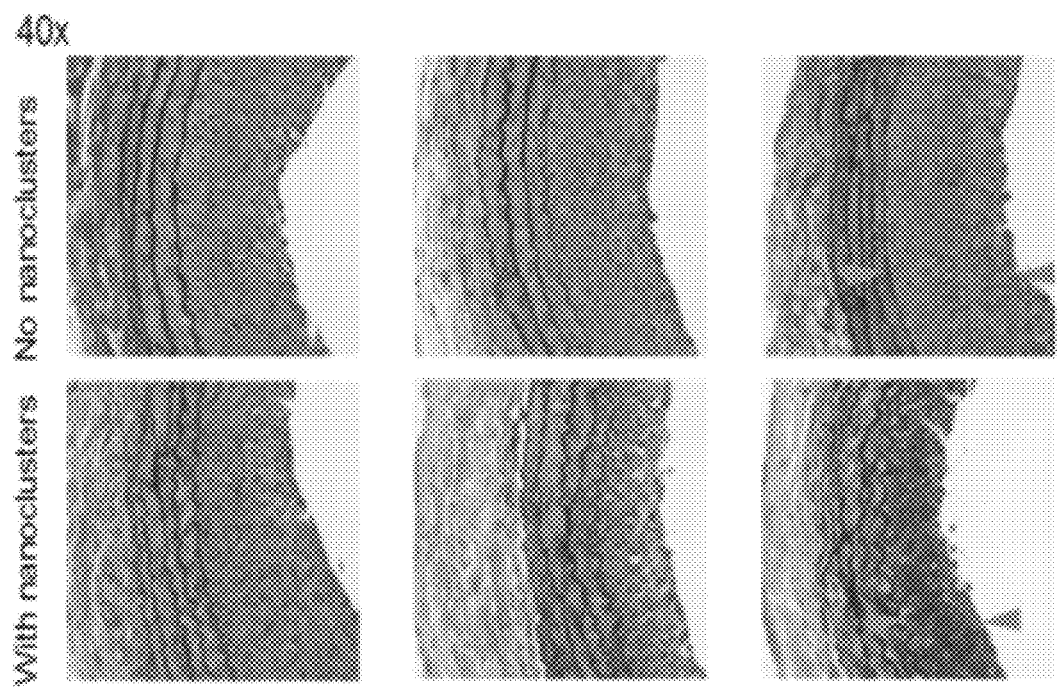
Figure 4C:
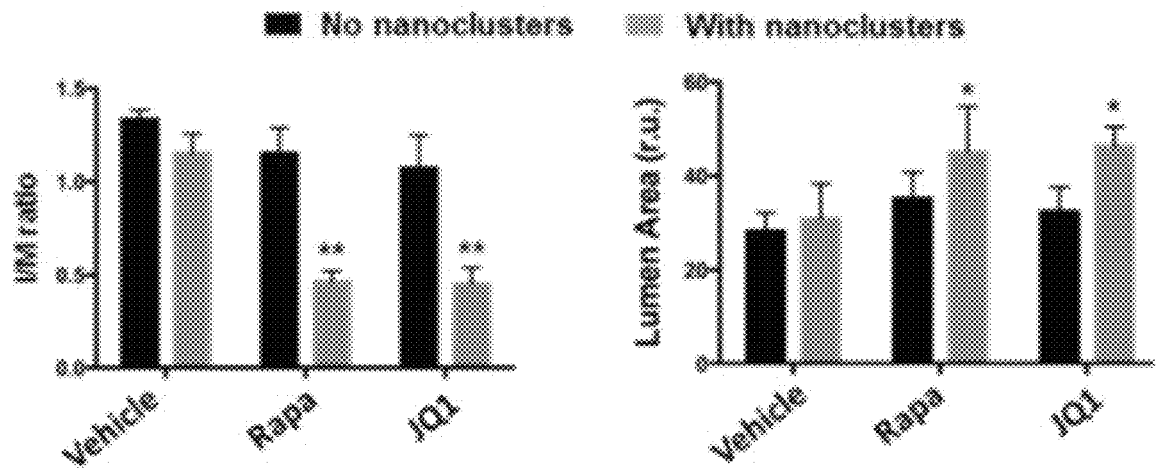
Figure 7:
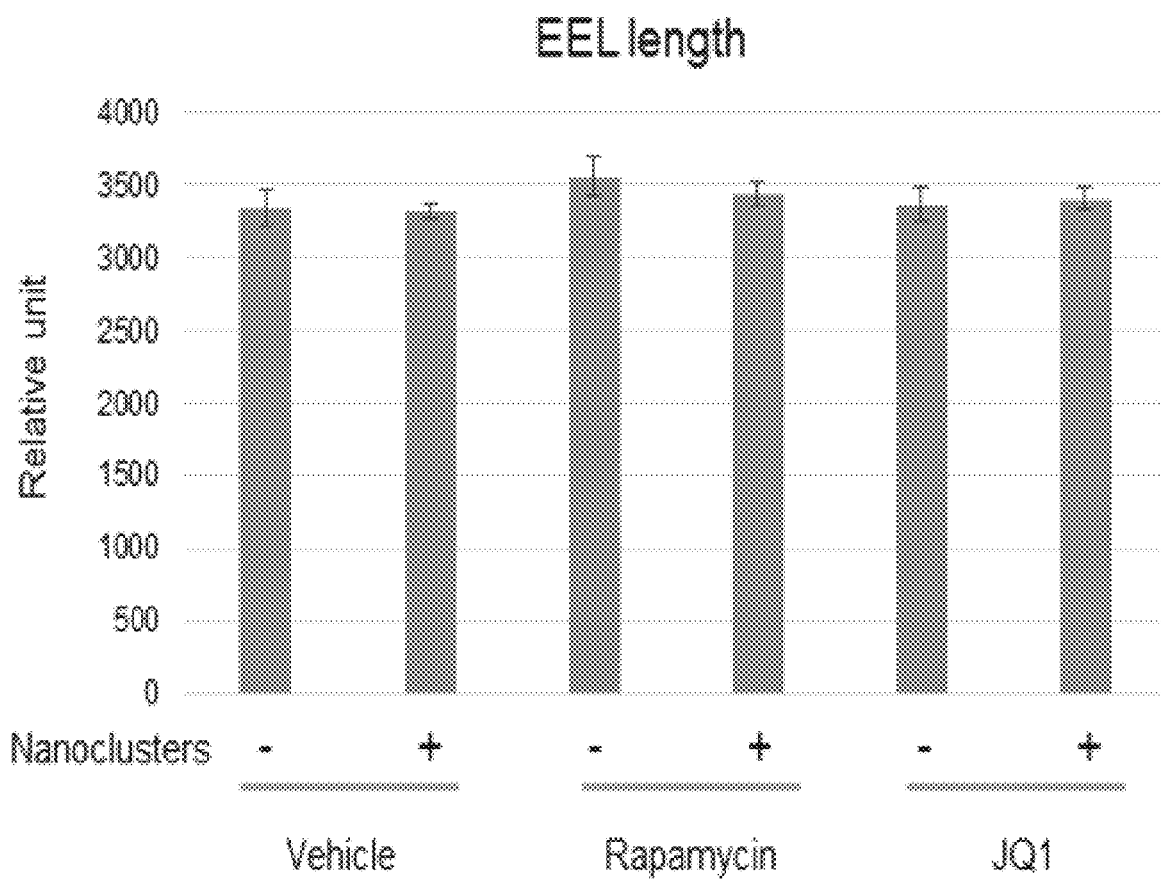
FIG. 7 shows a graph that can demonstrate the effect of drug-loaded biomimetic nanoclusters on the overall size of balloon-injured arteries. Experiments were performed as described with respect to FIGS. 3A-3B. Rapamycin- or JQ1-loaded biomimetic nanoclusters, or their respective drug-only controls (no nanoclusters) were injected into the rat tail vein right after the carotid artery angioplasty. The injection was repeated 4 days later. Injected additional controls included PBS (no drug, no nanoclusters) and empty biomimetic nanoclusters (no drug). Animals were euthanized 14 days after angioplasty, arteries were collected, and cross-sections were prepared and Verhoeff-van Gieson (VVG)-stained for morphometric analysis. The overall artery size was measured as EEL length. Quantification: Mean±SEM, n=6-8 rats.
Figure 8:
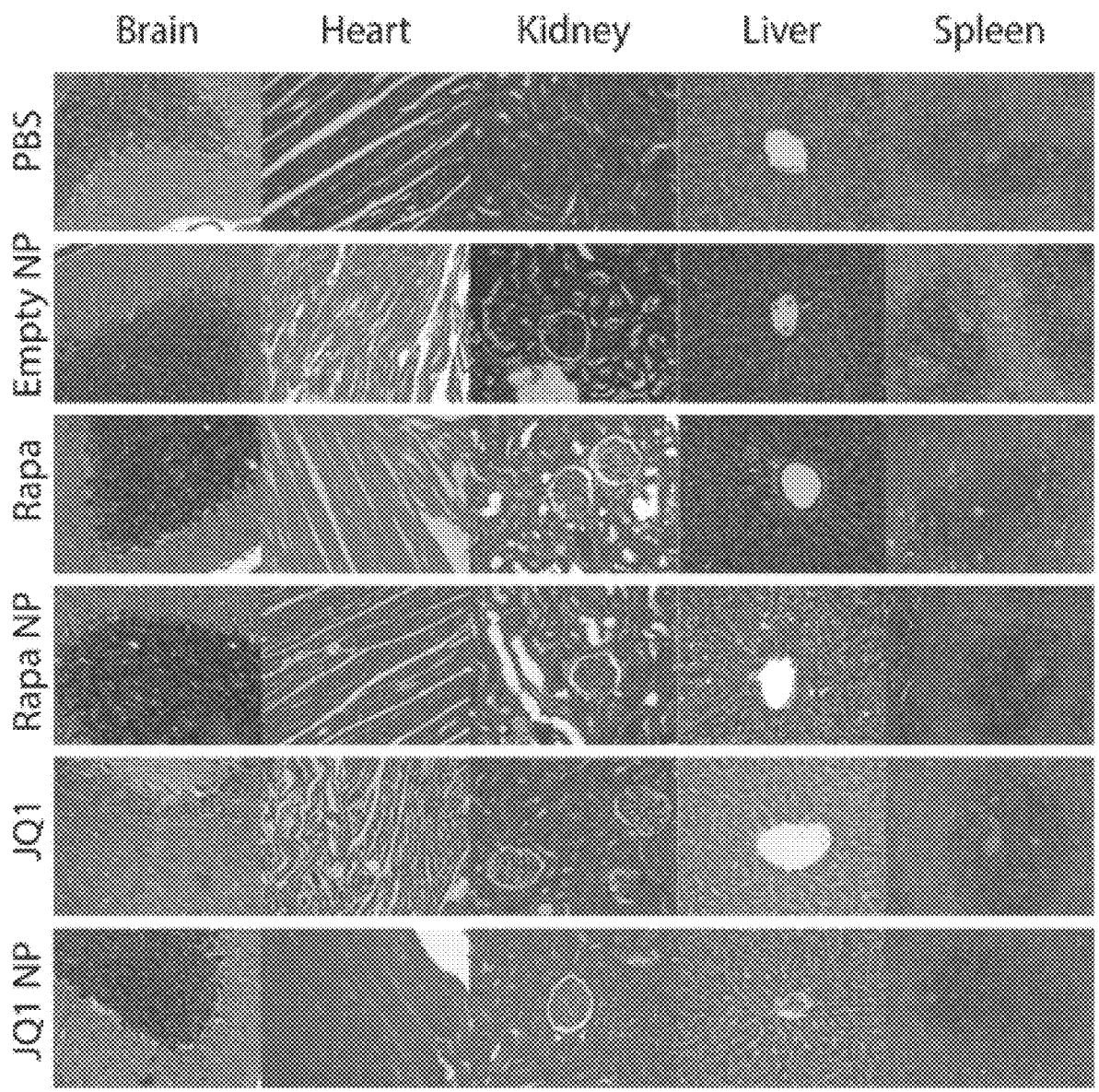
FIG. 8 shows images of tissue section staining that can demonstrate normal morphology. Experiments were performed as described in FIGS. 4A-4C. Rapamycin- or JQ1-loaded biomimetic nanoclusters, or empty nanoclusters (no drug) were injected into the rat tail vein right after the carotid artery angioplasty. The injection was repeated 4 days later. Rats were euthanized at day 14 after first injection and various organs were processed for tissue sections and H&E staining.
Figure 9:
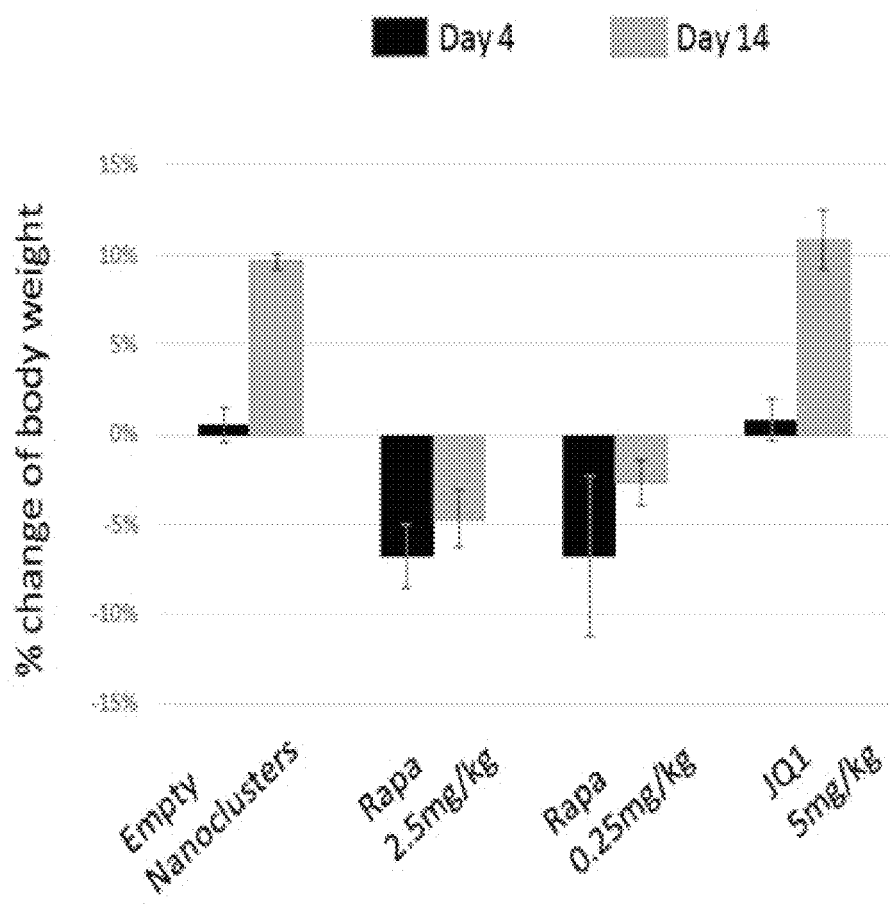
FIG. 9 shows a graph that can demonstrate an effect of drug-loaded biomimetic nanoclusters on rat body weight. Experiments were performed as described in FIGS. 3A-3B. Rapamycin- or JQ1-loaded biomimetic nanoclusters, or empty nanoclusters (no drug) were injected into the rat tail vein right after the carotid artery angioplasty. The injection was repeated 4 days later. Rats were weighed at indicated time points. Quantification: Mean±SEM, n=3-4 rats.

Results: JQ1-loaded biomimetic nanoclusters effectively inhibit the development of neointima. The anti-restenotic effects of biomimetic nanoclusters loaded with rapamycin and JQ1, respectively were compared. These drug-loaded biomimetic nanoclusters, or their respective drug-only controls (no nanoclusters), were intravenously injected immediately after balloon angioplasty. The injections were repeated 4 days later. In parallel, additional controls of PBS and empty biomimetic nanoclusters (no drug) were injected. The doses of rapamycin (0.25 mg/kg/injection) and JQ1 (5 mg/kg/injection) were chosen based on previous publications (2, 5) and our pilot experiments (data not shown). Two weeks after angioplasty, carotid arteries were collected for morphometric analysis. As shown in FIGS. 4A-48, compared to vehicle-only control, empty biomimetic nanoclusters did not affect IH (measured by the ratio). Compared to these two controls or drug-only controls (no nanoclusters), both rapamycin- and JQ1-loaded biomimetic nanoclusters inhibited IH by >60% (FIG. 4C) with the overall vessel size unaltered (FIG. 7). Although both formulations increased the lumen size, the effect of JQ1-loaded nanoclusters appeared to be more prominent. Interestingly, intravenous delivery of the same dose of free rapamycin or free JQ1 without using nanoclusters failed to mitigate IH. This indicates that delivery of rapamycin or JQ1 in a targeted manner using biomimetic nanoclusters can reduce the dose required for effective attenuation of IH. JQ1 in nanoclusters did not lead to systemic toxicity, as evidenced from the normal tissue morphologies of rat brain, heart, kidney, liver, and spleen (FIG. 8). Moreover, whereas prominent weight loss was observed over time with rapamycin/nanoclusters-treated rats, it was not observed in JQ1/nanoclusters-treated rats (FIG. 9).

Discussion DES implantation has become a procedure prevailingly used in the clinic to control post-angioplasty restenosis in the treatment of atherosclerosis. Unfortunately, it has been widely reported that DES exacerbates life-threatening stent thrombosis (1). This adverse effect is believed to stem from both the EC-toxic drug (e.g., rapamycin) coated on the stent and the stent itself as a non-biological object that intrudes into vascular tissues (1, 2). Here we have created a prototype stent-free biomimetic system that not only mitigates IH but importantly, also protects re-endothelialization, the healing step most critical to thrombosis prevention. This biomimetic formulation incorporates multiple innovations. First, it is injectable and hence stent-free. Second, the nanocluster is a more advanced drug nanocarrier than traditional NPs. Third, coating with biomembrane enables homing of drug-containing nanoclusters to the injury site where IH and thrombosis occur. Lastly, yet importantly, JQ1 represents a novel anti-restenotic epigenetic modulator with a unique function of endothelium protection (5, 6, 11). These features (further discussed below) together outline a new paradigm for a non-thrombogenic and stent-free anti-restenotic therapy.

Aside from a thrombogenic risk, other drawbacks inherent to DES are prominent as well. A stent insinuated into the arterial wall inflicts not only smooth muscle cell injury but also EC damage, both synergistically contributing to neointimal proliferation (12). Ample clinical evidence indicates that neointima can grow into the lumen through the struts of DES, causing in-stentrestenosis (1). Because the stent is not replaceable, an invasive open surgery would become necessary to bypass the restenotic artery. In contrast, repeated intravenous injections of biomimetic nanoclusters are readily convenient. Taking advantage of this feature, the treatment regimen can be adjusted based on the specific needs of individual patients. As such, a treatment plan could be designed toward precision medicine in a personalized manner.

In this Example, rather than using a traditional PLGA NP (9), it was opted to use a nanocluster formed by multiple PAMAM-PVL ultrasmall unimolecular NPs, which brings several advantages to the biomimetic therapeutic system. The PAMAM-PVL dendritic polymer forms a unimolecular NP consisting of only covalent bonds which can be used to encapsulate hydrophobic drug (13). Furthermore, the nanocluster can also offer versatile chemical modification. Both the core (e.g., PAMAM) and arms (e.g. PVL) can be readily modified for drug release profile optimization. Meanwhile, the dendritic polymers can be easily tailored (e.g., Cy5 in this study) to achieve multifunctionality. In addition, the nanocluster size can be controlled by adjusting the process parameters during the sonication or extrusion processes. Therefore, the nanoclusters are amenable to customization for optimal combination with biomembrane coating.

Coating nanoplatforms with biomembranes for targeted delivery represents a major innovation in nanomedicine (8). Biomembranes serving as an interface between cells and their surrounding mediate a myriad of interactions. They can thus be co-opted for targeting specific tissues or cells (14). For this purpose, there are a variety of sources of biomembranes capable of homing to the injured arterial wall, including mesenchymal stem cells, endothelial progenitor cells, and leukocytes. A prominent benefit of targeted delivery is a drastic decrease in effective drug doses. For example, the total amount of JQ1 used in our biomimetic nanoclusters (two injections) is about 70 fold lower than combined free JQ1 (twice daily injections) used for systemic delivery (3). This can be rationalized by reduced drug clearance rate, protection of drug by nanoclusters, and relatively high local drug concentrations at targeted sites. Lower effective JQ1 dose achieved using biomimetic nanoclusters should reduce side-effect concerns. While JQ1 is generally deemed non-toxic (15), it possibly blocks memory (16) or restrains bone growth in animals (17), underscoring the necessity of targeted delivery. It is worth noting that we did not observe obvious immune and inflammatory responses, likely because the platelet membranes were pre-inactivated to dampen their signaling functions (9). In addition, in our study platelet membrane coating renders drug-loaded nanoclusters readily dispersible in aqueous solutions and injectable. It is otherwise not practical to inject the non-coated nanoclusters as they are prone to form large aggregates, likely due to the relatively hydrophobic nature of the nanoclusters, which in fact is desirable for the platelet-membrane coating process.

A unique feature of our anti-restenotic biomimetic system is its endothelium-protective effect, which is largely owing to JQ1. In a stark contrast, the rapamycin/biomimetic nanocluster formulation impairs re-endothelialization. Previous studies including our own showed that JQ1 inhibits smooth muscle cell proliferation that forms neointima yet protects EC survival (5, 6). This may be explained by different signaling networks in the two cell types (12). Consistently, the epigenetic functions of JQ1's target, the BET protein family, are highly cell type- and cell state-specific (4, 6). While ECs are extremely susceptible to inflammatory insults, JQ1 proved to be a potent anti-inflammatory agent for ECs in vitro and in vivo (5, 6). It has been recently shown that JQ1 treatment of human umbilical vein ECs inhibits TNFα-induced pathogenic EC activation which is indicated by increased expression of E-selectin and vascular cell adhesion molecule (VCAM1) and NFNB nuclear translocation (6). Moreover, the inhibitory effects of JQ1 on pro-inflammatory activation of ECs and their monocyte recruiting were also observed in vivo in a hypercholesterolemic murine model of atherosclerosis (6). The molecular mechanism involves BET/NFNB-orchestrated super-enhancer remodeling that mediates inflammatory transcription and cell state transition in ECs, Though highly desirable, endothelium-protective anti-restenotic agents remain scarce (7). In this regard, identification of BET epigenetic regulators as endothelium-protective molecular targets is significant (5). The combined strengths of EC-friendly agents such as JQ1 and stent-free, targeted delivery using biomimetic nanoclusters may open a new avenue for next-generation anti-restenotic therapy.

Example Summary. DES thrombogenecity is a grave concern; the key problem is impaired endothelial recovery caused by both the drugs delivered by DES and stenting (1, 2). Developing an alternative method to DES has been a paramount challenge as it requires innovations in both drug and drug delivery device. The site of injury-targeting biomimetic system described herein radically departs from the status quo DES method. It has two prominent features, the use of an endothelium-protective epigenetic inhibitor and the omission of EC-damaging stenting, both contributing to the highly desirable preclinical outcome of suppressed IH and protected re-endothelialization. As endothelial damage is a common key etiology in major vascular diseases including atherosclerosis, restenosis, vein graft failure, and aneurysm (18), this anti-restenotic biomimetic system is expected to find broad applications. This system is advantageous for combination therapy, as biomembrane-coated nanoclusters containing different drugs can be mixed with varying ratios and co-injected. This confers considerable adjustability of constituent drugs, doses, and injection frequency etc., particularly in favor of personalized and precision medicine, which DES cannot provide References for Example 1 References in the foregoing example are cited with a reference corresponding to one or more of the following enclosed by parentheses. For example, citation of references 1 and 2 that following would be indicated as (1, 2).

1. Byrne R A, Joner M, & Kastrati A (2015) Stent thrombosis and restenosis: what have we learned and where are we going? The Andreas Gruntzig Lecture ESC 2014. *European heart journal* 36(47):3320-3331.
2. Camici G G, et al. (2010) Rapamycin promotes arterial thrombosis in vivo: implications for everolimus and zotarolimus eluting stents. *European heart journal* 31(2): 236-242.
3. Filippakopoulos P, et al. (2010) Selective inhibition of BET bromodomains. *Nature* 468(7327): 1067-1073.
4. Wang C Y & Filippakopoulos P (2015) Beating the odds: BETs in disease. *Trends in biochemical sciences* 40(8): 468-479.
5. Wang B, et al. (2015) BET Bromodomain Blockade Mitigates Intimal Hyperplasia in Rat Carotid Arteries. *EBioMedicine* 2(11):1650-1661.
6. Brown J D, et al. (2014) NF-kappaB directs dynamic super enhancer formation in inflammation and atherogenesis. *Molecular cell* 56(2):219-231.

7. Goel S A, et al. (2014) High-throughput screening identifies idarubicin as a preferential inhibitor of smooth muscle versus endothelial cell proliferation. *PloS one* 9(2): e89349.
8. Zhang P, Liu G, & Chen X (2017) Nanobiotechnology: Cell Membrane-Based Delivery Systems. *Nano Today* 13:7-9.
9. Hu C M, et al. (2015) Nanoparticle biointerfacing by platelet membrane cloaking. *Nature* 526(7571):118-121.
10. Grassia G, et al. (2009) The anti-inflammatory agent bindarit inhibits neointima formation in both rats and hyperlipidaemic mice. *Cardiovascular research* 84(3): 485-493.
11. Huang M, et al. (2016) BET Bromodomain Suppression Inhibits VEGF-induced Angiogenesis and Vascular Permeability by Blocking VEGFR2-mediated Activation of PAK1 and eNOS. *Scientific reports* 6:23770.
12. Balcells M, et al. (2010) Smooth muscle cells orchestrate the endothelial cell response to flow and injury. *Circulation* 121(20):2192-2199.
13. Chen G, et al. (2016) KE108-conjugated unimolecular micelles loaded with a novel HDAC inhibitor thailandepsin-A for targeted neuroendocrine cancer therapy. *Biomaterials* 97:22-33.
14. Sheikhpour M, Barani L, & Kasaeian A (2017) Biomimetics in drug delivery systems: A critical review. *Journal of controlled release: official journal of the Controlled Release Society* 253:97-109.
15. Asangani I A, et al. (2014) Therapeutic targeting of BET bromodomain proteins in castration-resistant prostate cancer. *Nature* 510(7504):278-282.
16. Korb E, Herre M, Zucker-Scharff I, Darnell R B, & Allis C D (2015) BET protein Brd4 activatestranscription in neurons and BET inhibitor Jq1 blocks memory in mice. *Nature neuroscience* 18(10): 1464-1473.
17. Niu N, Shao R, Yan G, & Zou W (2016) Bromodomain and Extra-terminal (BET) Protein InhibitorsSuppress Chondrocyte Differentiation and Restrain Bone Growth. *The Journal of biological chemistry* 291(52):26647-26657.
18. Augustin H G & Koh G Y (2017) Organotypic vasculature: From descriptive heterogeneity to functional pathophysiology. *Science*.
19. Zhao L, et al. (2017) An intraocular drug delivery system using targeted nanocarriers attenuates retinal ganglion cell degeneration. *Journal of Controlled Release* 247:153-166.
20. Guo L W, et al. (2014) Halofuginone stimulates adaptive remodeling and preserves re-endothelialization in balloon-injured rat carotid arteries. *Circ Cardiovasc Interv* 7(4):594-601.
21. Luk B T, Hu C-MJ, Fang R H, Dehaini D, Carpenter C, Gao W and Zhang L. Interfacial interactions between natural RBC membranes and synthetic polymeric nanoparticles. *Nanoscale*. 2014; 6:2730-2737.

Example 2

Reagents and Materials. Human platelets and peripheral blood mononuclear cells were purchased from Zen-Bio Inc (Research Triangle Park, NC). Human mesenchymal stem cells were purchased from Lonza (Basel, Switzerland). Mouse peritoneal macrophages were isolated from male C57/b6 mice as previously described. Mesenchymal stem cell-derived exosomes were harvested and purified using the Total Exosome Isolation Reagent kit from Thermo Fisher Scientific (Waltham, MA). Platelet membrane and exosome membrane were isolated using the freeze-thaw methods as described previously (Wang, B., et al., Biomaterials (2018) 178:293-301). Membrane from peripheral blood mononuclear cells, mesenchymal stem cells, and macrophages were isolated using ultracentrifugation-based method as described previously (Fang, R. H., et al., Nano Lett. (2014) 14(4): 2181-2188). RNAlater solution, TRIzol, SuperScript IV VILO Master Mix, and SYBR Green PCR Mastermix was purchased from Thermo Fisher Scientific (Waltham, MA). Poly(amidoamine) (PAMAM; 4th generation dendrimer), Evans Blue, dimethyl sulfoxide (DMSO), valerolactone (VL), and stannous (II) octoate ($Sn(Oct)_2$) were purchased from Sigma-Aldrich (St. Louis, MO). Rapamycin was purchased from LC Laboratories (Woburn, MA). JQ1 was purchased from ApexBio (Houston, TX). Cy5 dye was obtained from Lumiprobe Co. (Hallandale Beach, FL). Reagents not otherwise specified were purchased from Thermo Fisher Scientific (Waltham, MA).

Materials and Methods: Synthesis of drug-loaded biomimetic nanocluster. Nanoclusters were prepared as described in Example 1 using the various membranes prepared as described immediately above.

Materials and Methods: Mouse carotid artery aneurysm induction. Aneurysm induction using periadventitial application of calcium phosphate was performed in male C57/b6 mice as previously described. Briefly, rats were anesthetized with isoflurane (5% for inducing and 2.5% for maintaining anesthesia). A longitudinal incision was made in the neck and carotid arteries were exposed. Surgical gauze soaked with 0.5 M calcium chloride solution was applied in a perivascular fashion for 30 min, and then replaced with gauze soaked with phosphate balanced saline solution for 10 min. Biomimetic nanoclusters were administered via retroorbital injection at day 7 post calcium phosphate application.

Materials and Methods: IVIS imaging for homing of biomimetic nanoclusters. Cy5-tagged nanoclusters were coated with membranes derived from platelet, peripheral blood mononuclear cell, mesenchymal stem cell, or exosome, using the same method as described above, and tail-vein injected (2.5 mg/kg animal weight) immediately after balloon angioplasty of the rat carotid artery. Animal were euthanized at 5 days (for platelet-mimetic nanoclusters) and 1 day (for other nanoclusters) later. Various organs including balloon-injured arteries and uninjured contralateral arteries were collected for platelet membrane coated nanoclusters. Ex vivo fluorescence imaging was performed to track Cy5-tagged nanoclusters using an IVIS spectrum luminescence system (Ex/Em: 650/720 nm).

Figure 15A:
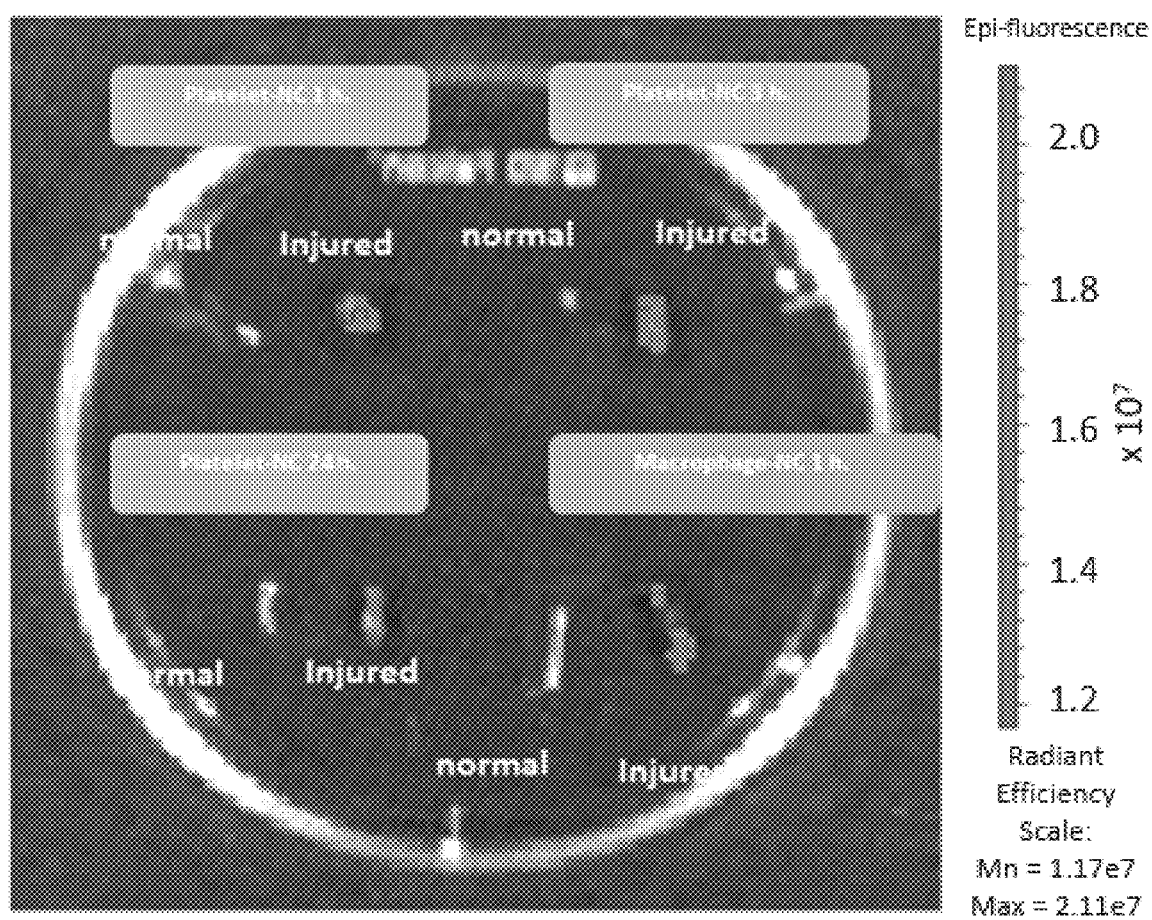
FIGS. 15A-15C show representative data for the biodistribution of platelet membrane-coated nanoclusters versus macrophage membrane-coated nanoclusters in mice.
Figure 15B:
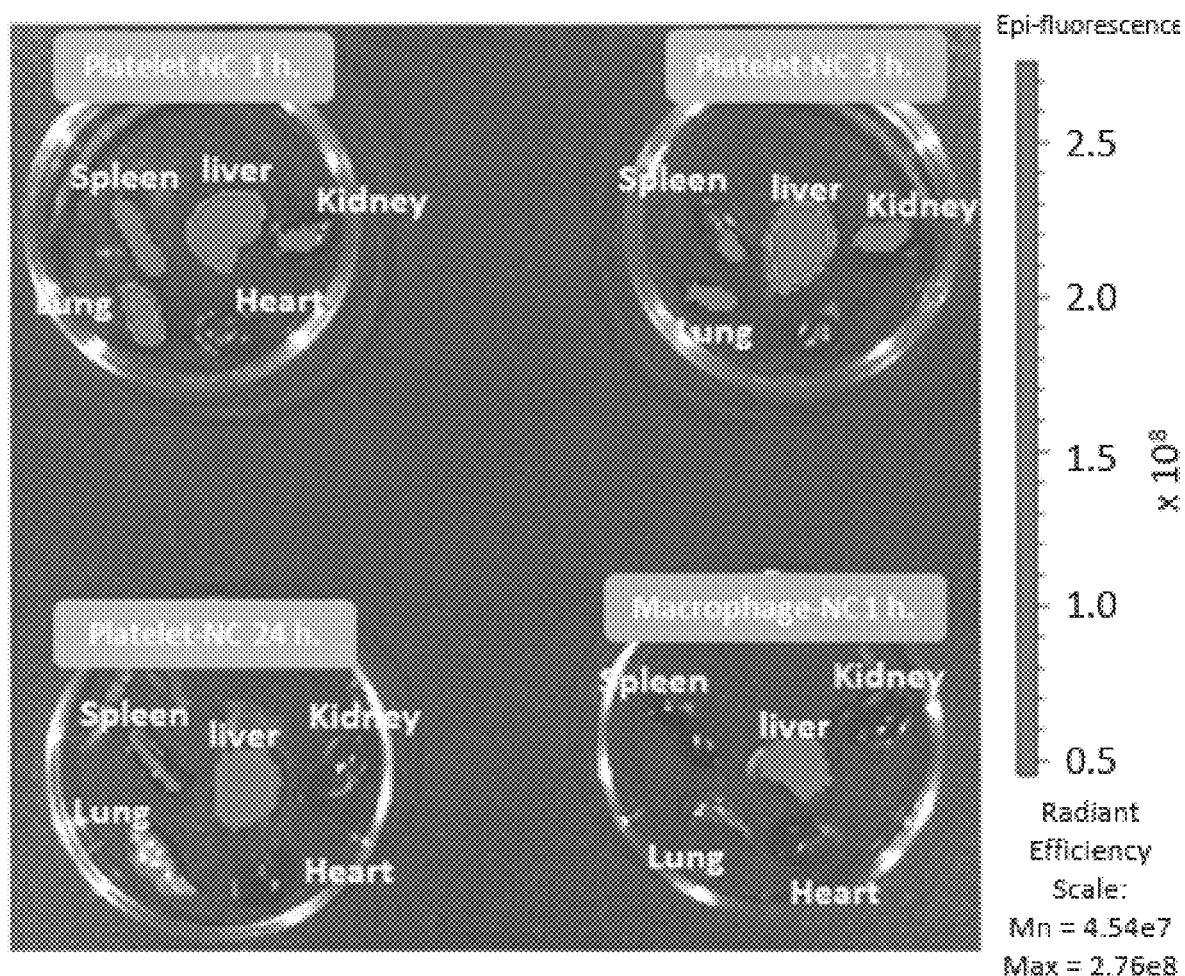
Figure 15C:
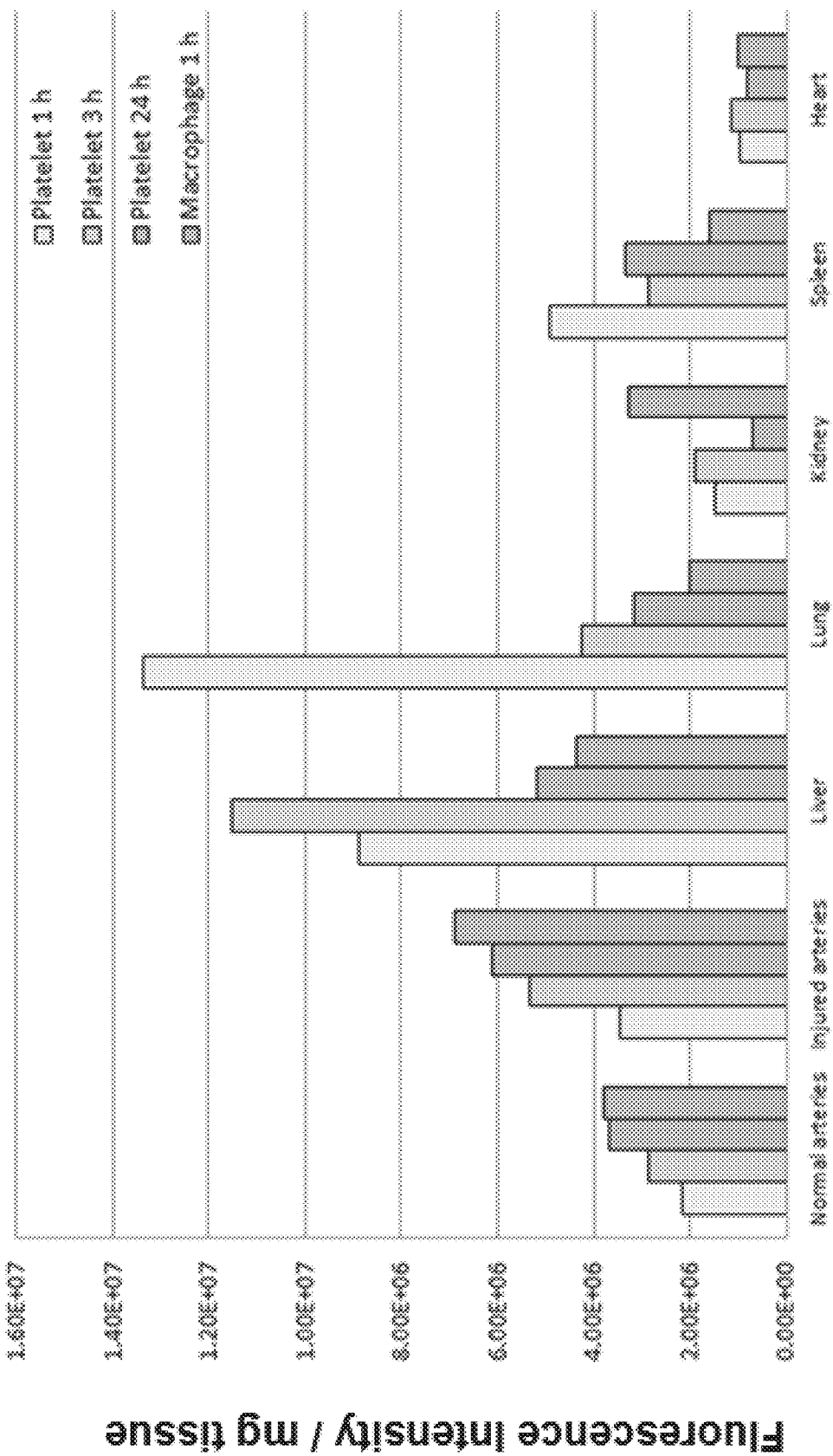
Figure 16:
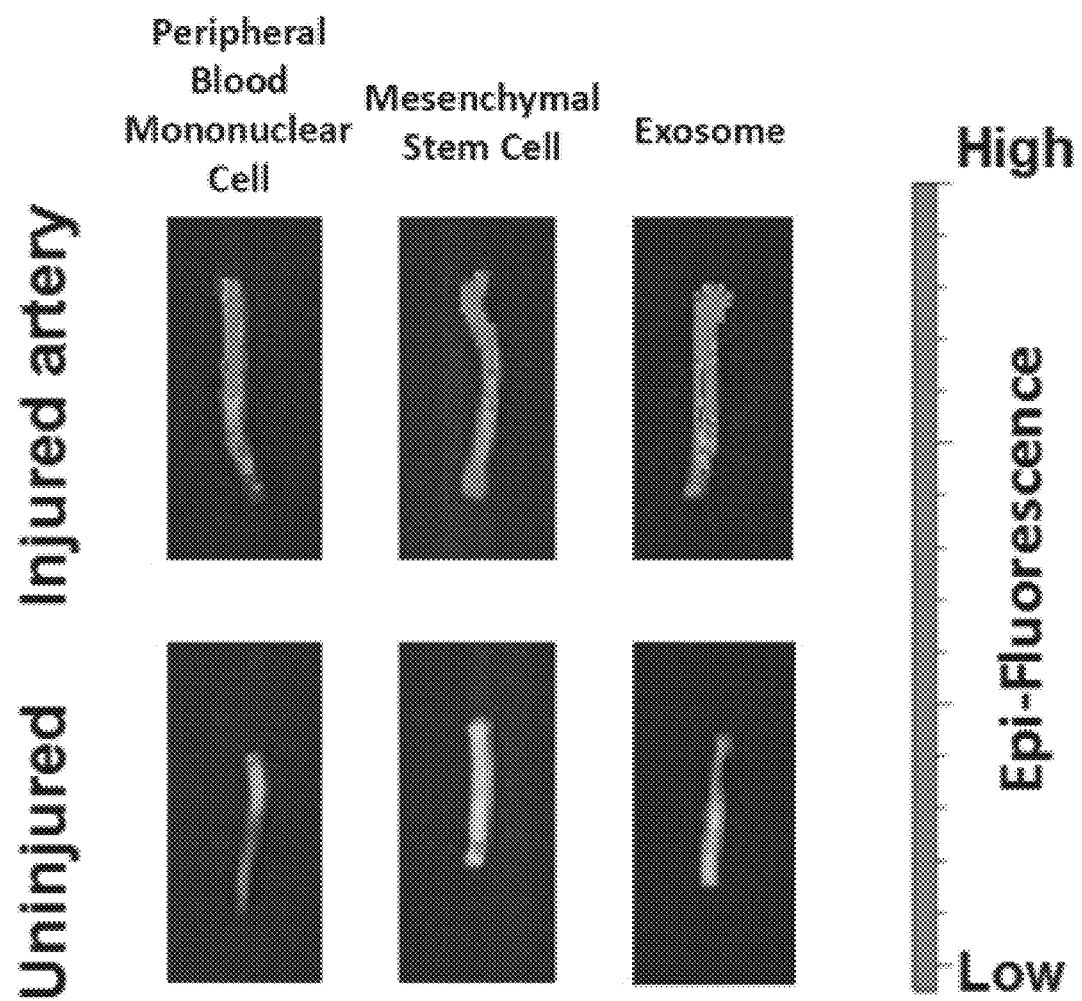
FIG. 16 shows representative data pertaining to target of representative disclosed nanoclusters coated with various membranes as indicated. The study was carried out as described for FIGS. 15A-15C, except using nanoclusters coated with membranes prepared from peripheral mononuclear cells, mesenchymal stem cells, and exosomes (as indicated in the figure). The imaging data shows targeting to injured artery sites by the various indicated coated nanoclusters, but essentially no targeting to contralateral uninjured arteries.

Results: Biomimetic nanoclusters can effectively home to a balloon-injured carotid artery wall. Biomimetic (coated with membranes from platelet, peripheral blood mononuclear cell, mesenchymal stem cell, and exosome) nanoclusters were prepared as described herein above and the data are shown in FIGS. 15A-15C. Detailed characterization of the biomimetic nanoclusters (e.g., size, zeta potential, and drug release profiles) was described above. Post-injection homing was visualized via the Cy5 fluorophores that were conjugated to the unimolecular NPs forming the nanoclusters. Immediately after balloon angioplasty in the rat carotid artery, biomimetic nanoclusters (2.5 mg/kg) which were readily dispersible, were injected into the tail vein. Arteries were collected for ex vivo Cy5 imaging using an in vivo imaging system (IVIS). Strong Cy5 fluorescent signals were observed in injured artery segments, but could not detect Cy5 signals in the uninjured contralateral artery (FIGS. 2A-2B and FIG. 6 for platelet membrane coated nanoclusters; FIGS. 15A-15C for nanoclusters coated with additional membrane types). The imaging data suggest that systemically delivered biomimetic (coated with membranes derived from platelet, peripheral blood mononuclear cell, mesenchymal stem cell, and exosome) nanoclusters all can effectively target, and then accumulate on the injured arterial wall.

It should be emphasized that the above-described aspects of the present disclosure are merely possible examples of implementations set forth for a clear understanding of the principles of the disclosure. Many variations and modifications may be made to the above-described aspect(s) without departing substantially from the spirit and principles of the disclosure. All such modifications and variations are intended to be included herein within the scope of this disclosure and protected by the following claims.

What is claimed is:

1. A biomimetic nanocluster comprising
a cell membrane structure comprising a first cell membrane component; and
a core structure comprising a plurality of unimolecular core-shell nanoparticles, wherein each unimolecular core-shell nanoparticle comprises a functionalized polymer,
wherein the functionalized polymer comprises a core-forming segment and a shell-forming segment, and
wherein a first pharmaceutical agent is attached to the core-forming polymer, the shell-forming polymer, or both the core-forming polymer and the shell-forming polymer;
wherein the functionalized polymer is PAMAM-PVL-COOH; and
wherein the first pharmaceutical agent is selected from a hydrophobic pharmaceutical agent; inhibits smooth muscle cell proliferation; a bromo and extraterminal (BET) protein inhibitor; a protein kinase RNA-like endoplasmic reticulum kinase (PERK) inhibitor; is resveratrol, rapamycin, sirolimus, paclitaxel, halofuginone, idarubicin, a derivative thereof; a PI3K/p110α inhibitor, a CTPS1 inhibitor, a EZH2 inhibitor, a Smad3 inhibitor, a PDGFR inhibitor, a TGFBR inhibitor, a derivative thereof, a pharmaceutically acceptable salt thereof, or any combination thereof;
wherein the cell membrane structure is prepared from a mesenchymal stem cell, a peripheral blood mononuclear cell, a platelet, or any combination thereof.

2. The biomimetic nanocluster of claim 1, wherein the core-forming segment is a generation 1, generation 2, generation 3, generation 4, or a generation 5 dendrimer.

3. The biomimetic nanocluster of claim 1, wherein the functionalized polymer is functionalized with terminal negatively charged groups.

4. The biomimetic nanocluster of claim 1, wherein the functionalized polymer is functionalized with terminal —COOH, —SO$_3$H, or —OPO$_3$H$_2$ groups, or a combination of groups thereof.

5. The biomimetic nanocluster of claim 1, wherein the shell-forming polymer is more hydrophobic relative to the core-forming polymer.

6. The biomimetic nanocluster of claim 1, wherein the core-forming polymer and the shell-forming polymer are hydrophobic and wherein the shell-forming polymer is more hydrophobic relative to the core-forming polymer.

7. The biomimetic nanocluster of claim 1, wherein the bromo and extraterminal (BET) protein inhibitor is JQ1, RVX208, RO6870810, FT-1101, CPI-0610, ZEN-3694, GSK525762, MK-8628, BMS-986158, INCB054329, RVX297, a derivative thereof, a pharmaceutically acceptable salt thereof, or any combination thereof.

8. The biomimetic nanocluster of claim 1, wherein the protein kinase RNA-like endoplasmic reticulum kinase (PERK) inhibitor is GSK2606414, GSK2656157, AMG PERK 44, a derivative thereof, a pharmaceutically acceptable salt thereof, or any combination thereof.

9. The biomimetic nanocluster of claim 1, wherein the first pharmaceutical agent is UNC1999, tubstatin-A, SIS3, imatinib, SB431542, cyclopentyl cytosine, a derivative thereof, a pharmaceutically acceptable salt thereof, or any combination thereof.

10. The biomimetic nanocluster of claim 1, further comprising a second pharmaceutical agent; and wherein the second pharmaceutical agent is an anti-inflammatory agent, an anti-thrombogenic agent, a lipid lowering agent with endothelium protection function, an anti-hypertensive agent, other epigenetic inhibitors, or any combination thereof.

11. The biomimetic nanocluster of claim 10, wherein the anti-inflammatory agent is diflusinal, ibuprofen, naproxen, ketoprofen, fenoprofen, flurbiprofen, fenbufen, benoxaprofen, tiaprofenic acid, indoprofen, suprofen, etodolac, zomepirac, indomethacin, alclofenac, sulindac, fenclofenac, diclofenac, tolmetin, mefanamic acid, phenylbutazone, oxyphenbuta, azapropazone, feprazone, or piroxicam, or any combination thereof.

12. The biomimetic nanocluster of claim 1, wherein the plurality of nanoparticles is homogeneous.

13. The biomimetic nanocluster of claim 1, wherein the plurality of nanoparticles is heterogeneous.

14. The biomimetic nanocluster of claim 1, wherein the diameter of the nanoclusters ranges from about 50 nm to about 200 nm.

15. The biomimetic nanocluster of claim 1, wherein the number of unimolecular core-shell nanoparticles in the plurality of unimolecular core-shell nanoparticles can range from about 20 to about 1500.

16. The biomimetic nanocluster of claim 1, wherein the diameter of the vesicle ranges from about 50 nm, to about 200 nm.

17. The biomimetic nanocluster of claim 1, wherein the vesicle is capable of targeting the vascular endothelium.

18. A method for treating cardiovascular disease or injury in a subject comprising: administering to the subject the biomimetic nanocluster of claim 1.

19. A kit comprising:
a biomimetic nanocluster of claim 1 to a subject; and
instructions to treat a subject with the unimolecular core-shell nanoparticle, the nanocluster, or
the biomimetic nanocluster.

* * * * *

```
                        SEQUENCE LISTING

Sequence total quantity: 8
SEQ ID NO: 1            moltype = DNA  length = 20
FEATURE                 Location/Qualifiers
source                  1..20
                        mol_type = other DNA
                        organism = synthetic construct
SEQUENCE: 1
ctcctctcgg gaaatgccac                                               20

SEQ ID NO: 2            moltype = DNA  length = 20
FEATURE                 Location/Qualifiers
source                  1..20
                        mol_type = other DNA
                        organism = synthetic construct
SEQUENCE: 2
aacaacggaa tccccaacct                                               20

SEQ ID NO: 3            moltype = DNA  length = 20
FEATURE                 Location/Qualifiers
source                  1..20
                        mol_type = other DNA
                        organism = synthetic construct
SEQUENCE: 3
cttccaagtg gctaagggca                                               20

SEQ ID NO: 4            moltype = DNA  length = 20
FEATURE                 Location/Qualifiers
source                  1..20
                        mol_type = other DNA
                        organism = synthetic construct
SEQUENCE: 4
tcaaagggag tcggggatct                                               20

SEQ ID NO: 5            moltype = DNA  length = 20
FEATURE                 Location/Qualifiers
source                  1..20
                        mol_type = other DNA
                        organism = synthetic construct
SEQUENCE: 5
cttccaagtg gctaagggca                                               20

SEQ ID NO: 6            moltype = DNA  length = 20
FEATURE                 Location/Qualifiers
source                  1..20
                        mol_type = other DNA
                        organism = synthetic construct
SEQUENCE: 6
tcaaagggag tcggggatct                                               20

SEQ ID NO: 7            moltype = DNA  length = 20
FEATURE                 Location/Qualifiers
source                  1..20
                        mol_type = other DNA
                        organism = synthetic construct
SEQUENCE: 7
gacatgccgc ctggagaaac                                               20

SEQ ID NO: 8            moltype = DNA  length = 20
FEATURE                 Location/Qualifiers
source                  1..20
                        mol_type = other DNA
                        organism = synthetic construct
SEQUENCE: 8
agcccaggat gcccttagt                                                20
```